(12) United States Patent
Ciske et al.

(10) Patent No.: US 6,559,145 B2
(45) Date of Patent: May 6, 2003

(54) HETEROCYCLE CARBOXAMIDES AS ANTIVIRAL AGENTS

(75) Inventors: Fred L. Ciske, Lawton, MI (US); Michael J. Genin, Paw Paw, MI (US); Byung Hyun Lee, Kalamazoo, MI (US); Mark E. Schnute, Kalamazoo, MI (US); Valerie A. Vaillancourt, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/887,794

(22) Filed: Jun. 22, 2001

(65) Prior Publication Data

US 2002/0025960 A1 Feb. 28, 2002

Related U.S. Application Data

(60) Provisional application No. 60/217,558, filed on Jul. 12, 2000, and provisional application No. 60/272,142, filed on Feb. 28, 2001.

(51) Int. Cl.[7] ............... A61K 31/536; L07D 471/02; A61P 43/00
(52) U.S. Cl. ............... 514/232.5; 514/300; 544/127; 546/123
(58) Field of Search ............... 514/232.5, 300; 544/127; 546/123

(56) References Cited

U.S. PATENT DOCUMENTS

| | | | |
|---|---|---|---|
| 5,753,666 A | 5/1998 | Beasley et al. | 514/258 |
| 5,891,878 A | 4/1999 | Beasley et al. | 514/247 |
| 5,945,431 A | 8/1999 | Jin et al. | 514/300 |

FOREIGN PATENT DOCUMENTS

| | | | |
|---|---|---|---|
| JP | 07033729 | 2/1995 | C07C/261/04 |
| JP | 08301849 | 11/1996 | C07D/217/26 |
| WO | WO97/04775 | 2/1997 | A61K/31/435 |
| WO | WO97/34894 | 9/1997 | C07D/471/06 |
| WO | WO98/11073 | 3/1998 | C07D/215/48 |
| WO | WO98/19673 | 5/1998 | A61K/31/165 |
| WO | WO99/10347 | 3/1999 | C07D/471/04 |
| WO | WO99/32450 | 7/1999 | C07D/215/56 |
| WO | WO00/40561 | 7/2000 | C07D/215/16 |
| WO | WO00/40562 | 7/2000 | C07D/215/48 |
| WO | WO00/40563 | 7/2000 | C07D/215/56 |
| WO | WO00/53610 | 9/2000 | C07D/513/04 |

*Primary Examiner*—Joseph K. McKane
*Assistant Examiner*—Andrea D. Small
(74) *Attorney, Agent, or Firm*—Lucy X. Yang; Andrew M. Solomon

(57) ABSTRACT

The present invention provides a compound of formula I

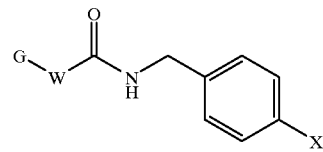

which is useful as antiviral agents, in particular, as agents against viruses of the herpes family.

25 Claims, No Drawings

HETEROCYCLE CARBOXAMIDES AS ANTIVIRAL AGENTS

CROSS-REFERENCE TO RELATED APPLICATIONS

This application claims the benefit of the following provisional applications: U.S. Ser. No. 60/217,558, filed Jul. 12, 2000; and U.S. Ser. No. 60/272,142, filed Feb. 28, 2001 under 35 USC 119(e)(i).

BACKGROUND OF THE INVENTION

1. Field of the Invention

The present invention provides heterocycle carboxamide derivatives. These compounds are useful as antiviral agents, in particular, as agents against viruses of the herpes family.

2. Technology Description

The herpesviruses comprise a large family of double stranded DNA viruses. They are also a source of the most common viral illnesses in man. Eight of the herpesviruses, herpes simplex virus types 1 and 2 (HSV-1 and HSV-2), varicella zoster virus (VZV), human cytomegalovirus (HCMV), Epstein-Barr virus (EBV), and human herpes viruses 6, 7, and 8 (HHV-6, HHV-7, and HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causative agent of chicken pox and shingles. EBV causes infectious mononucleosis. It can also cause lymphomas in immunocompromised patients and has been associated with Burkitt's lymphoma, nasopharyngeal carcinoma, and Hodgkin's disease. HHV-6 is the causative agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

U.S. Pat. Nos. 5,753,666 and 5,891,878 and WO 97/04775 disclose specific 1-alkyl-substituted-quinolone-3-carboxamides that are alleged to have therapeutic utility via inhibition of Phosphodiesterase IV esterase and/or Tumor Necrosis factor activity.

Commonly assigned WO 00/40561 discloses quinolinecarboxamides as antiviral agents.

Commonly assigned WO 00/40563 discloses specific quinolinecarboxamides as antiviral agents.

Commonly assigned WO 00/53610 discloses 4-Oxo-4,7-dihydrothieno[2,3-b]pyridine-5-carboxamides as antiviral agents.

Commonly assigned WO99/32450 discloses specific 4-hydroxyquinoline-3-carboxamides and hydrazides as antiviral agents.

U.S. Pat. No. 5,945,431 discloses specific naphthyridine heterocyclic compounds having antiviral activity that are useful in the therapy and prophylaxis of cytomegalovirus (CMV) infection in mammals.

WO99/10347 discloses specific substituted 4-oxo-naphthyridine-3-carboxamides as brain receptor ligands having potential use in the treatment of central nervous system diseases and/or disorders.

WO098/19673 discloses specific heterocyclic agents for the treatment of diseases caused by viruses.

JP08301849 discloses specific heterocyclic agents useful as tachykinin receptor antagonists. They are suggested for use in treatment of the following diseases: inflammation, allergic diseases, CNS disorders, digestive system disorders, urinary tract disorders, cardiovascular diseases immunopathy. The reference suggests that the inventive compounds can be used to treat herpes, but classifies herpes as either an inflammation or allergic reaction disease. The reference does not suggest that the compounds can be used to treat infectious diseases.

JP07033729 discloses specific N-cyano-N'-substituted-arylcarboxyimidamide compounds exhibiting K+ channel opening effects and having hypotensive action and coronary vasodilating action.

WO 00/40562 discloses novel 2-oxoquinolines as selective peripheral cannabinoid receptor modulators).

WO 97/34894 discloses Naphthyridine derivatives and their analogues inhibiting cytomegalovirus.

Despite the above teachings, there still exists a need in the art for novel compounds that demonstrate desirable antiviral activity.

BRIEF SUMMARY OF THE INVENTION

In accordance with the present invention, novel compounds which demonstrate antiviral activity are provided. More specifically, the compounds are specific heterocycle carboxamide derivatives which are useful as antiviral agents, particularly against herpesviruses.

Even more specifically, the present invention provides a compound of formula I,

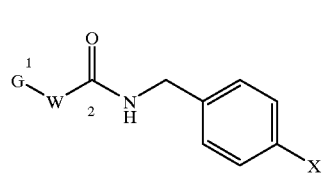

wherein,

X is Cl, Br, F, CN, or $NO_2$;

G is (a) $C_{1-4}$alkyl which is fully saturated or partially unsaturated and is substituted by hydroxy, or (b) $C_{1-4}$alkyl substituted by $NR^1R^2$ or 4-tetrahydropyran;

$R^1$ is $C_{2-7}$alkyl substituted by hydroxy, $C_{1-4}$alkoxy, heteroaryl, or aryl;

$R^2$ is hydrogen or $C_{1-7}$alkyl;

or $R^1$ and $R^2$ together with the nitrogen to which they are attached form morpholine which may be optionally substituted by aryl or $C_{1-7}$alkyl; or pyrrolidine substituted by hydroxy;

W is a heterocycle of formula W1, W2, W3, W4, W5, W6, W7, W8, W9, W10, W11, W12, W13, W14, W15, W16, W17, W18, W19, W20, W21 or W22

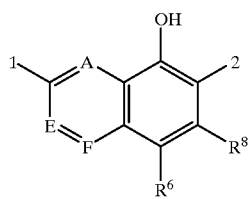 W1
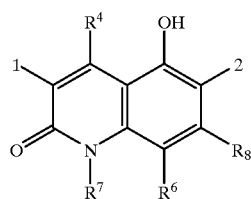 W2
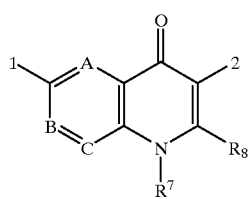 W3
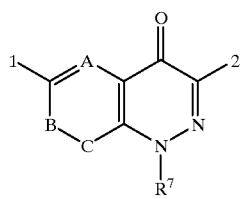 W4
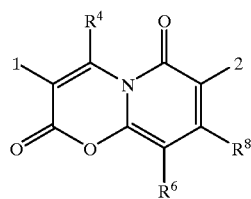 W5
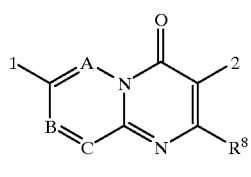 W6
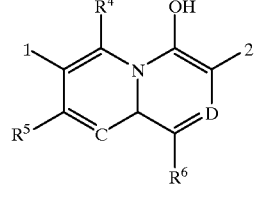 W7
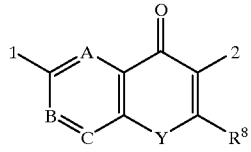 W8
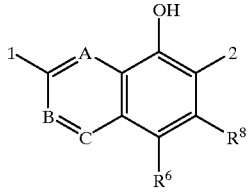 W9
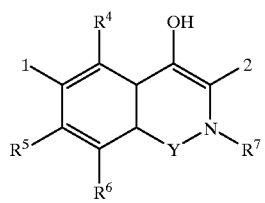 W10
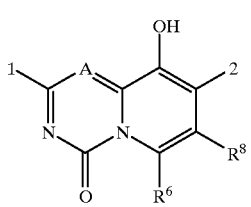 W11
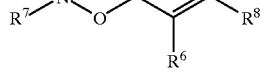 W12
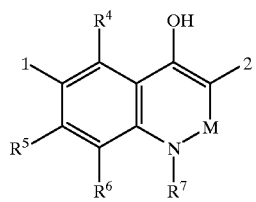 W13
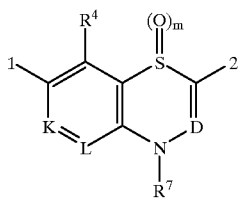 W14
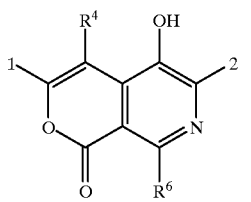 W15

-continued

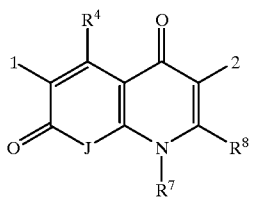
W16

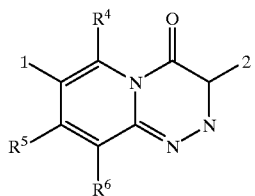
W17

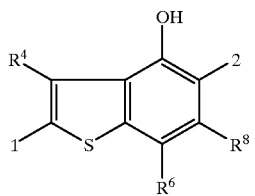
W18

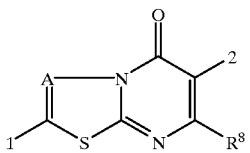
W19

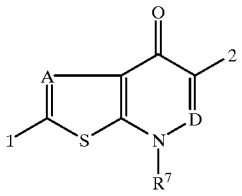
W20

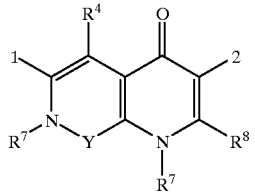
W21

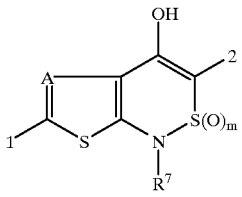
W22

A is $CR^4$ or nitrogen;
B is $CR^5$ or nitrogen;
C is $CR^6$ or nitrogen;
D is $CR^8$ or nitrogen;
E and F are such that one is oxygen and the other is C(=O);
J is $NR^7$ or oxygen;
K and L are defined such that
  (a) K is $CR^5$ and L is $CR^6$, or
  (b) K is absent and L is sulfur;

M is oxygen, sulfur, or $S(O)_m$;
Y is oxygen or sulfur;
with the provisos that:
when W is of formula W3 then at least one of A, B, or C is nitrogen and $R^7$ is other than H, and if C is nitrogen then A, B or A and B are nitrogen;
when W is of formula W4 then at least one of A, B, or C is nitrogen;
when W is of formula W9 then at least two of A, B, or C is nitrogen;
when W is of formula W16 and J is oxygen then $R^7$ is other than H;
when W is of formula W16 then J is other than NH;
when W is of formula W19, A is nitrogen, G is morpholinylmethyl, and X is chloro then $R^8$ is other than H;
when W is of formula W20 then at least one of A or D is nitrogen;
$R^4$ is H, halogen, or $C_{1-4}$alkyl optionally substituted by one to three halogens;
$R^5$ is
  (a) H,
  (b) halo,
  (c) $OR^{12}$,
  (d) $SR^{12}$,
  (e) $C_{1-7}$alkyl which may be partially unsaturated and optionally substituted by one or more substituents selected from $OR^{12}$, $SR^{12}$, $NR^{10}R^{11}$, or halo,
  (f) $C_{3-8}$cycloalkyl which may be partially unsaturated and is optionally substituted by one or more substituents selected from halogen, $OR^{12}$, $SR^{12}$, or $NR^{10}R^{11}$,
  (g) (C=O)$R^9$,
  (h) $S(O)_mR^9$,
  (i) (C=O)$OR^2$,
  (j) $NHSO_2R^9$,
  (k) nitro, or
  (l) cyano;
$R^6$ is
  (a) H,
  (b) halo,
  (c) aryl,
  (d) het,
  (e) $OR^{12}$,
  (f) $SR^{12}$,
  (g) $C_{1-7}$alkyl which may be partially unsaturated and optionally substituted by one or more substituents selected from $OR^{12}$, $SR^{12}$, $NR^{10}R^{11}$, aryl, halo, $C_{3-8}$cycloalkyl optionally substituted by $OR^{12}$, or het attached through a carbon atom,
  (h) $NR^{10}R^{11}$,
  (i) $C_{3-8}$cycloalkyl which may be partially unsaturated and is optionally substituted by one or more substituents selected from halogen, $OR^{12}$, $SR^{12}$, or $NR^{10}R^{11}$,
  (j) (C=O)$R^9$,
  (k) $S(O)_mR^9$,
  (l) (C=O)$OR^2$,
  (m) $NHSO_2R^9$,
  (n) nitro, or
  (o) cyano;
$R^7$ is
  (a) H,
  (b) $C_{1-7}$alkyl which may be partially unsaturated and optionally substituted by one or more substituents selected from $OR^{12}$, $SR^{12}$, $NR^{10}R^{11}$, or halo, (c) $C_{3-8}$cycloalkyl which may be partially unsaturated and is optionally substituted by one or more substituents selected from halogen, $OR^{12}$, $SR^{12}$, or $NR^{10}R^{11}$, (d) aryl, or (e) het;

$R^8$ is (a) H, (b) $C_{1-7}$alkyl which may be partially unsaturated and optionally substituted by one or more substituents selected from $OR^{12}$, $SR^{12}$, $NR^{10}R^{11}$, or halo, (c) $OR^{12}$, or (d) $SR^{12}$;

$R^9$ is (a) $C_{1-7}$alkyl, (b) $NR^{10}R^{11}$, (c) aryl, or (d) het, wherein said het is bound through a carbon atom;

$R^{10}$ and $R^{11}$ are independently (a) H, (b) aryl, (c) $C_{1-7}$alkyl which may be partially unsaturated and is optionally substituted by one or more substituents selected from $CONR^2R^2$, $CO_2R^2$, het, aryl, cyano, or halo, (d) $C_{2-7}$alkyl which may be partially unsaturated and is substituted by one or more substituents selected from $NR^2R^2$, $OR^2$, or $SR^2$, (e) $C_{3-8}$cycloalkyl which may be partially unsaturated and is optionally substituted by one or more substituents selected from halogen, $OR^2$, $SR^2$, or $NR^2R^2$, or (f) $R^{10}$ and $R^{11}$ together with the nitrogen to which they are attached form a het;

$R^{12}$ is (a) H, (b) aryl, (c) het (d) $C_{1-7}$alkyl optionally substituted by aryl, or halogen, (e) $C_{2-7}$alkyl substituted by $OR^2$, $SR^2$, or $NR^2R^2$, or (f) $C_{3-8}$cycloalkyl which may be partially unsaturated and is optionally substituted by one or more substituents selected from halogen, $OR^2$, $SR^2$, or $NR^2R^2$;

each m is independently 1 or 2;

aryl is a phenyl radical or an ortho-fused bicyclic carbocyclic radical wherein at least one ring is aromatic, and aryl maybe optionally substituted with one or more substituents selected from halo, OH, cyano, $NR^2R^2$, $CO_2R^2$, $CF_3$, $C_{1-6}$alkoxy, and $C_{1-6}$ alkyl which maybe further substituted by one to three $SR^2$, $NR^2R^2$, $OR^2$, or $CO_2R$ groups;

het is a four- (4), five- (5), six- (6), or seven- (7) membered saturated or unsaturated heterocyclic ring having 1, 2, or 3 heteroatoms selected from oxygen, sulfur, or nitrogen, which is optionally fused to a benzene ring, or any bicyclic heterocycle group, and het may be optionally substituted with one or more substituents selected from halo, OH, cyano, phenyl, $CO_2R^2$, $CF_3$, $C_{1-6}$alkoxy, oxo, oxime, and $C_{1-6}$ alkyl which may be further substituted by one to three $SR^2$, $NR^2R^2$, $OR^2$, or $CO_2R^2$ groups;

halo or halogen is F, Cl, Br, I;

1 represents the point of attachment between W and G;

2 represents the point of attachment between W and the carbonyl group of Formula (I);

and a pharmaceutically acceptable salt thereof.

In particularly preferred embodiments, X is Cl and G is 4-morpholinylmethyl.

Another embodiment of the present invention provides a pharmaceutical composition comprising a compound of formula (I) as defined above, or a pharmaceutically acceptable salt thereof, and a pharmaceutically acceptable carrier. In preferred embodiments, the composition preferably comprises a therapeutically effective amount of the compound or salt.

Still another embodiment of the present invention provides a method for treating a disease or condition in a mammal caused by a viral infection, particularly a herpes viral infection, comprising administering to the mammal a therapeutically effective amount of a compound of formula (I) or a pharmaceutically acceptable salt thereof.

A further embodiment of the present invention comprises the use of a compound of formula (I) or a pharmaceutically acceptable salt thereof to prepare a medicament for treating or preventing diseases or disorders caused by a viral infection, and particularly a herpes viral infection.

A final embodiment of the present invention comprises a method for inhibiting a viral DNA polymerase, comprising contacting (in vitro or in vivo) the polymerase with an effective inhibitory amount of a compound of formula (I) or a pharmaceutically acceptable salt thereof.

An object of the present invention is to provide novel compounds having biological activity.

A further object of the present invention is to provide novel pharmaceutical compositions.

Still another object of the present invention is to provide a method for treating a disease or condition in a mammal caused by a viral infection, particularly a herpes virus infection.

Another object of the present invention is to provide a method for inhibiting a viral DNA polymerase.

Still another object of the present invention is to provide novel intermediates useful for the preparation of the compound of the present invention.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

1. Terminology Definitions

The following definitions are used, unless otherwise described: halo is fluoro, chloro, bromo, or iodo. Alkyl denotes both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g., 1, 2, 3, or 4) double or triple bonds in the chain.

Aryl denotes a phenyl radical or an ortho-fused bicyclic carbocyclic radical wherein at least one ring is aromatic. Het is a four- (4), five- (5), six- (6), or seven- (7) membered saturated or unsaturated ring containing 1, 2 or 3 heteroatoms selected from the group consisting of non-peroxide oxygen, sulfur, and nitrogen, which is optionally fused to a benzene ring, or any bicyclic heterocyclic group. Het includes "heteroaryl", which encompasses a radical attached via a ring carbon of a monocyclic aromatic ring containing five or six ring atoms consisting of carbon and 1, 2, 3, or 4 heteroatoms each selected from the group consisting of non-peroxide oxygen, sulfur, and N(X) wherein X is absent or is H, O, $C_{1-4}$alkyl, phenyl or benzyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents. The compounds of the invention include compounds of formula (I) having any combination of the values, specific values, more specific values, and preferred values described herein.

Mammal denotes human and animals, specifically including food animals and companion animals.

2. The Invention

The present invention comprises compounds of formula (I) as defined above, and their pharmaceutically acceptable salts.

For the compounds of formula (I), alkyl can be methyl, ethyl, propyl, isopropyl, butyl, iso-butyl, sec-butyl, pentyl, 3-pentyl, hexyl, heptyl, etc.; $C_{3-8}$cycloalkyl can be cyclopropyl, cyclobutyl, cyclopentyl, cyclohexyl, cycloheptyl, or cyclooctyl; alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; het can be azetidinyl, 3,3-dihydroxy-1-azetinyl, pyrrolidino, piperidino, morpholino, thiomorpholino, or heteroaryl; and heteroaryl can be furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

When alkyl is partially unsaturated, it can be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, or 5-hexynyl.

Specific examples of W 1 include,

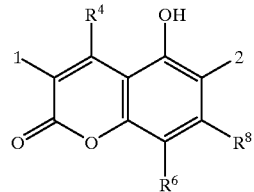
W1.1

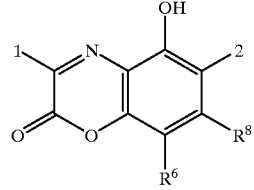
W1.2

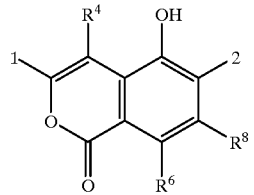
W1.3

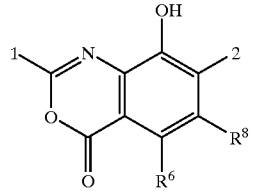
W1.4

Specific examples of W3 include,

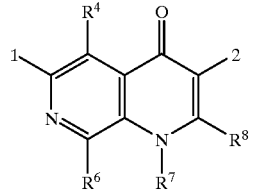
W3.1

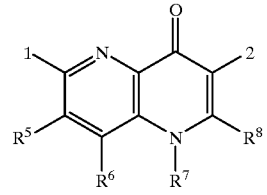
W3.2

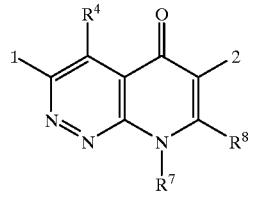
W3.3

W3.4
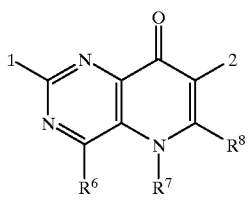
W3.5
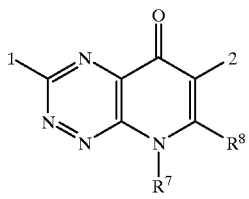
W3.6
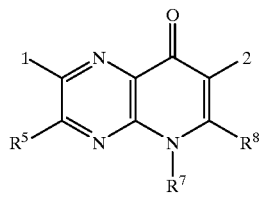
Specific examples of W4 include,
W4.1
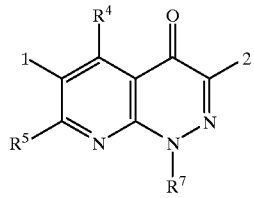
W4.2
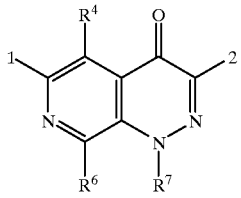
W4.3
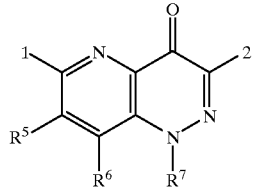
W4.4
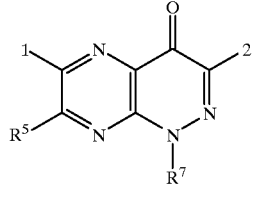
W4.5
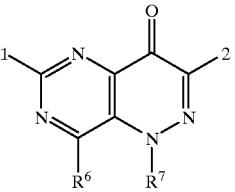
W4.6
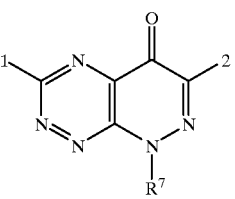
Specific examples of W6 include,
W6.1
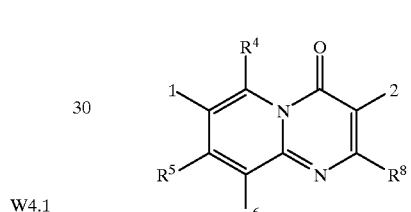
W6.2
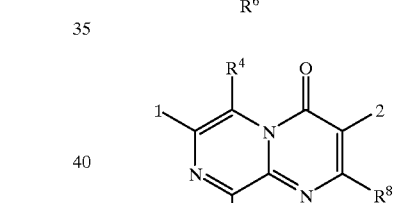
W6.3
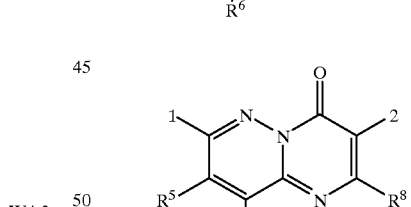
W6.4
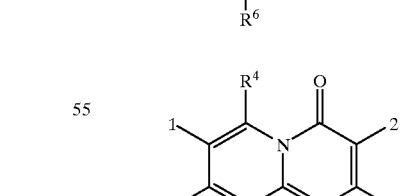
W6.5
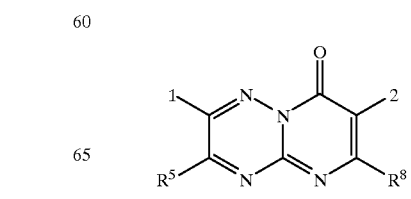

-continued
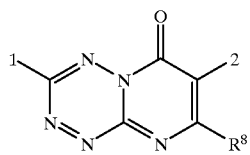
W6.6
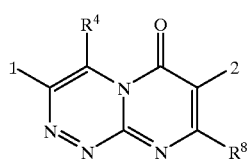
W6.7
Specific examples of W7 include,
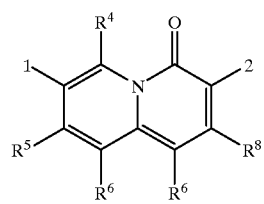
W7.1
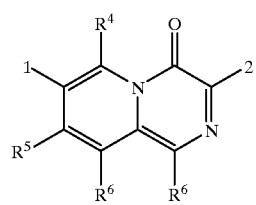
W7.2
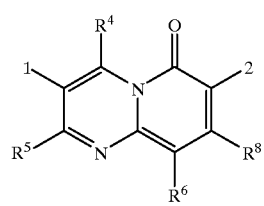
W7.3
Specific examples of W8 include,
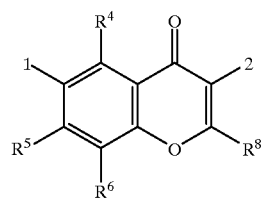
W8.1
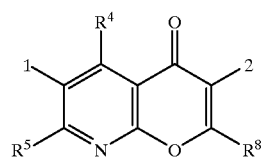
W8.2
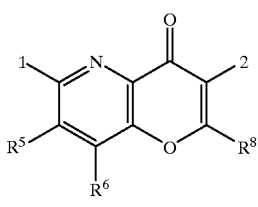
W8.3
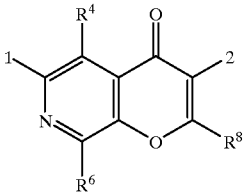
W8.4
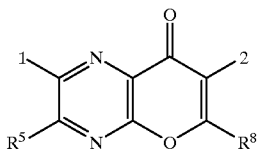
W8.5
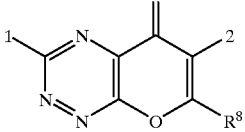
W8.6
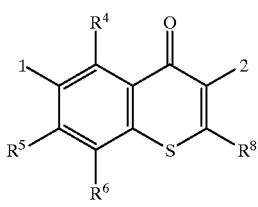
W8.7
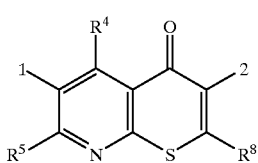
W8.8
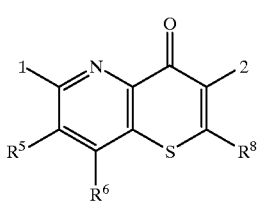
W8.9
W8.10

Specific examples of W9 include,

Specific examples of W10 include,

Specific examples of W 11 include,

Specific examples of W13 include,

-continued
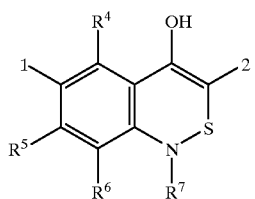
W13.2
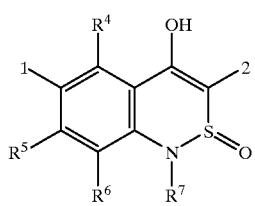
W13.3
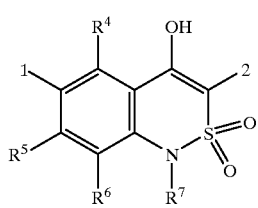
W13.4
Specific examples of W14 include,
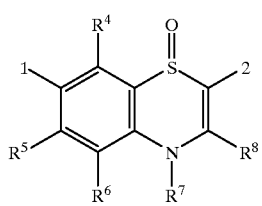
W14.1
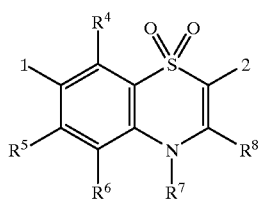
W14.2
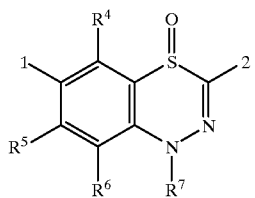
W14.3
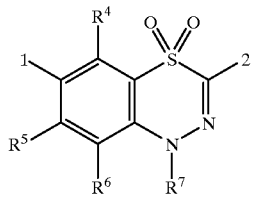
W14.4
-continued
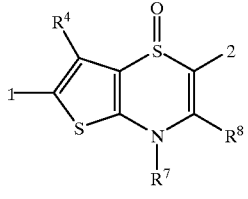
W14.5
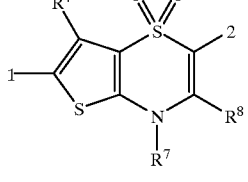
W14.6
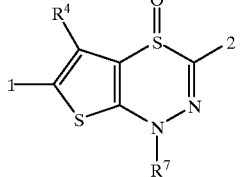
W14.7
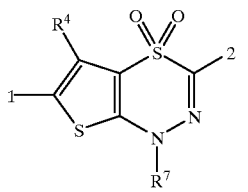
W14.8
Specific examples of W 16 include,
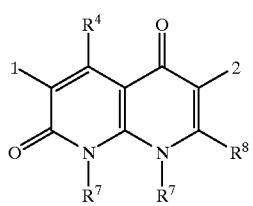
W16.1
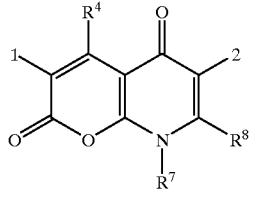
W16.2
Specific examples of W19 include,
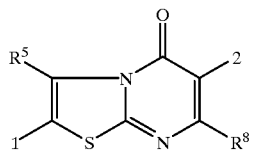
W19.1

-continued

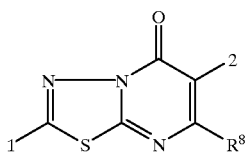
W19.2

Specific examples of W20 include,

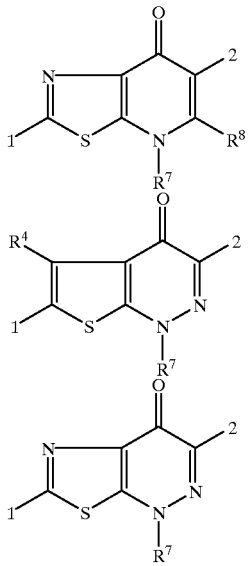
W20.1

W20.2

W20.3

Specific examples of W21 include,

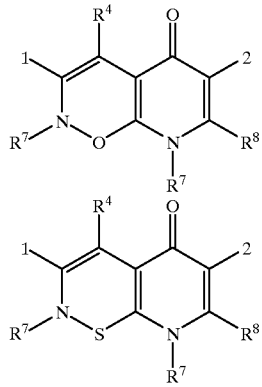
W21.1

W21.2

Specific examples of W22 include,

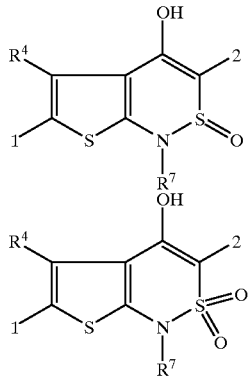
W22.1

W22.2

-continued

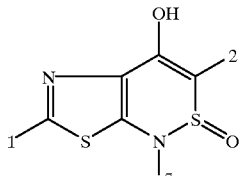
W22.3

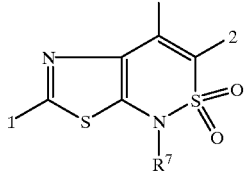
W22.4

Particularly preferred compounds are those where X is Cl and G is 4-morpholinylmethyl.

Examples of the present invention include, but are not limited to the following:

N-(4-chlorobenzyl)-5-hydroxy-3-(3-hydroxy-1-propynyl)-2-oxo-2H-chromene-6-carboxamide;

N-(4-chlorobenzyl)-5-hydroxy-3-(3-hydroxypropyl)-2-oxo-2H-chromene-6-carboxamide;

N-(4-chlorobenzyl)-5-hydroxy-3-(4-morpholinylmethyl)-2-oxo-2H-chromene-6-carboxamide;

N-(4-chlorobenzyl)-5-hydroxy-4-methyl-3,8-bis(4-morpholinylmethyl)-2-oxo-2H-chromene-6-carboxamide;

N-(4-chlorobenzyl)-5-hydroxy-3-(3-hydroxy-1-propynyl)-1-methyl-2-oxo-1,2-dihydro-6-quinolinecarboxamide;

N-(4-chlorobenzyl)-5-hydroxy-3-(3-hydroxypropyl)-1-methyl-2-oxo-1,2-dihydro-6-quinolinecarboxamide;

N-(4-chlorobenzyl)-5-hydroxy-1-methyl-3-(4-morpholinylmethyl)-2-oxo-1,2-dihydro-6-quinolinecarboxamide;

N-(4-chlorobenzyl)-6-(3-hydroxy-1-propynyl)-1-methyl-4-oxo-1,4-dihydro[1,7]-naphthyridine-3-carboxamide;

N-(4-chlorobenzyl)-6-(3-hydroxypropyl)-1-methyl-4-oxo-1,4-dihydro[1,7]-naphthyridine-3-carboxamide;

N-(4-chlorobenzyl)-8-ethoxy-6-(3-hydroxy-1-propynyl)-1-methyl-4-oxo-1,4-dihydro[1,7]naphthyridine-3-carboxamide;

N-(4-chlorobenzyl)-8-ethoxy-6-(3-hydroxypropyl)-1-methyl-4-oxo-1,4-dihydro[1,7]-naphthyridine-3-carboxamide;

N-(4-chlorobenzyl)-1-methyl-6-(4-morpholinylmethyl)-4-oxo-1,4-dihydro[1,7]-naphthyridine-3-carboxamide;

8-chloro-N-(4-chlorobenzyl)-1-methyl-6-(4-morpholinylmethyl)-4-oxo-1,4-dihydro -1,7]naphthyridine-3-carboxamide;

N-(4-chlorobenzyl)-8-ethoxy-1-methyl-6-(4-morpholinylmethyl)-4-oxo-1,4-dihydro[1,7]naphthyridine-3-carboxamide;

N-(4-chlorobenzyl)-1-methyl-6,8-bis(morpholin-4-ylmethyl)-4-oxo-1,4-dihydro-1,7-naphthyridine-3-carboxamide;

N-(4-chlorobenzyl)-6-(3-hydroxypropyl)-1-methyl-4-oxo-1,4-dihydro[1,5]-naphthyridine-3-carboxamide;

N-(4-chlorobenzyl)-6-(3-hydroxy-1-propynyl)-1-methyl4-oxo-1,4-dihydro[1,5]-naphthyridine-3-carboxamide;

N-(4-chlorobenzyl)-1-methyl-6-(4-morpholinylmethyl)-4-oxo-1,4-dihydro[1,5]-naphthyridine-3-carboxamide;

N-(4-chlorobenzyl)-1-methyl4-oxo-6-(tetrahydro-2H-pyran-4-ylmethyl)-1,4-dihydro[1,5]naphthyridine-3-carboxamide;

N-(4-chlorobenzyl)-8-ethyl-3-(4-morpholinylmethyl)-5-oxo-5,8-dihydropyrido[2,3-c] pyridazine-6-carboxamide;

N-(4-chlorobenzyl)-2-(3-hydroxypropyl)-5-methyl-8-oxo-5,8-dihydropyrido[3,2-d]-pyrimidine-7-carboxamide;
N-(4-chlorobenzyl)-2-(3-hydroxy-1-propynyl)-5-methyl-8-oxo-5,8-dihydropyrido-[3,2-d]pyrimidine-7-carboxamide;
N-(4-chlorobenzyl)-5-methyl-2-(4-morpholinylmethyl)-8-oxo-5,8-dihydropyrido[3,2-d]pyrimidine-7-carboxamide;
N-(4-chlorobenzyl)-6-(3-hydroxy-1-propynyl)-1-methyl-4-oxo-1,4-dihydropyrido-[2,3-c]pyridazine-3-carboxamide;
N-(4-chlorobenzyl)-6-(3-hydroxypropyl)-1-methyl-4-oxo-1,4-dihydropyrido[2,3-c]-pyridazine-3-carboxamide;
N-(4-chlorobenzyl)-1-methyl-6-(4-morpholinylmethyl)-4-oxo-1,4-dihydropyrido[2,3-c]pyridazine-3-carboxamide;
N-(4-chlorobenzyl)-1-methyl4-oxo-6-(tetrahydro-2H-pyran-4-ylmethyl)-1,4-dihydro-pyrido[2,3-c]pyridazine-3-carboxamide;
N-(4-chlorobenzyl)-6-(3-hydroxypropyl)-4-oxo-1,4-dihydropyrido[3,4-c]pyridazine-3-carboxamide;
N-(4-chlorobenzyl)-6-(3-hydroxy-1-propynyl)-4-oxo-1,4-dihydropyrido[3,4-c]-pyridazine-3-carboxamide;
N-(4-chlorobenzyl)-6-(3-hydroxypropyl)-1-methyl-4-oxo-1,4-dihydropyrido[3,4-c]-pyridazine-3-carboxamide;
N-(4-chlorobenzyl)-6-(3-hydroxy-1-propynyl)-1-methyl-4-oxo-1,4-dihydropyrido-[3,4-c]pyridazine-3-carboxamide;
N-(4-chlorobenzyl)-1-methyl-6-(4-morpholinylmethyl)-4-oxo-1,4-dihydropyrido[3,4-c]pyridazine-3-carboxamide;
N-(4-chlorobenzyl)-6-(4-morpholinylmethyl)-4-oxo-1,4-dihydropyrido[3,4-c]-pyridazine-3-carboxamide;
N-(4-chlorobenzyl)-7-(3-hydroxy-1-propynyl)-4-oxo-4H-pyrido[1,2-a]pyrimidine-3-carboxamidePNU;
N-(4-chlorobenzyl)-7-(3-hydroxypropyl)-4-oxo-4H-pyrido[1,2-a]pyrimidine-3-carboxamide;
N-(4-chlorobenzyl)-7-(4-morpholinylmethyl)-4-oxo-4H-pyrido[1,2-a]pyrimidine-3-carboxamide;
N-(4-chlorobenzyl)-4-hydroxy-7-(3-hydroxy-1-propynyl)-2-oxo-2H-pyrido[1,2-a]-pyrimidine-3-carboxamide;
N-(4-chlorobenzyl)-2-hydroxy-7-(3-hydroxypropyl)-4-oxo-4H-pyrido[1,2-a]-pyrimidine-3-carboxamide;
N-(4-chlorobenzyl)-7-(3-hydroxypropyl)4-oxo-4H-pyrazino[1,2-a]pyrimidine-3-carboxamide;
N-(4-chlorobenzyl)-7-(3-hydroxy-1-propynyl)4-oxo-4H-pyrazino[1,2-a]pyrimidine-3-carboxamide;
N-(4-chlorobenzyl)-7-(4-morpholinylmethyl)-4-oxo-4H-pyrazino[1,2-a]pyrimidine-3-carboxamide;
N-(4-chlorobenzyl)-7-(3-hydroxy-1-propynyl)-4-oxo-4H-pyrimido[1,2-b]pyridazine-3-carboxamide;
N-(4-chlorobenzyl)-7-(3-hydroxypropyl)-4-oxo-4H-pyrimido[1,2-b]pyridazine-3-carboxamide;
N-(4-chlorobenzyl)-4-oxo-7-(tetrahydro-2H-pyran-4-ylmethyl)-4H-pyrimido[1,2]-pyridazine-3-carboxamide;
N-(4-chlorobenzyl)-7-(4-morpholinylmethyl)-4-oxo-4H-pyrimido[1,2-b]pyridazine-3-carboxamide;
N-(4-chlorobenzyl)-7-(3-hydroxypropyl)-4-oxo-4H-pyrimido[1,2-a]pyrimidine-3-carboxamide;
N-(4-chlorobenzyl)-7-(3-hydroxy-1-propynyl)-4-oxo-4H-pyrimido[1,2-a]pyrimidine-3-carboxamide;
N-(4-chlorobenzyl)-4-oxo-7-(tetrahydro-2H-pyran-4-ylmethyl)-4H-pyriinido[1,2-a]-pyrimidine-3-carboxamide;
N-(4-chlorobenzyl)-7-(4-morpholinylmethyl)-4-oxo-4H-pyrimido[1,2-a]pyrimidine-3-carboxamide;
N-(4-chlorobenzyl)-2-(3-hydroxypropyl)-8-oxo-8H-pyrimido[1,2-b][1,2,4]triazine-7-carboxamide;
N-(4-chlorobenzyl)-2-(3-hydroxy-1-propynyl)-8-oxo-8H-pyriniido[1,2-b][1,2,4]-triazine-7-carboxamide;
N-(4-chlorobenzyl)-7-(4-morpholinylmethyl)-4-oxo-4H-quinolizine-3-carboxamide;
N-(4-chlorobenzyl)-7-(3-hydroxypropyl)4-oxo-4H-quinolizine-3-carboxamide;
N-(4-chlorobenzyl)-7-(3-hydroxy-1-propynyl)-4-oxo-4H-quinolizine-3-carboxamide;
N-(4-chlorobenzyl)-7-(3-hydroxy-1-propynyl)-4-oxo-4H-pyrido[1,2-a]pyrazine-3-carboxamide;
N-(4-chlorobenzyl)-7-(3-hydroxypropyl)-4-oxo-4H-pyrido[1,2-a]pyrazine-3-carboxamide;
N-(4-chlorobenzyl)-7-(4-morpholinylmethyl)-4-oxo-4H-pyrido[1,2-a]pyrazine-3-carboxamide;
N-(4-chlorobenzyl)-3-(4-morpholinylmethyl)-6-oxo-6H-pyrido[1,2-a]pyrimidine-7-carboxamide;
N-(4-chlorobenzyl)-6-(4-morpholinylmethyl)-4-oxo-4H-chromene-3-carboxamide;
N-(4-chlorobenzyl)-6-(3-hydroxy-1-propynyl)-4-oxo-4H-chromene-3-carboxamide;
N-(4-chlorobenzyl)-6-(((3R)-3-hydroxypyrrolidinyl)methyl)-4-oxo4H-chromene-3-carboxamide;
N-(4-chlorobenzyl)-6,8-bis(4-morpholinylmethyl)-4-oxo4H-chromene-3-carboxamide;
N-(4-chlorobenzyl)-6-(3-hydroxypropyl)-4-oxo-4H-chromene-3-carboxamide;
N-(4-chlorobenzyl)-6-(3-hydroxypropyl)4-oxo-4H-pyrano[2,3-b]pyridine-3-carboxamide;
N-(4-chlorobenzyl)-6-(3-hydroxy-1-propynyl)-4-oxo-4H-pyrano[2,3-b]pyridine-3-carboxamide;
N-(4-chlorobenzyl)-4-oxo-6-(tetrahydro-2H-pyran4-ylmethyl)4H-pyrano[2,3-b]-pyridine-3-carboxamide;
N-(4-chlorobenzyl)-6-(4-morpholinylmethyl)-4-oxo4H-pyrano[2,3-b]pyridine-3-carboxamide;
N-(4-chlorobenzyl)-6-(4-morpholinylmethyl)-4-oxo-4H-thiochromene-3-carboxamide;
N-(4-chlorobenzyl)-6-(3-hydroxypropyl)-4-oxo-4H-thiopyrano[2,3-b]pyridine-3-carboxamide;
N-(4-chlorobenzyl)-6-(3-hydroxy-1-propynyl)-4-oxo-4H-thiopyrano[2,3-b]pyridine-3-carboxamide;
N-(4-chlorobenzyl)-4-oxo-6-(tetrahydro-2H-pyran-4-ylmethyl)-4H-thiopyrano[2,3-b]-pyridine-3-carboxamide;
N-(4-chlorobenzyl)-6-(4-morpholinylmethyl)-4-oxo-4H-thiopyrano[2,3-b]pyridine-3-carboxamide;
N-(4-chlorobenzyl)-6-(3-hydroxy-1-propynyl)4-oxo4H-1,2-benzoxazine-3-carboxamide;
N-(4-chlorobenzyl)-6-(3-hydroxypropyl)-4-oxo-4H-1,2-benzoxazine-3-carboxamide;
N-(4-chlorobenzyl)-6-(4-morpholinylmethyl)-4-oxo4H-1,2-benzoxazine-3-carboxamide;
N-(4-chlorobenzyl)-4-oxo-6-(tetrahydro-2H-pyran4-ylmethyl)-4H-1,2-benzoxazine-3-carboxamide;
N-(4-chlorobenzyl)-6-(3-hydroxy-1-propynyl)-4-oxo4H-1,2-benzthiazine-3-carboxamide;
N-(4-chlorobenzyl)-6-(3-hydroxypropyl)4-oxo-4H-1,2-benzthiazine-3-carboxamide;
N-(4-chlorobenzyl)-6-(4-morpholinylmethyl)-4-oxo-4H-1,2-benzthiazine-3-carboxamide;
N-(4-chlorobenzyl)-4-oxo-6-(tetrahydro-2H-pyran-4-ylmethyl)-4H-1,2-benzthiazine-3-carboxamide;
N-(4-chlorobenzyl)-4-hydroxy-6-(3-hydroxy-1-propynyl)-1-methyl-1H-2,1-benzo-thiazine-3-carboxamide 2,2-dioxide;
N-(4-chlorobenzyl)-4-hydroxy-1-methyl-6-(4-morpholinylmethyl)-1H-2,1-benzo-thiazine-3-carboxamide 2,2-dioxide;
N-(4-chlorobenzyl)-4-methyl-7-(4-morpholinylmethyl)-4H-1,4-benzothiazine-2-carboxamide 1-oxide;
N-(4-chlorobenzyl)-1-methyl-6-(4-morpholinylmethyl)-1H-4,1,2-benzothiadiazine-3-carboxamide 4,4-dioxide;

N-(4-chlorobenzyl)-1-methyl-6-(4-morpholinylmethyl)-1H-thieno[2,3-e][1,3,4]-thiadiazine-3-carboxamide 4,4-dioxide;

N-(4-chlorobenzyl)-6-(4-morpholinylmethyl)-1H-thieno[2,3-e][1,3,4]thiadiazine-3-carboxamide 4,4-dioxide;

N-(4-chlorobenzyl)-6-(3-hydroxypropyl)-1H-thieno[2,3-e][1,3,4]thiadiazine-3-carboxamide 4,4-dioxide;

N-(4-chlorobenzyl)-6-(3-hydroxy-1-propynyl)-1H-thieno[2,3-e][1,3,4]thiadiazine-3-carboxamide 4,4-dioxide;

N-(4-chlorobenzyl)-6-(3-hydroxypropyl)-1-methyl-1H-thieno[2,3-e][1,3,4]-thiadiazine-3-carboxamide 4,4-dioxide;

N-(4-chlorobenzyl)-6-(3-hydroxy-1-propynyl)-1-methyl-1H-thieno[2,3-e][1,3,4]-thiadiazine-3-carboxamide 4,4-dioxide;

N-(4-chlorobenzyl)-6-(3-hydroxypropyl)-1,8-dimethyl-4,7-dioxo-1,4,7,8-tetrahydro [1,8] naphthyridine-3-carboxamide;

N-(4-chlorobenzyl)-6-(3-hydroxy-1-propynyl)-1,8-dimethyl-4,7-dioxo-1,4,7,8-tetrahydro[1,8] naphthyridine-3-carboxamide;

N-(4-chlorobenzyl)-1,8-dimethyl-6-(4-morpholinylmethyl)-4,7-dioxo-1,4,7,8-tetrahydro[1,8]naphthyridine-3-carboxamide;

N-(4-chlorobenzyl)-7-(3-hydroxy-1-propynyl)-4-oxo-4H-pyrido[2,1-c][1,2,4]triazine-3-carboxamide;

N-(4-chlorobenzyl)-7-(3-hydroxypropyl)-4-oxo-4H-pyrido[2,1-c][1,2,4]triazine-3-carboxamide;

N-(4-chlorobenzyl)-7-(4-morpholinylmethyl)-4-oxo4H-pyrido[2,1-c][1,2,4]triazine-3-carboxamide;

N-(4-chlorobenzyl)-4-hydroxy-2-(4-morpholinylmethyl)-1-benzothiophene-5-carboxamide;

N-(4-chlorobenzyl)-4-hydroxy-2-(3-hydroxypropyl)-1-benzothiophene-5-carboxamide;

N-(4-chlorobenzyl)-2-(4-morpholinylmethyl)-5-oxo-5H-[1,3]thiazolo[3,2-a]-pyrimidine-6-carboxamide;

N-(4-chlorobenzyl)-5-hydroxy-2-(4-morpholinylmethyl)-7-oxo-7H-[1,3,4]thiadiazolo-[3,2-a]pyrimidine-6-carboxamide;

N-(4-chlorobenzyl)-4-methyl-2-(4-morpholinylmethyl)-7-oxo-4,7-dihydro[1,3]-thiazolo[5,4-b]pyridine-6-carboxamide;

N-(4-chlorobenzyl)-6-(3-hydroxy-1-propynyl)-1-methyl-4-oxo-1,4-dihydrothieno[2,3-c]pyridazine-3-carboxamide;

N-(4-chlorobenzyl)-6-(3-hydroxypropyl)-1-methyl-4-oxo-1,4-dihydrothieno[2,3-c]-pyridazine-3-carboxamide;

N-(4-chlorobenzyl)-1-methyl-6-(4-morpholinylmethyl)-4-oxo-1,4-dihydrothieno[2,3-c]pyridazine-3-carboxamide;

N-(4-chlorobenzyl)-6-(4-morpholinylmethyl)-4-oxo-1-phenyl-1,4-dihydrothieno[2,3-c]pyridazine-3-carboxamide;

N-(4-chlorobenzyl)-1-methyl-4-oxo-6-(tetrahydro-2H-pyran-4-ylmethyl)-1,4-dihydro-thieno[2,3-c]pyridazine-3-carboxamide;

N-(4-chlorobenzyl)-4-hydroxy-6-(3-hydroxyprop-1-ynyl)-1-methyl-1H-thieno[2,3-c]-[1,2]thiazine-3-carboxamide 2,2-dioxide; and pharmaceutically acceptable salts thereof.

Representative examples of the synthesis of compounds falling within the scope of formulas W1–W22 are as follows.

The following Charts A-BX describe the preparation of the compounds of the present invention. All of the starting materials are prepared by procedures described in these charts or by procedures analogous thereto, which would be well known to one of ordinary skill in organic chemistry. All of the final compounds of the present invention are prepared by procedures described in these charts or by procedures analogous thereto, which would be well known to one of ordinary skill in organic chemistry. All of the variables used in the charts are as defined below or as in the claims.

W1.1. 5-Hydroxy-2-oxo-2H-chromene-6-carboxamides. The preparation of specific examples of heterocycle W1.1 is described in Chart A. Methyl 3,5-dihydroxy-2-oxo-2H-chromene-6-carboxylate A.1 (J. Org. Chem. 1960, 25, 1817) is saponified to afford the corresponding carboxylic acid which is then coupled with a benzylamine (e.g. 4-chlorobenzylamine) mediated by 1,1'-carbonyldiimidazole (or other suitable carboxylic acid activating agent) to provide amides of the general formula A.2. Treatment of A.2 with triflic anhydride provides the enol triflate A.3. Sonogashira coupling of the enol triflate with an electron-rich acetylene (e.g. propargyl alcohol) in either diethylamine or in a mixture of DMF and triethylamine provides alkynyl-substituted derivatives of the general formula A.4. Saturation of the alkyne by hydrogenation catalyzed by palladium on carbon in alcoholic solvents affords alkyl derivatives of the formula A.5.

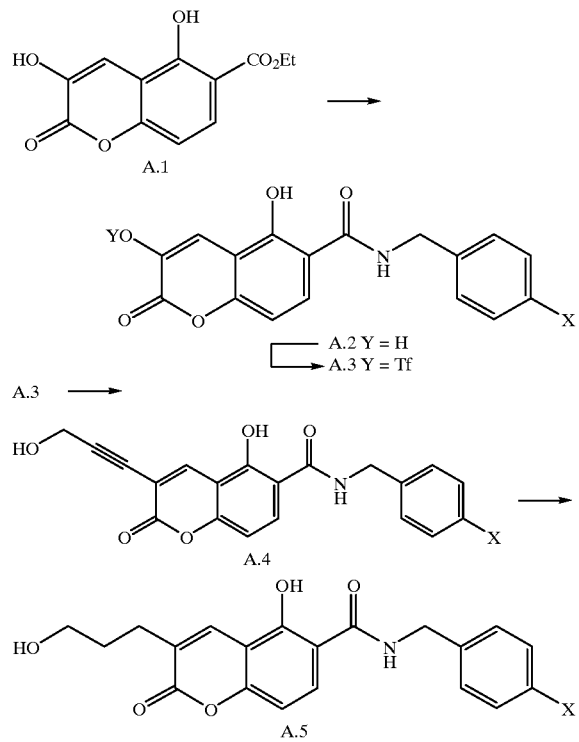

CHART A

Specific examples of heterocycle W 1.1 in which G=$CH_2NR^1R^2$ may be prepared by Chart B and C. Palladium catalyzed carbonylation of aryl triflate A.3 in the presence of tributyltin hydride provides the corresponding aldehyde B.1. Reductive amination with a primary or secondary amine (e.g. morpholine) and sodium cyanoborohydride affords derivatives of the formula B.2. Alternatively as described in Chart C, chloride displacement of 3,8-bis-chloromethyl-5-hydroxy-4-methyl-2-oxo-2H-chromene-6-carboxylate C.1 (J. Indian Chem. Soc. 1961, 38, 975) with a primary or secondary amine (e.g. morpholine) provides a bis-aminomethyl derivative C.2. the resulting ester is then saponified to afford the corresponding carboxylic acid which is then coupled with a benzylamine mediated by 1,1'- carbonyldiimidazole(or other suitable carboxylic acid activating agent) to provide amides of the general formula C.3.

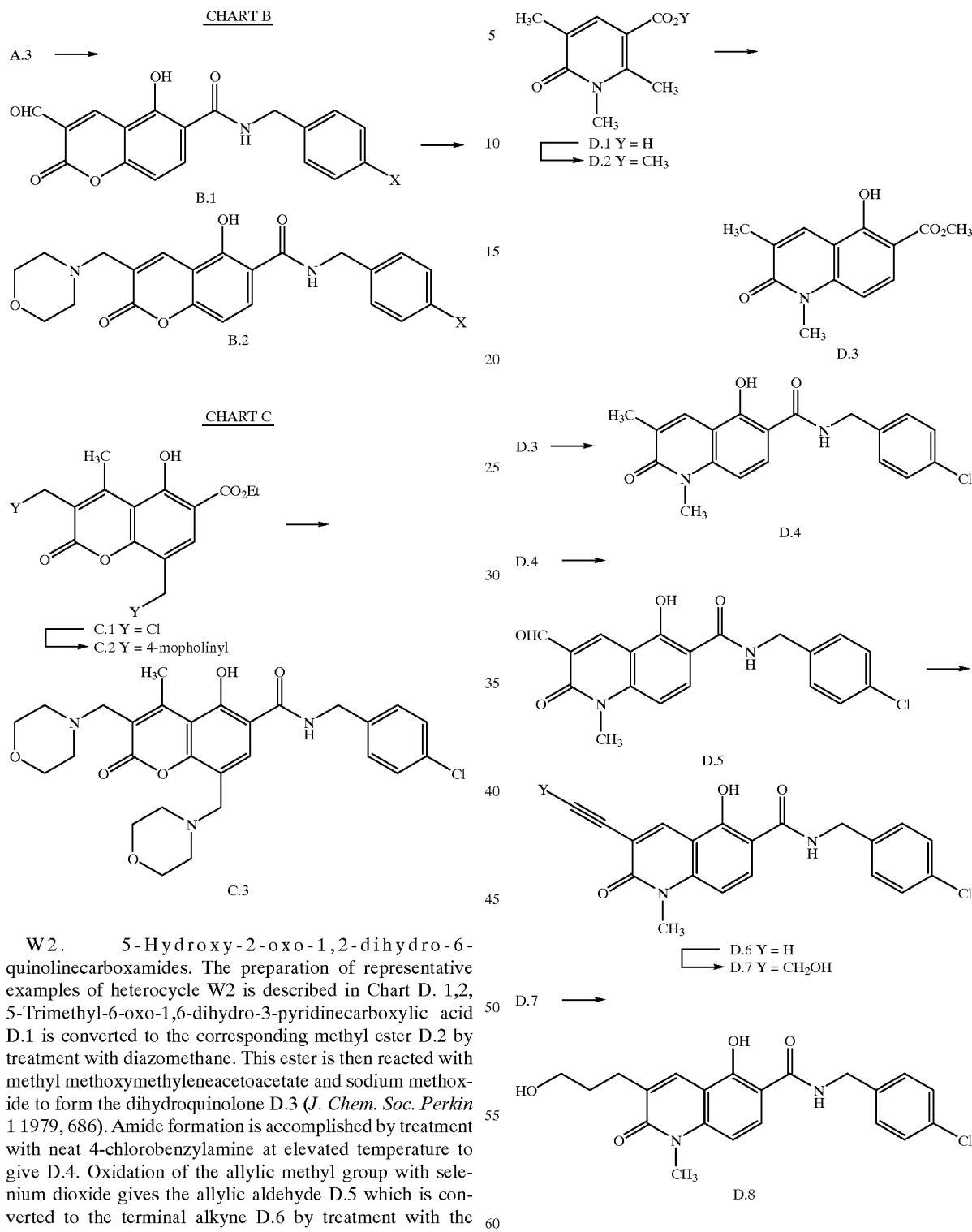

W2. 5-Hydroxy-2-oxo-1,2-dihydro-6-quinolinecarboxamides. The preparation of representative examples of heterocycle W2 is described in Chart D. 1,2,5-Trimethyl-6-oxo-1,6-dihydro-3-pyridinecarboxylic acid D.1 is converted to the corresponding methyl ester D.2 by treatment with diazomethane. This ester is then reacted with methyl methoxymethyleneacetoacetate and sodium methoxide to form the dihydroquinolone D.3 (*J. Chem. Soc. Perkin 1* 1979, 686). Amide formation is accomplished by treatment with neat 4-chlorobenzylamine at elevated temperature to give D.4. Oxidation of the allylic methyl group with selenium dioxide gives the allylic aldehyde D.5 which is converted to the terminal alkyne D.6 by treatment with the modified Wittig reagent, diethyl diazomethylphosphonate. Deprotonation of the alkyne with excess methylmagnesium bromide and trapping of the anion with an aldehyde (e.g. formaldehyde) affords the alkynyl-substituted derivatives of the formula D.7. Saturation of the alkyne by hydrogenation catalyzed by palladium on carbon in alcoholic solvents affords alkyl derivatives D.8.

Alternatively, representative examples of heterocycle W2 wherein $G=CH_2NR^1R^2$ are prepared as described in Chart E. Bromination of the allylic methyl group of D.4 with bromine and AIBN provides the allylic bromide E.1 which can be displaced by amines such as morpholine to form the desired aminomethyl analogs such as E.2.

CHART E

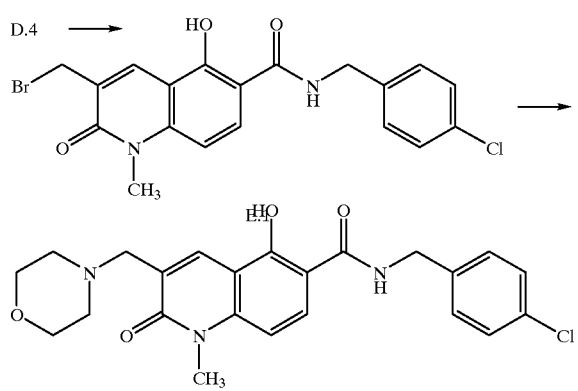

W3.1. 4-Oxo-1,4-dihydro[1,7]naphthyridine-3-carboxamides. The preparation of representative examples of heterocycle W3.1 is described in Chart F. Condensation of 3-aminopyridine-N-oxide F.1 with diethyl ethoxymethylenemalonate followed by cyclization provides 1,7-naphthyridine-3-carboxylate F.2 (*J. Org. Chem.* 1954, 2008). Condensation of the resulting ester with 4-chlorobenzylamine at elevated temperatures provides the corresponding benzyl amide F.3. Reduction of the N-oxide followed by treatment with POBr$_3$ affords 6-bromo-1,7-naphthyridine F.4. Alkylation with iodomethane in the presence of a suitable base provides compound F.5. Sonogashira coupling of F.5 with an electron-rich acetylene (e.g. propargyl alcohol) affords the alkynyl derivatives such as F.6. Saturation of the alkyne by hydrogenation catalyzed by palladium on carbon in alcoholic solvents affords alkyl derivatives such as F.7.

CHART F

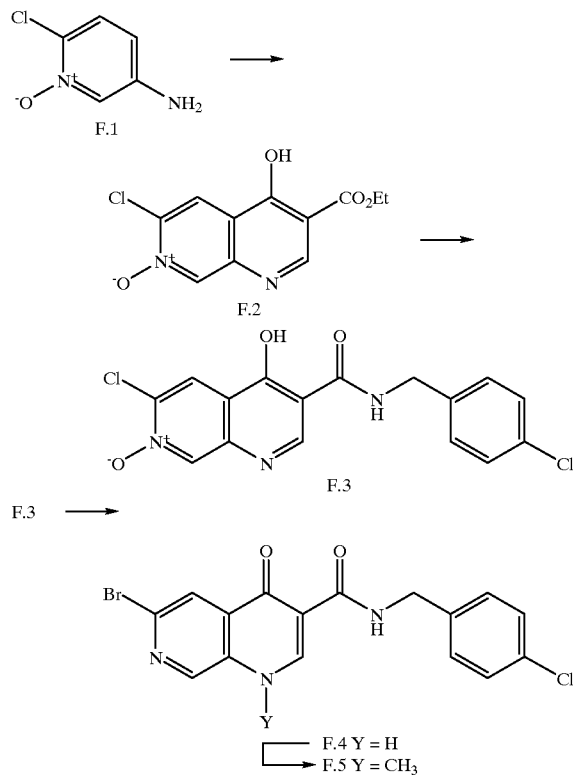

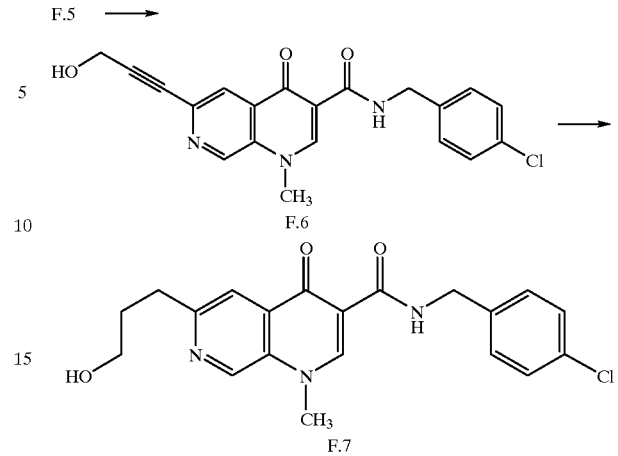

Specific examples of heterocycle W3.1 in which $R^6=OCH_2CH_3$ are prepared as described in Chart G. 3-Amino-6-bromo-2-ethoxypyridine G.1 is condensed with diethyl ethoxymethylenemalonate, and the resulting enamine is cyclized thermally to provide naphthyridine ester G.2. Saponification of the ester followed by coupling of the resulting carboxylic acid with a benzylamine (e.g. 4-chlorobenzylamine) mediated by 1,1'-carbonyldiimidazole (or other suitable carboxylic acid activating agent) provides amides of the general formula G.3. Alkylation of G.3 with iodomethane in the presence of a suitable base affords compounds of the formula G.4. Sonogashira coupling of G.4 with an electron-rich acetylene (e.g. propargyl alcohol) provides alkynyl-derivatives of the formula G.5. Saturation of the alkyne by hydrogenation catalyzed by palladium on carbon in alcoholic solvents affords alkyl derivatives of the formula G.6.

CHART G

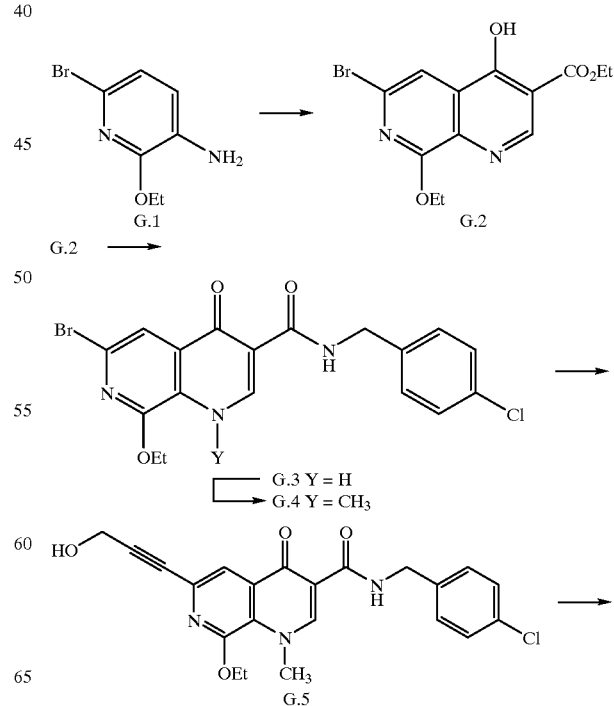

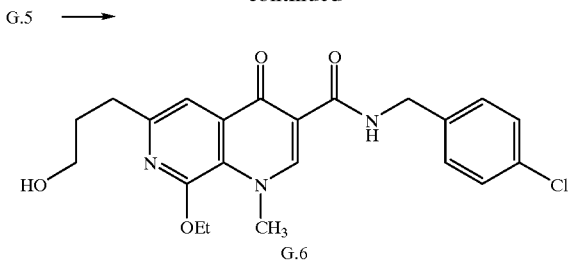

Specific examples of heterocycle W3.1 in which G=CH₂NR¹R² are prepared as described in Chart H. The aryl bromides prepared above in Charts F and G (F.5 and G.4) undergo palladium catalyzed carbonylation in the presence of tributyltin hydride to give the corresponding aldehydes of the formula H.1. Reductive amination with a primary or secondary amine (e.g. morpholine) and sodium cyanoborohydride affords derivatives of the formula H.2.

CHART H

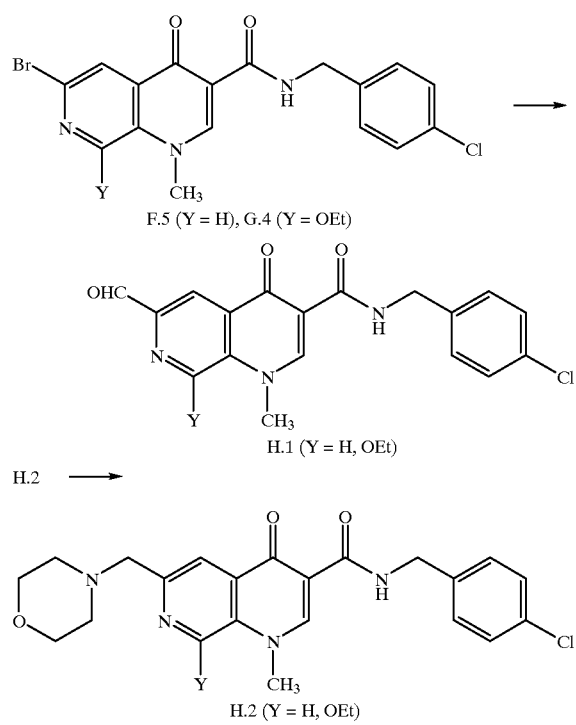

As shown in Chart BT, desired 4-oxo-1,4-dihydro[1,7]naphthyridines are prepared from 2-chloro-6-methylpyridin-3-amine (BT.1, available by the method of B. E. Tomczuk et. al. *J. Med. Chem.*, 1991, 34, 2993–3006). Compound BT.2 is obtained by heating BT.1 in diethyl ethoxymethylenemalonate to 140° C. Cyclization of BT.2 under thermal conditions in a high-boiling solvent such as diphenyl ether or under acid conditions such as by using PPA or Eatons reagent gives BT.3. The naphthyridine product BT.3 thus obtained is alkylated at N-1 with iodomethane (R=CH₃) in DMF with K₂CO₃ at 25° C. or with another suitable alkylating agent to give BT.4 (R=alkyl, substituted alkyl). Compound BT.4 is brominated for example with N-bromosuccinimide initiated by light in a suitable solvent such as dichloroethane to obtain the benzyl bromide BT.5 which is reacted with morpholine to obtain compound of the formula BT.6. Finally, ester BT.6 is reacted with 4-chlorobenzyl-amine, for example with trimethyl aluminum in dichloromethane or via another suitable amide forming route, to give the desired naphthyridines of the formula BT.7. Alternatively as shown in Chart BU, BT.6 is dechlorinated with catalytic palladium on carbon and hydrogen in methanol or another suitable reducing agent to give BU.1 which is treated with 4-chlorobenzylamine, for example with trimethylaluminum in dichloromethane or via another suitable amide forming route, to give desired products BU.2.

Chart BT

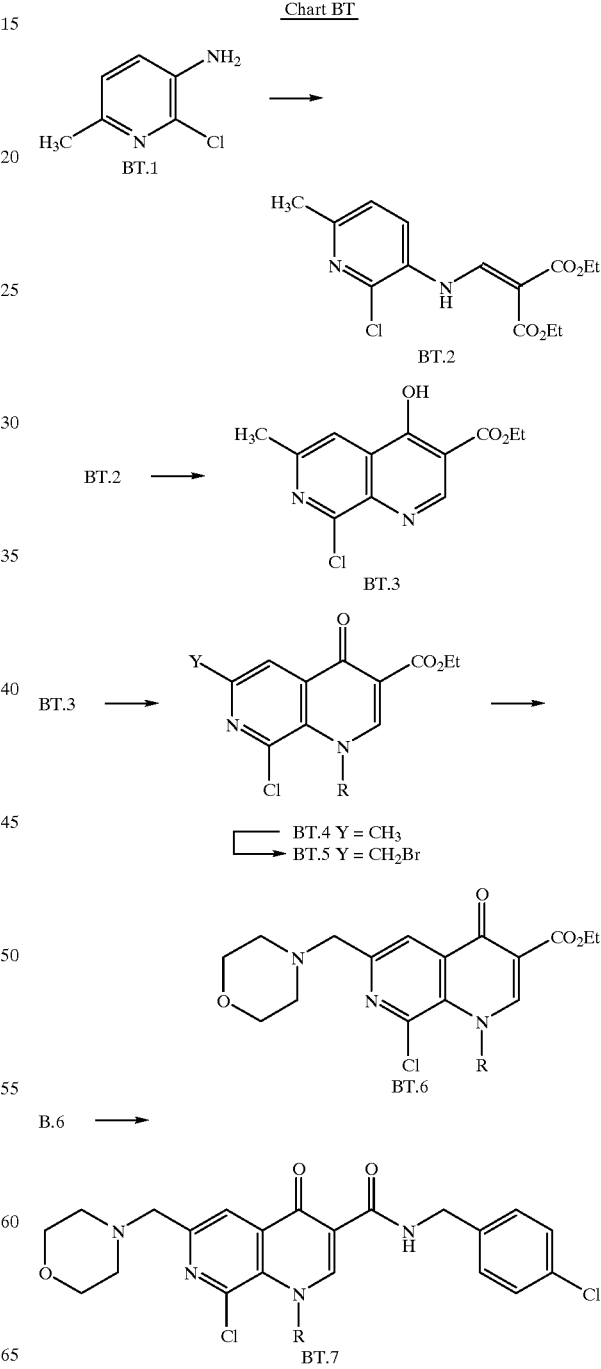

Chart BU

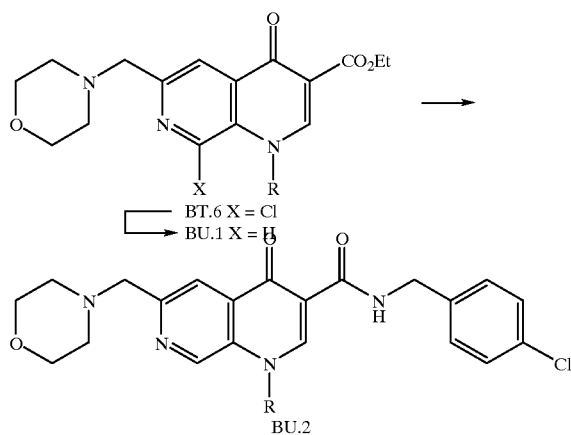

As shown in Chart BV, additional examples of heterocycle W3.1 are prepared from 2,6-dimethyl-3-aminopyridine (BV.1). Compound BV.1 is condensed with diethyl ethoxymethylenemalonate to afford BV.2 which is then cyclized by heating in diphenyl ether to provide BV.3. The naphthyridine product BV.3 is alkylated at N-1 with iodomethane (R=CH$_3$) in DMF with Na$_2$CO$_3$ or with another suitable alkylating agent to give BV.4 (R=alkyl, substituted alkyl). Compound BV.4 is brominated with N-bromosuccinimide initiated by light in a suitable solvent such as dichloroethane to obtain the intermediate bis-benzyl bromide which is reacted with morpholine to obtain compounds of the formula BV.5. Ester BV.5 is treated with a benzylamine (e.g. 4-chlorobenzylamine, 4-bromobenzylamine, or 4-fluorobenzylamine) at high temperature to afford the corresponding amides of the formula BV.6, or alternatively, the ester is saponified to afford the corresponding acid which is then coupled with a benzylamine mediated by 1,1'-carbonyldiimidazole (or other suitable carboxylic acid activating agent) to likewise provide amides of the formula BV.6.

Chart BV

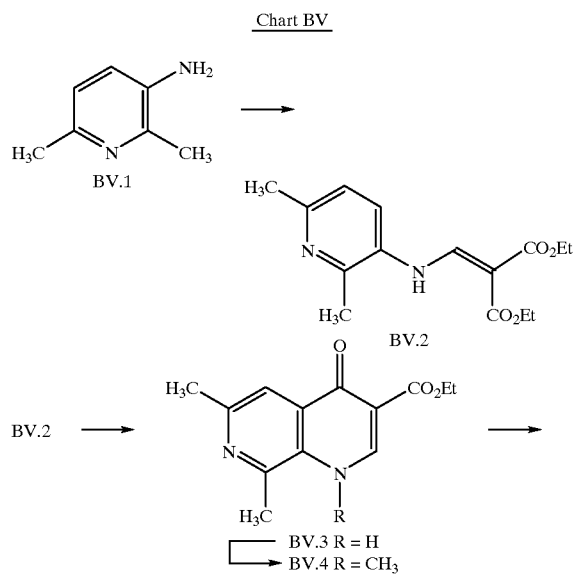

W3.2. 4-Oxo-1,4-dihydro[1,5]naphthyridine-3-carboxamides. Preparation of specific examples of heterocycle W3.2 follows established precedent for [1,5] naphthyridine ring synthesis (U.S. Pat. No. 3,225,055; Eur. J. Med. Chem. 1977, 12, 549; J. Chem. Soc., C. 1954, 2357–2361.), Chart I. The 3-aminopyridines I.1 (Y=tetrahydro-pyranylmethyl, prepared as described in Chart J) is condensed with diethyl ethoxymethylenemalonate to afford the enamine of the formula I.2 (Y=tetrahydropyranyl-methyl). Similarly, the enamine I.2 (Y=chloro) is prepared as described in the literature (J. Heindl et al., Eur. J. Med. Chem. Chim. Ther. 1977, 12, 549–555). Thermal cyclization of these enamines in refluxing diphenyl ether provides the 1,4-dihydro[1,5] naphthyridine-3-esters I.3. The pyridone nitrogen is substituted by a group Z consisting of a substituted or unsubstituted, alkyl or cycloalkyl group by reaction of I.3 in the presence of a base and a species Z-leaving group (e.g. iodomethane) or by the reaction of I.3 with a species ZOH (e.g. methanol) under Mitsunobu conditions (Synthesis 1981, 1.) to afford compounds of the formula I.4.

The resulting ester is then treated with a benzylamine (e.g. 4-chlorobenzylamine, 4-bromobenzylamine, or 4-fluorobenzylamine) at high temperature or, alternatively, ester I.4 is saponified to afford the corresponding acid which is then coupled with a benzylamine mediated by 1,1'-carbonyldiimidazole (or other suitable carboxylic acid activating agent) or, alternatively, ester I.4 may be treated with an above benzylamine and trimethylaluminum in an appropriate solvent to provide amides of the general formula I.5.

CHART I

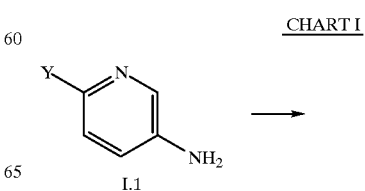

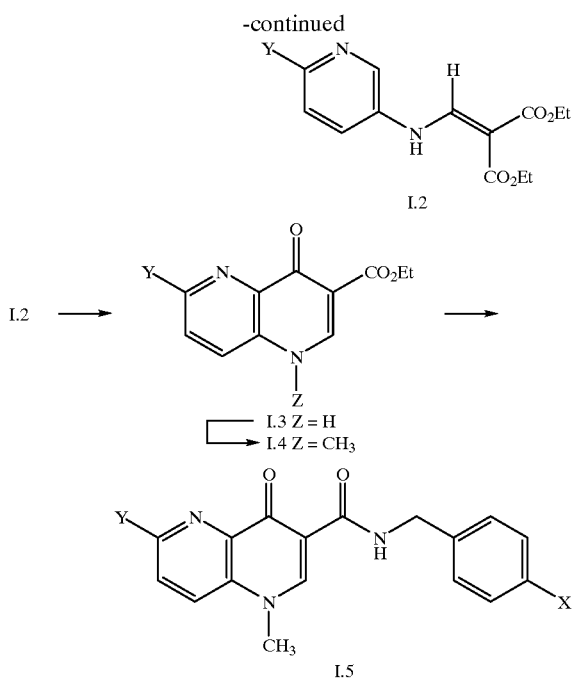

I.1 (Y=4-tetrahydropyranylmethyl) is prepared according to Chart J. Wittig olefination between J.1 and 4-tetrahydropyranylphosphonium bromide (Bestmann, H. J.; Stransky, W.; Vostrowsky, O. *Chem. Ber.* 1979, 109, 1694–1700.) employing sodium hexamethyldisilazide as base provides the olefin J.3. Hydrogenation of J.3 catalyzed by palladium on carbon provides I.1 (Y=4-tetrahydropyranylmethyl).

CHART J

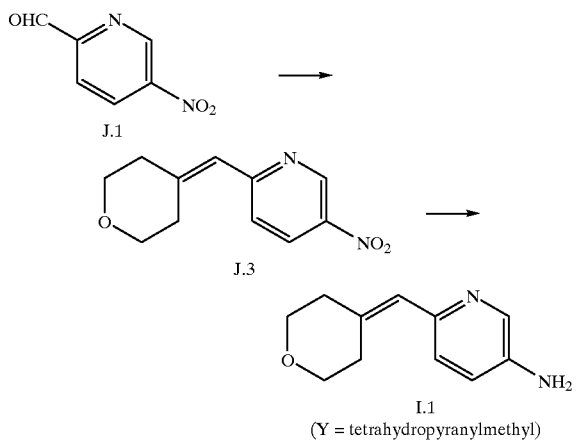

As described in Chart K for the case where Y=chloro (Chart I), the product I.4 (Y=chloro) is further derivatized. Sonogashira coupling of I.4 (Y=chloro) with an electron-rich acetylene (e.g. propargyl alcohol) catalyzed by $PdCl_2$ $(PPh_3)_2$ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) provides the corresponding alkynyl derivatives of formula K.1 (Z=CH$_2$OH). The resulting ester is then treated with a benzylamine (e.g. 4-chlorobenzylamine, 4-bromobenzylamine, or 4-fluorobenzylamine) and trim- ethylaluminum in an appropriate solvent to provide amides of the general formula K.2. Saturation of the alkyne by hydrogenation catalyzed by palladium on carbon in alcoholic solvents affords alkyl derivatives of formula K.3 (Z=CH$_2$OH).

CHART K

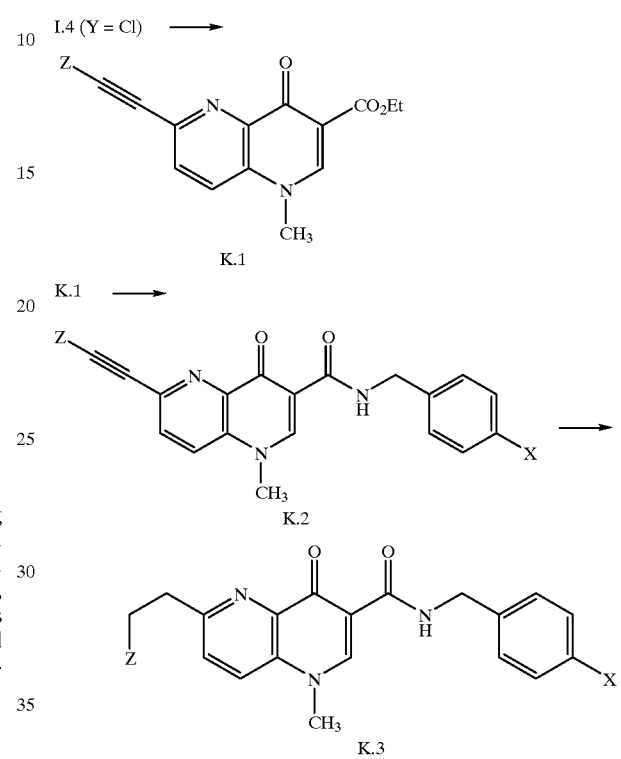

Specific examples of heterocycle W3.2 where G=morpholinylmethyl are prepared as described in Chart L. Reduction of aldehyde L.1 with sodium borohydride followed by reduction of the nitro group via catalytic hydrogenation over platinum affords the amine L.2. Methylation of L.2 by sequential reaction with formic acetic anhydride and borane methyl sulfide complex provides L.3 which is condensed with diethyl ethoxymethylenemalonate to provide the corresponding enamine L.4. Acetylation of L.4 with acetic anhydride affords L.5 which is then cyclized thermally to prepare naphthyridine L.6. Treatment of the resulting ester with a benzylamine (e.g. 4-chlorobenzylamine) at high temperature affords carboxamides of the general formula L.7 with concurrent cleavage of the acetate. The resulting alcohol is treated with methanesulfonyl chloride followed by a primary or secondary amine (e.g. morpholine) to afford compounds of the formula L.8.

CHART L

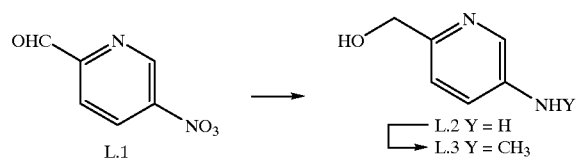

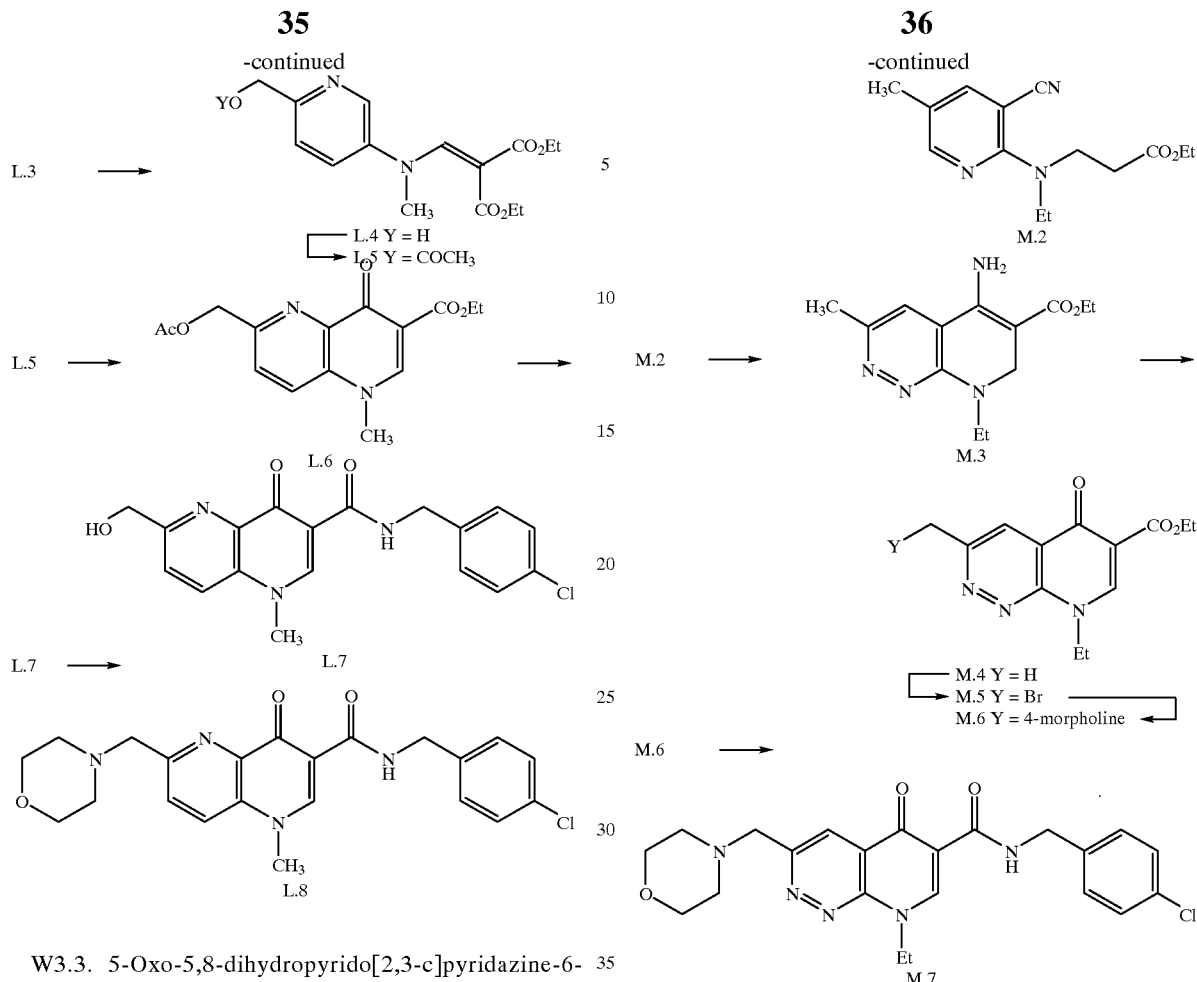

W3.3. 5-Oxo-5,8-dihydropyrido[2,3-c]pyridazine-6-carboxamides. Preparation of specific examples of heterocycle W3.3 follows an established precedent for pyrido[2,3-c]pyridazine ring synthesis (G. Heinisch Arch. Pharm. 1990, 323, 207 –210.), Chart M. 2-Chloro-5-methylnicotinonitrile M.1 (Chem. Ber. 1964, 97, 3349) is heated with ethyl 3-ethylaminopropionate in the presence of a base (e.g. sodium bicarbonate) to afford pyridylamine M.2. Compound M.2 cyclizes to afford the bicycle M.3 upon treatment with sodium ethoxide which upon acid hydrolysis affords the pyridopyridazine M.4. Allylic bromination of M.4 employing conditions such as N-bromosuccinimide and AIBN provides the alkylhalide M.5 which is then displaced with a primary or secondary amine (e.g. morpholine) to afford a compound such as M.6. The resulting ester M.6 is then treated with a benzylamine (e.g. 4-chlorobenzylamine, 4-bromobenzylamine, or 4-fluorobenzylamine) at high temperature to afford the corresponding amides of the general formula M.7 or ester M.6 is saponified to afford the corresponding acid which is then coupled with a benzylamine mediated by 1,1'-carbonyldiimidazole (or other suitable carboxylic acid activating agent) to provide amides of the general formula M.7.

CHART M

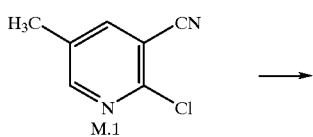

W3.4. 8-Oxo-5,8-dihydropyrido[3,2-d]pyrimidine-7-carboxamide. Preparation of specific examples of heterocycle W3.4 follows an established literature precedent described in Chart N (U.S. Pat. No. 3,320,257 and J. Chem. Soc. C. 1967, 1745.). Heteroarylamine N.1 is condensed with diethyl ethoxymethylenemalonate to afford the enamine N.2. Cyclization of N.2 is effected by heating the enamine in diethylphthalate to provide bicycle N.3. The resulting ester N.3 is then saponified to afford the corresponding carboxylic acid N.4 which is then coupled with a benzylamine (e.g. 4-chlorobenzylamine, 4-bromobenzylamine, or 4-fluorobenzylamine) mediated by 1,1'-carbonyldiimidazole (or other suitable carboxylic acid activating agent) to provide amides of the general formula N.5. The pyridone nitrogen is then substituted by a group Z consisting of a substituted or unsubstituted, alkyl or cycloalkyl group by reaction of N.5 in the presence of a base and a species Z-leaving group (e.g. iodomethane) or by the reaction of N.5 with a species ZOH (e.g. methanol) under Mitsunobu conditions (Synthesis 1981, 1.) to afford compounds of the formula N.6. Sonogashira coupling of N.6 with an electron-rich acetylene (e.g. propargyl alcohol) catalyzed by $PdCl_2(PPh_3)_2$ and copper(I) iodide either in diethylamine (Sonogashira, K.; Tohada, Y.; Hagihara, N. Tetrahedron Lett. 1975, 50, 4467.) or in a mixture of DMF and triethylamine (Fisher, M. J. et. al. J. Med. Chem. 1997, 40, 2085.) provides the corresponding alkynyl derivatives of formula N.7 (Z=$CH_2OH$). Saturation of the alkyne by hydrogenation catalyzed by palladium on carbon in alcoholic solvents affords alkyl derivatives of formula N.8 (Z=$CH_2OH$).

CHART N

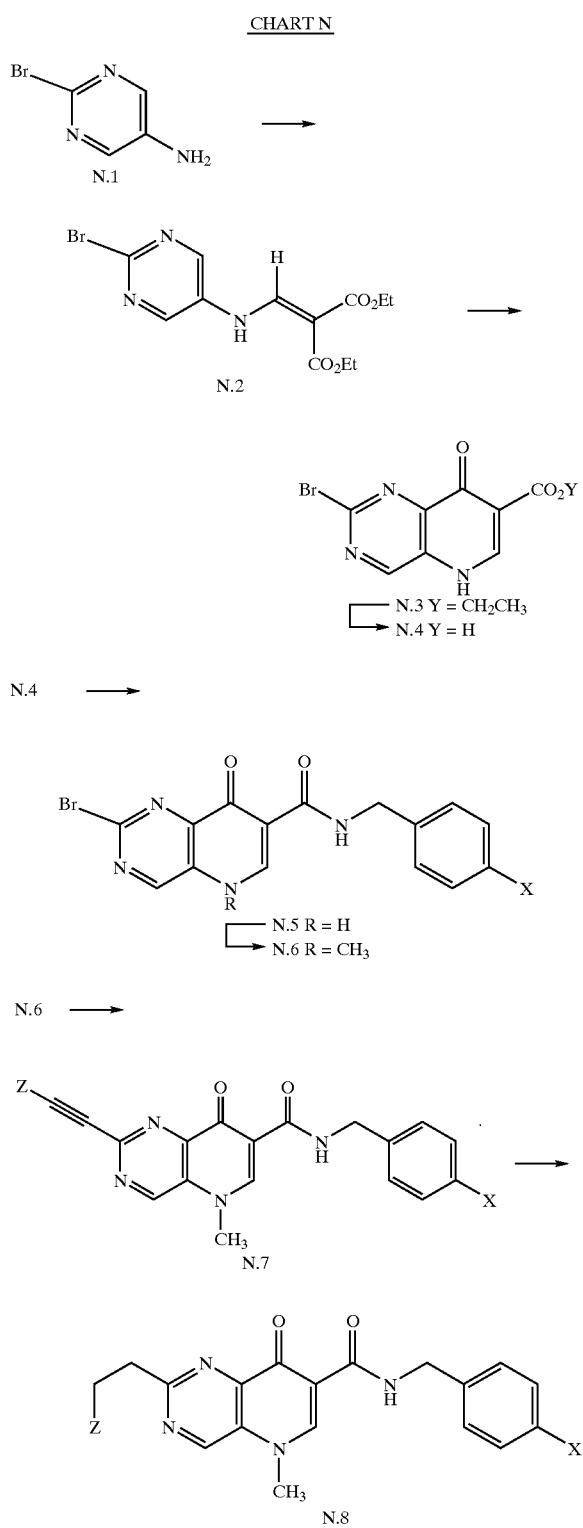

Alternatively, derivatives where G is specified as $C_{1-4}$alkyl substituted by $NR^1R^2$ (e. g. 4-morpholinomethyl) are prepared from N.5 as described in Chart O. Compounds of the formula N.5 undergo palladium catalyzed carbon monoxide insertion and trapping with methanol to afford methyl esters of the formula O.1. The resulting esters are reduced with lithium aluminum hydride or other suitable reducing agent to provide the corresponding alcohols of the formula O.2. Alkylation of the pyridone nitrogen is accomplished as described above to afford compounds of the formula O.3. Activation of the alcohol as the mesylate by reaction with methanesulfonyl chloride in the presence of an amine base (e.g. collidine) followed by displacement with a primary or secondary amine ($HNR^1R^2$ such as morpholine) provides compounds of the formula O.4.

CHART O

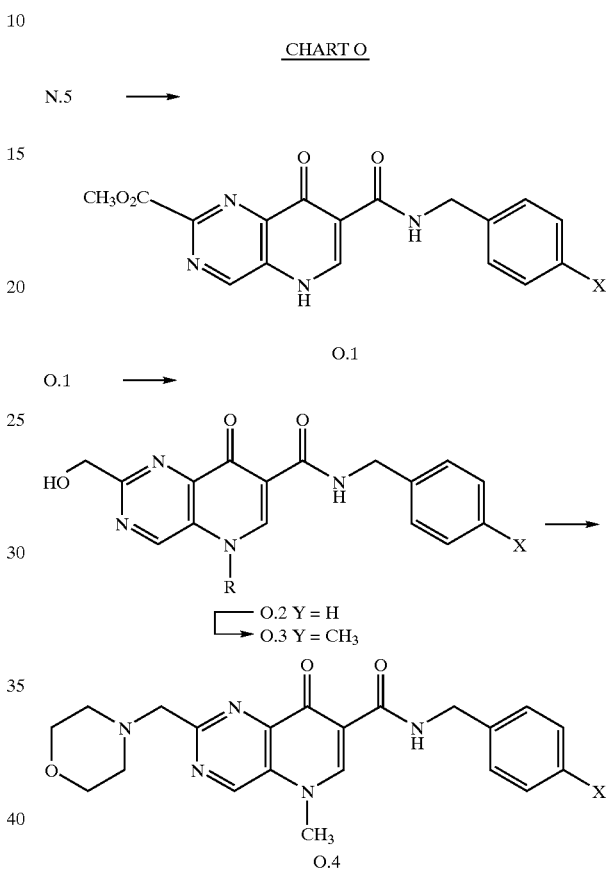

W4.1. 4-Oxo-1,4-dihydropyrido[2,3-c]pyridazine-3-carboxamides. Preparation of specific examples of heterocycle W4. 1 follows an established literature precedent described in Chart P-Q (*J. Heterocyclic Chem.* 197, 24, 55.; *Chem. Pharm. Bull.* 1990, 38, 3211.; and *Chem. Pharm. Bull.* 1990, 38, 3359.). As described in Chart P. diazotization of β-ketoesters P.1 (prepared as described in Chart S, where Y=4-morpholiylmethyl; Chart T, where Y=4-tetrahydropyranylmethyl; and Chart U. where Y=iodo) with tosyl azide. Reductive cyclization of P.2 with triphenyphosphine affords the pyridopyridazine P.3. The ring nitrogen atom of compound P.3 may then be optionally substituted by a group R inclusive to the group $R^7$ consisting of a substituted or unsubstituted, alkyl or cycloalkyl group by reaction of P.3 in the presence of a base and a species R-leaving group (e.g. iodomethane) or by the reaction of P.3 with a species ZOH (e.g. methanol) under Mitsunobu conditions (*Synthesis* 1981, 1.) to afford compounds of the formula P.4. Esters P.3 or P.4 are then treated with a benzylamine (e.g. 4chlorobenzylamine, 4-bromobenzyladmine, or 4-fluorobenzylamine) at high temperature to afford the corresponding amides of the general formula P.5, or alternatively, the ester is saponified to afford the corresponding acid which is then coupled with a benzylamine mediated by 1,1'-carbonyldiimidazole (or other suitable carboxylic acid activating agent) to likewise provide amides of the general formula P.5.

CHART P

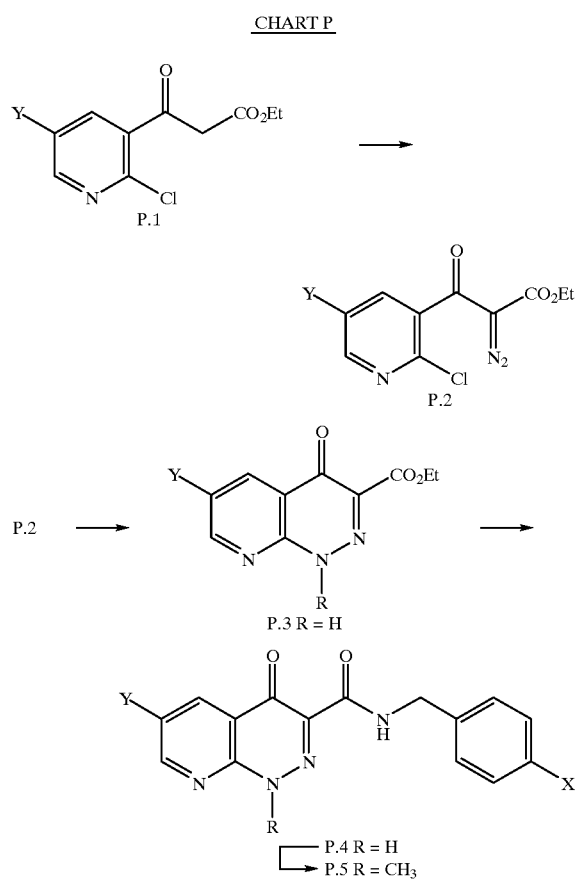

In another aspect, specific examples of heterocycle W4.1 in which $R^7$=aryl or het are prepared as described in Chart Q. Treatment of compounds of the formula P.1 with an aryl- or heteroaryldiazonium chloride affords the hydrazone Q.1. Hydrazone Q.1 cyclizes to afford the pyridopyridazine Q.2 upon treatment with an appropriate base (e.g. potassium carbonate). The resulting ester may be transformed to the corresponding carboxamides of the general formula Q.3 in a similar fashion to that described in Chart P.

CHART Q

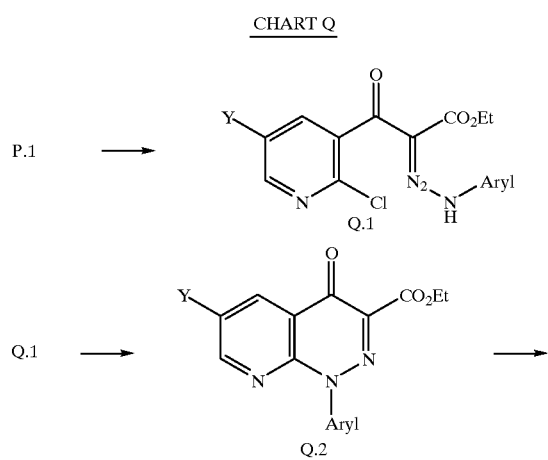

-continued

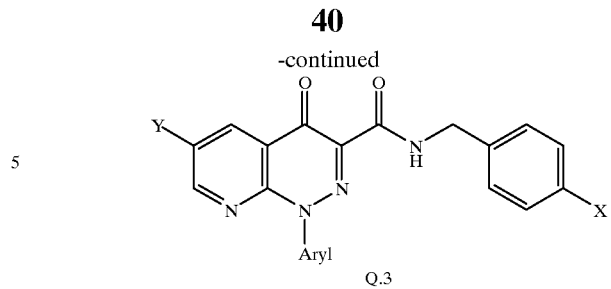

As specified in Chart P and Chart Q, when Y=iodo, intermediates P.5 or Q.3 may be further elaborated to provide specific examples of heterocycle W4.1 where G=3-hydroxypropyl or 3-hydroxy-1-propynyl as described in Chart R. Intermediates P.5 and Q.3 undergo Sonogashira coupling with an electron-rich acetylene (e.g. propargyl alcohol, Z=CH$_2$OH) catalyzed by PdCl$_2$(PPh$_3$)$_2$ and copper (I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) provides the corresponding alkynyl derivatives of formula R.1 (Z=CH$_2$OH). Saturation of the alkyne by hydrogenation catalyzed by palladium on carbon in alcoholic solvents affords alkyl derivatives of formula R.2 (Z=CH$_2$OH).

CHART R

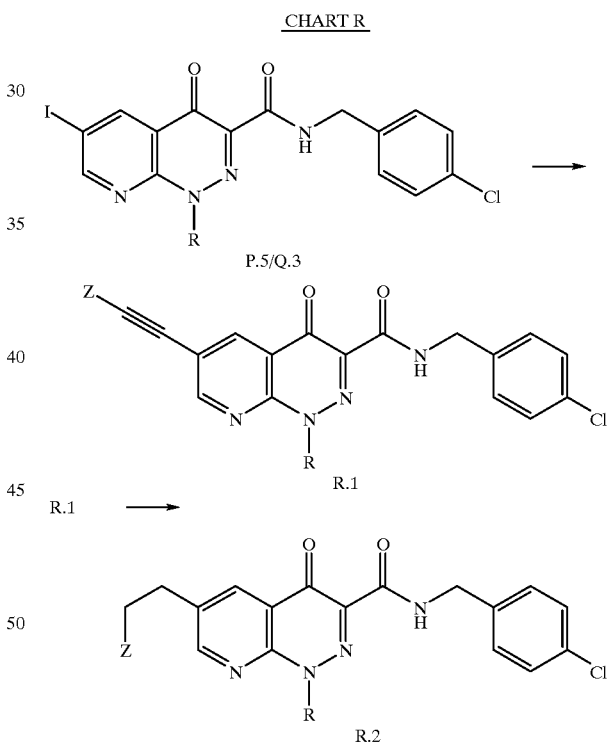

P.1 (Y=morpholinylmethyl) is prepared according to Chart S. Reductive amination of 5-bromo-6-chloronicotinaldehyde S.1 (U.S. Pat. No. 4,317,913) with morpholine, acetic acid, and sodium triacetoxyborohydride provides the benzylmorpholine S.2. Metal-halogen exchange between n-butyllithium and S.2 at −70° C. in tetrahydrofuran followed by addition of the resulting aryl lithium to N-methoxy-N-methylacetamide yields the methylketone S.3. Treatment of S.3 with a base such as sodium hydride in the presence diethylcarbonate affords the β-ketoester P.1 (Y=morpholinylmethyl) which may then be employed as in Chart P.

CHART S

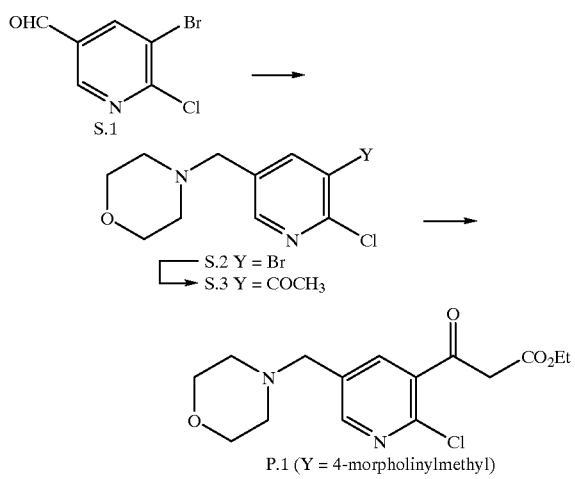

P.1 (Y = 4-morpholinylmethyl)

P.1 (Y=4-tetrahydropyranylmethyl) is prepared according to Chart T. Wittig olefination between S.1 and 4-tetrahydropyranylphosphonium bromide (Bestmann, H. J.; Stransky, W.; Vostrowsky, O. *Chem. Ber.* 1979, 109, 1694–1700.) employing sodium hexamethyldisilazide as base provides the olefin T.1. Metal-halogen exchange between n-butyllithium and T.1 at −70° C. in tetrahydrofuran followed by addition of the resulting heteroaryl lithium to carbon dioxide yields the carboxylic acid T.2. Saturation of the olefin by hydrogenation of T.2 employing palladium on carbon as catalyst affords T.3. Conversion of T.3 to its corresponding imidazolide with 1,1'-carbonyldiimidazole followed by treatment with the trimethylsilyl ester of ethyl hydrogen malonate in the presence of DBU (Wang, X.; Monte, W. T.; Napier J. J.; Ghannam, A. *Tetrahedron Lett.* 1994, 35, 9323–9326) provides β-ketoester P.1 (Y=4-tetrahydropyranylmethyl) which may be employed as in Chart P.

CHART T

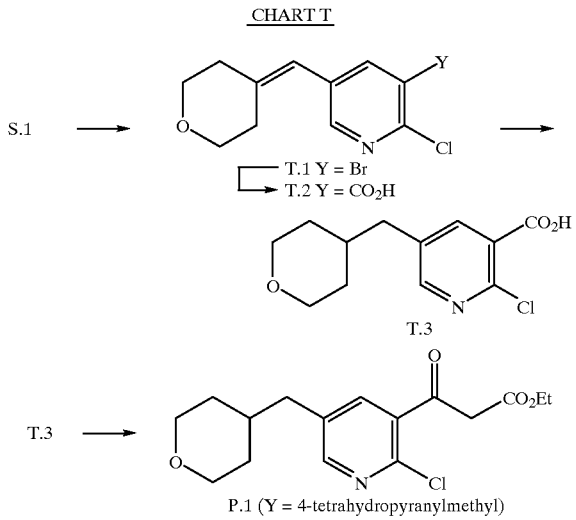

P.1 (Y = 4-tetrahydropyranylmethyl)

P.1 (W=iodo) is prepared according to Chart U. Conversion of 2-chloro-5-iodonicotinic acid U.1 (*J. Chem. Eng. Data* 1976, 21, 246.) to its corresponding imidazolide with 1,1'-carbonyldiimidazole followed by treatment with the trimethylsilyl ester of ethyl hydrogen malonate in the presence of DBU (Wang, X.; Monte, W. T.; Napier J. J.; Ghannam, A. *Tetrahedron Lett.* 1994, 35, 9323–9326) provides β-ketoester P.1 (W=iodo) which may be employed as in Chart P.

CHART U

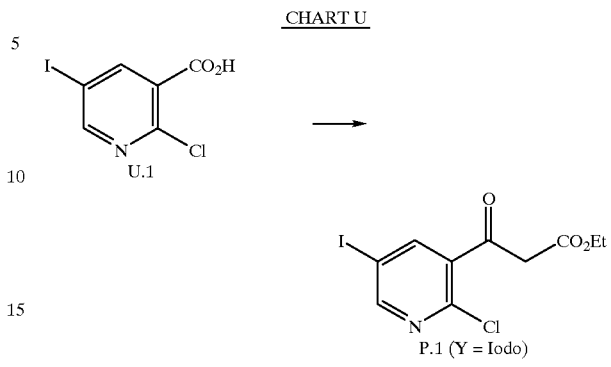

P.1 (Y = Iodo)

W4.2. 4-Oxo-1,4-dihydropyrido[3,4-c]pyridazine-3-carboxamides. Specific examples of heterocycle W4.2 where G=3-hydroxypropyl or 3-hydroxy-1-propynyl are prepared as described in Chart V. Treatment of V.1 with bromine and aqueous sodium hydroxide according to the procedure of Moss et. al. (*Tetrahedron Letters* 1993, 34, 6225–6228) affords the amino acid V.2. This material is then treated with di-t-butyldicarbonate in an appropriate solvent such as THF, MeOH, DMF or mixtures thereof with a base such as triethylamine or sodium bicarbonate to give the t-butylcarbamate V.3. Treatment of V.3 with carbonyldiimidazole or another suitable acid-activating agent followed by the addition of ethyl trimethylsilylmalonate and 1,8-diazabicyclo[5.4.0]undec-7-ene (DBU) in a suitable solvent such as acetonitrile provides the ester V.4. Removal of the t-butylcarbamate protecting group by well known methods (trifluoroacetic acid in dichloromethane or hydrochloric acid in a solvent such as dioxane, ether or THF) affords the aniline V.5. Treatment of V.5 with sodium nitrite in aqueous acid yields the cyclized intermediate V.6. Heating this material in the presence of 4-chlorobenzylamine affords the amide V.7. Treatment with bromine in carbon tetrachloride provides the bromide V.8 which can then be coupled to an electron-rich acetylene (e.g. propargyl alcohol, Z=CH$_2$OH) catalyzed by PdCl$_2$(PPh$_3$)$_2$ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) to provide the corresponding alkynyl derivatives of formula V.9 (Z=CH$_2$OH). The nitrogen can then be alkylated with alkyl halides (e.g. iodomethane) and a suitable base by well known methods to give V.10. Saturation of the alkyne precursor V.9 by hydrogenation catalyzed by palladium on carbon in alcoholic solvents affords alkyl derivatives of formula V.11 (Z=CH$_2$OH). Alkylation of nitrogen as described above provides compounds of the formula V.12.

Chart V

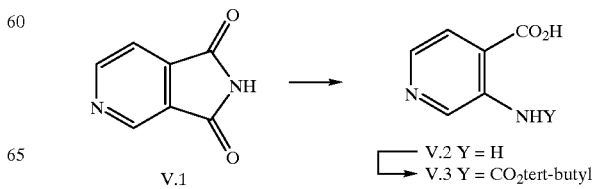

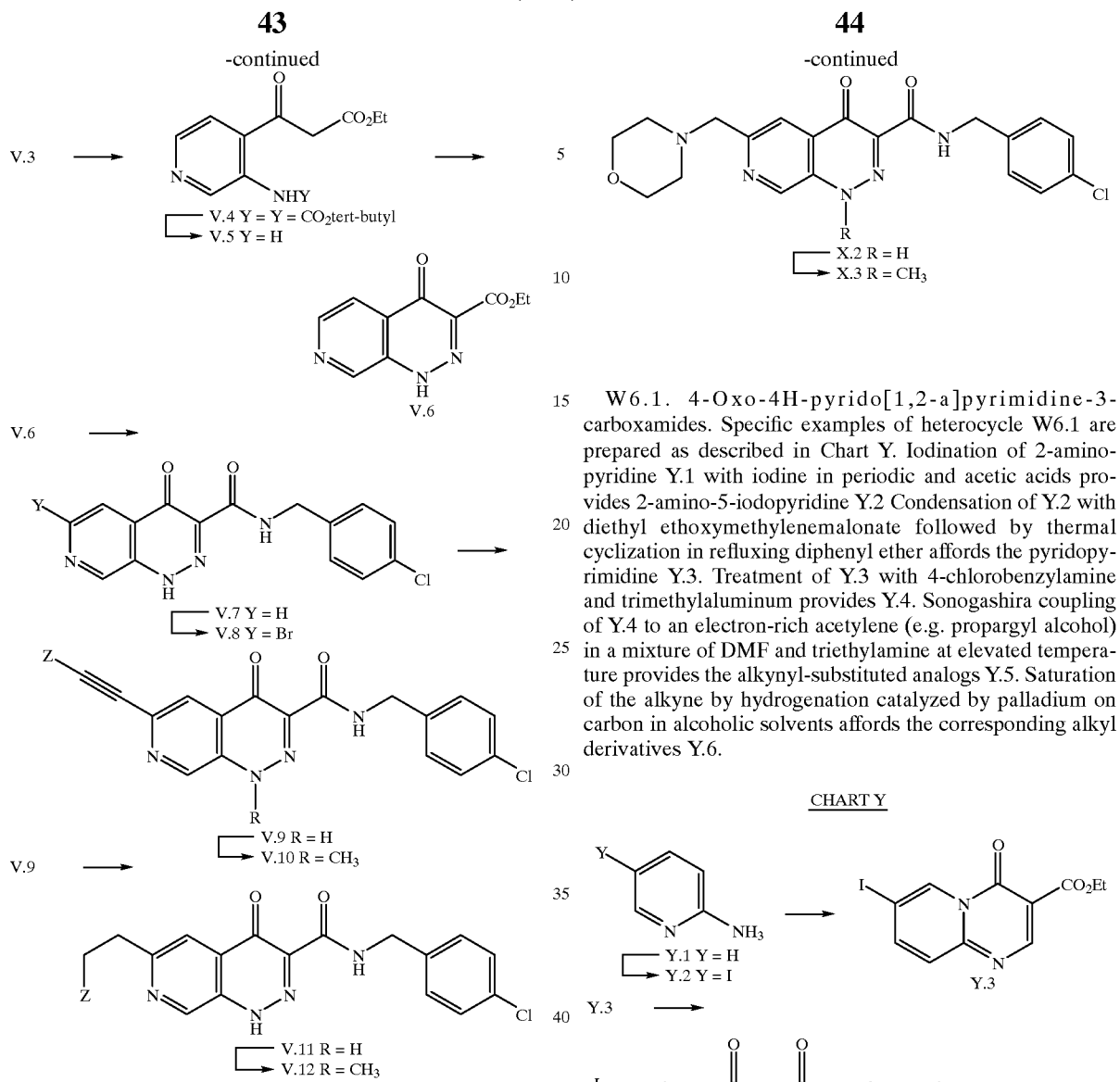

W6.1. 4-Oxo-4H-pyrido[1,2-a]pyrimidine-3-carboxamides. Specific examples of heterocycle W6.1 are prepared as described in Chart Y. Iodination of 2-aminopyridine Y.1 with iodine in periodic and acetic acids provides 2-amino-5-iodopyridine Y.2 Condensation of Y.2 with diethyl ethoxymethylenemalonate followed by thermal cyclization in refluxing diphenyl ether affords the pyridopyrimidine Y.3. Treatment of Y.3 with 4-chlorobenzylamine and trimethylaluminum provides Y.4. Sonogashira coupling of Y.4 to an electron-rich acetylene (e.g. propargyl alcohol) in a mixture of DMF and triethylamine at elevated temperature provides the alkynyl-substituted analogs Y.5. Saturation of the alkyne by hydrogenation catalyzed by palladium on carbon in alcoholic solvents affords the corresponding alkyl derivatives Y.6.

Specific examples of heterocycle W4.2 where G=CH$_2$NR$^1$R$^2$ are prepared as described in Chart X. Bromide V.8 is formylated with PdCl$_2$(PPh$_3$)$_2$, carbon monoxide, and sodium formate in DMF to afford carboxaldehyde X.1 according to the procedure of Okano (*Bull. Chem. Soc. Jpn.* 1994, 67, 2329.). This material is then subjected to reductive amination conditions with a primary or secondary amine (e.g. morpholine) to provide compounds of the formula X.2 which are then alkylated at nitrogen as described above to yield X.3.

Chart X

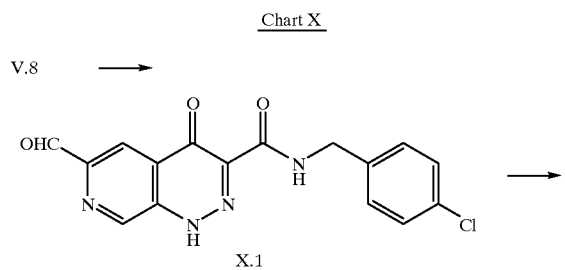

In another aspect, specific examples of heterocycle W6. 1 in which G=CH$_2$NR$^1$R$^2$ are prepared as described in Chart Z. Palladium mediated carbonylation of aryl iodide Z.4 in the presence of tributyltin hydride provides the aldehyde Z.1. Reductive amination with a primary or secondary amine (e.g. morpholine) and sodium cyano-borohydride provides derivatives of the formula Z.2.

CHART Z

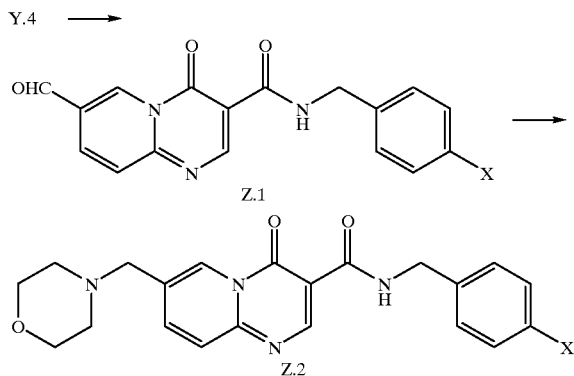

A specific example of heterocycle W6.1 in which $R^8$=OH is prepared as described in Chart AA. Sonogashira coupling of iodopyridine Y.2 with 2-(2-propynyloxy)-tetrahydro-2H-pyran affords the alkyne AA.1 which is condensed with diethyl 2-(((4-chlorobenzyl)amino)carbonyl)malonate (prepared by the reaction of 4-chlorobenzyl-amine with triethyl methanetricarboxylate) to afford the pyridopyrimidine AA.2. Deprotection of the tetrahydropyanyl protecting group in acidic methanol provides compounds of the formula AA.3. Saturation of the alkyne by hydrogenation catalyzed by palladium on carbon in alcoholic solvents affords alkyl derivatives of formula AA.4.

CHART AA

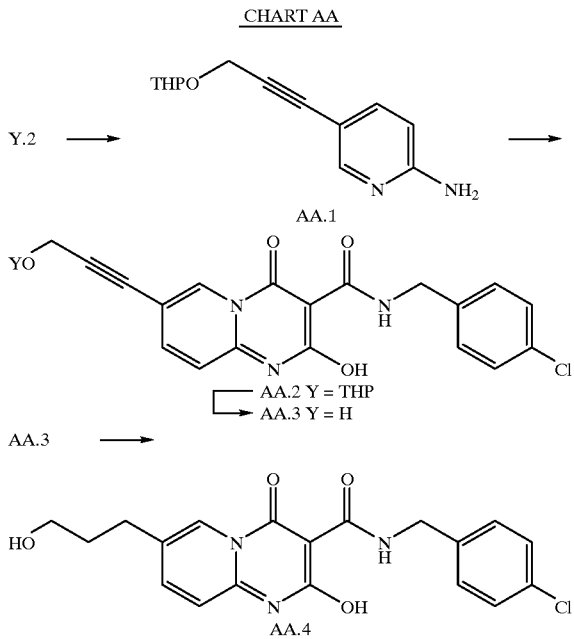

W6.2. 4-Oxo-4H-pyrazino[1,2-a]pyrimidine-3-carboxamides. The preparation of specific examples to heterocycle W6.2 in which G=3-hydroxypropyl or 3-hydroxy-1-propynyl is described in Chart AB. 5-Bromopyrazine AB.1, is condensed with diethyl ethoxymethylenemalonate, and the resulting enamine is cyclized thermally in refluxing diphenyl ether to afford the pyrazinopyrimidine ester AB.2. The resulting ester is then reacted with a benzylamine (e.g. 4-chlorobenzylamine) at high temperature to give carboxamides of the formula AB.3. Sonogashira coupling between AB.3 and an electron-rich acetylene (e.g. propargyl alcohol) provides alkynyl derivatives of the formula AB.4. Saturation of the alkyne by hydrogenation catalyzed by palladium on carbon in alcoholic solvents affords the corresponding alkyl derivatives AB.5.

CHART AB

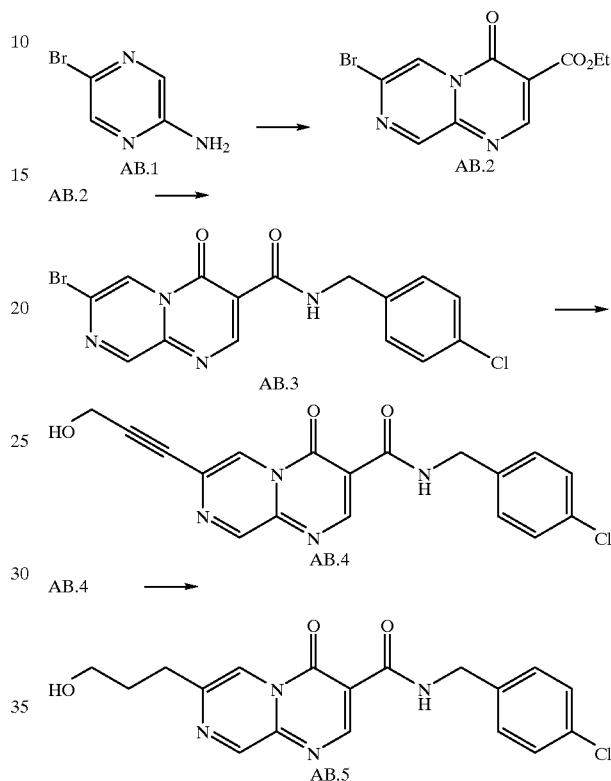

Specific examples of heterocycle W6.2 in which G=CH$_2$NR$^1$R$^2$ are prepared as described in Chart AC. Methyl 5-amino-2-pyrazinecarboxylate AC.1 (*Helv. Chim. Acta.* 1964, 47, 873) is reduced by treatment with sodium borohydride in methanol/water (U.S. Pat. No. 4,267,327) to afford alcohol AC.2. Condensation of AC.2 with diethyl ethoxymethylenemalonate, followed by acylation of the free alcohol with acetic anhydride in acetic acid provides AC.3. Thermal cyclization of AC.3 affords the pyrazinopyriridine ester AC.4. The resulting ester AC.4 is then reacted with a benzylamine (e.g. 4-chlorobenzylamine) at high temperature to provide carboxamides of the general formula AC.5 with concurrent cleavage of the acetate. Activation of the hydroxy group as the corresponding mesylate by reaction with methanesulfonyl chloride in the presence of a suitable base followed by nucleophilic displacement by a primary or secondary amine (e.g. morpholine) affords derivatives such as AC.6.

CHART AC

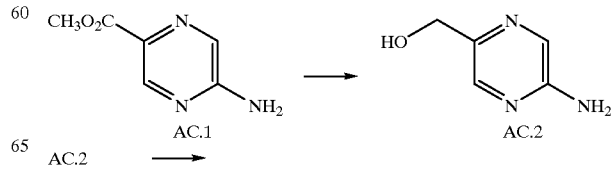

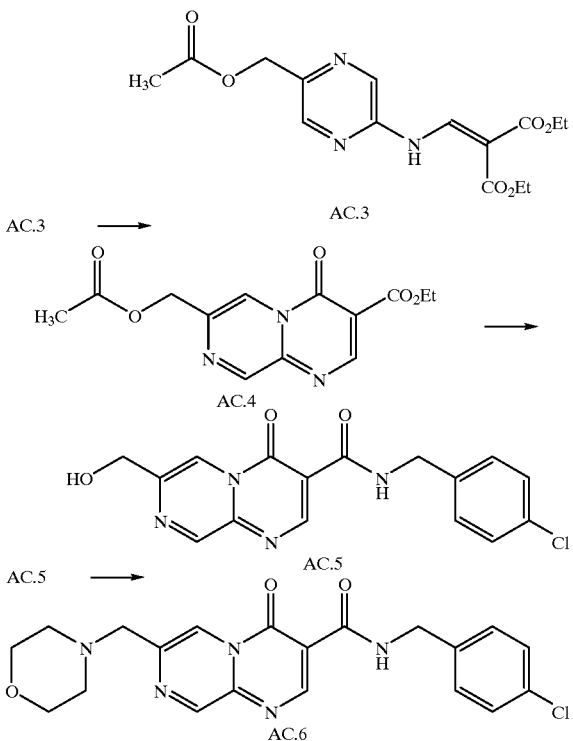

W6.3. 4-Oxo-4H-pyrimido[1,2-b]pyridazine-3-carboxamide. Preparation of specific examples of heterocycle W6.3 follows an established literature precedent described in Chart AD (*J. Org. Chem.* 1971, 36, 2457 and U.S. Pat. No. 4,231,928). Heterocyclic amine AD.1 (*Aust. J. Chem.* 1997, 50, 61–67.) is condensed with diethyl ethoxymethylenemalonate to afford enamine AD.2. Cyclization of the resulting enamine by heating in polyphoric acid (PPA) provides pyrimidopyridazine AD.3. The resulting ester AD.3 is then saponified to afford the corresponding carboxylic acid AD.4 which is then coupled with a benzylamine (e.g. 4-chlorobenzylamine, 4-bromobenzylamine, or 4-fluorobenzylamine) mediated by 1,1'-carbonyldiimidazole (or other suitable carboxylic acid activating agent) to provide amides of the general formula AD.5. To prepare derivatives where G=3-hydroxypropyl or 3-hydroxy-1-propynyl, intermediate AD.5 may be further elaborated by Sonogashira coupling with an electron-rich acetylene (e.g. propargyl alcohol, Z=CH$_2$OH) catalyzed by PdCl$_2$(PPh$_3$)$_2$ and copper (I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) provides the corresponding alkynyl derivatives of formula AD.6 (Z=CH$_2$OH). Saturation of the alkyne by hydrogenation catalyzed by palladium on carbon in alcoholic solvents affords alkyl derivatives of formula AD.7 (Z=CH$_2$OH).

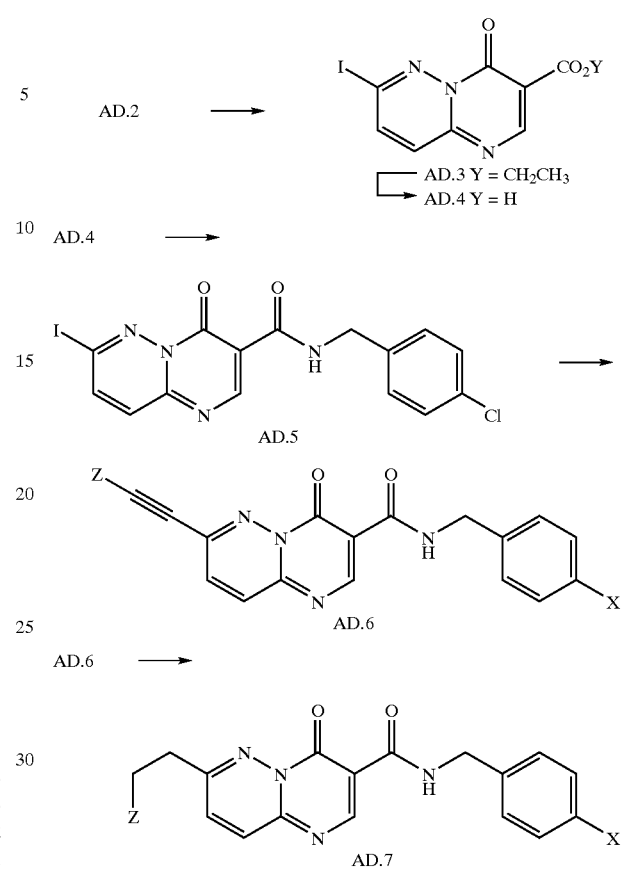

Specific examples of heterocycle W6.3 where G=4-morpholinomethyl or 4-tetrahydropyranylmethyl are prepared from intermediate AD.5 as described in Chart AE. Compounds of the formula AD.5 are transformed to the corresponding aldehyde AE.1 by reaction with carbon monoxide, tributyltin hydride and a palladium catalyst (e.g. palladium tetrakis-triphenylphosphine) (J. K. Stille *J. Am. Chem. Soc.* 1986, 108, 452–461.). Reductive amination of AE.1 with morpholine, acetic acid, and sodium triacetoxyborohydride provides the morpholinylmethyl derivatives of the formula AE.2 (Y=N). Alternatively, Wittig olefination between AE.1 and 4-tetrahydropyranylphosphonium bromide (Bestmann, H. J.; Stransky, W.; Vostrowsky, O. *Chem. Ber.* 1979, 109, 1694–1700.) employing sodium hexamethyldisilazide as base followed by hydrogenation catalyzed by palladium on carbon provides AE.2 (Y=CH).

CHART AD

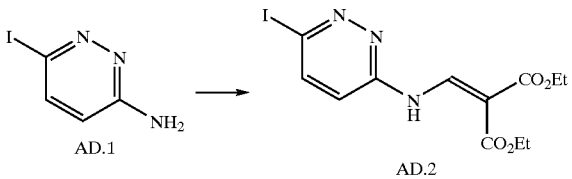

CHART AE

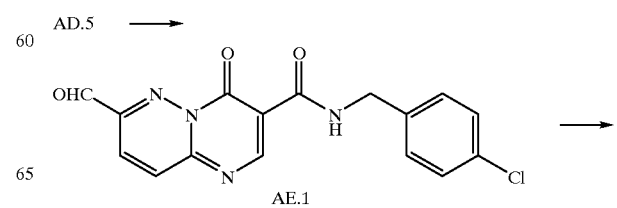

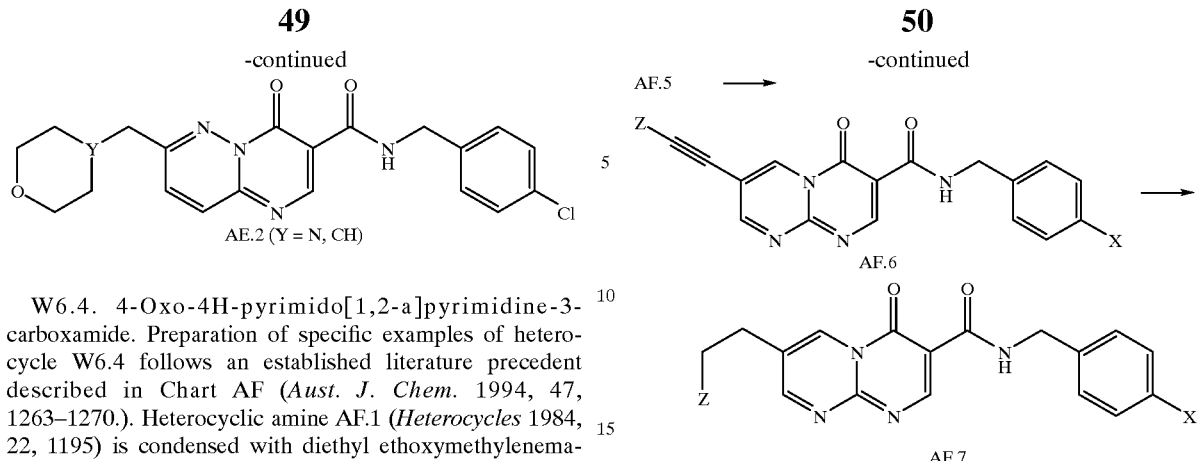

AE.2 (Y = N, CH)

W6.4. 4-Oxo-4H-pyrimido[1,2-a]pyrimidine-3-carboxamide. Preparation of specific examples of heterocycle W6.4 follows an established literature precedent described in Chart AF (*Aust. J. Chem.* 1994, 47, 1263–1270.). Heterocyclic amine AF.1 (*Heterocycles* 1984, 22, 1195) is condensed with diethyl ethoxymethylenemalonate to afford enamine AF.2. Cyclization of the resulting enamine by flash vacuum pyrolysis or by heating in a high boiling solvent provides pyrimidopyrimidine AF.3. The resulting ester AF.3 is then saponified to afford the corresponding carboxylic acid AF.4 which is then coupled with a benzylamnine (e.g. 4-chlorobenzylamine, 4-bromobenzylamine, or 4-fluorobenzylamine) mediated by 1,1'-carbonyldiimidazole (or other suitable carboxylic acid activating agent) to provide amides of the general formula AF.5. To prepare derivatives where G=3-hydroxypropyl or 3-hydroxy-1-propynyl, intermediate AF.5 may be further elaborated by Sonogashira coupling with an electron-rich acetylene (e.g. propargyl alcohol, Z=CH$_2$OH) catalyzed by PdCl$_2$(PPh$_3$)$_2$ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) provides the corresponding alkynyl derivatives of formula AF.6 (Z=CH$_2$OH). Saturation of the alkyne by hydrogenation catalyzed by palladium on carbon in alcoholic solvents affords alkyl derivatives of formula AF.7 (Z=CH$_2$OH).

CHART AF

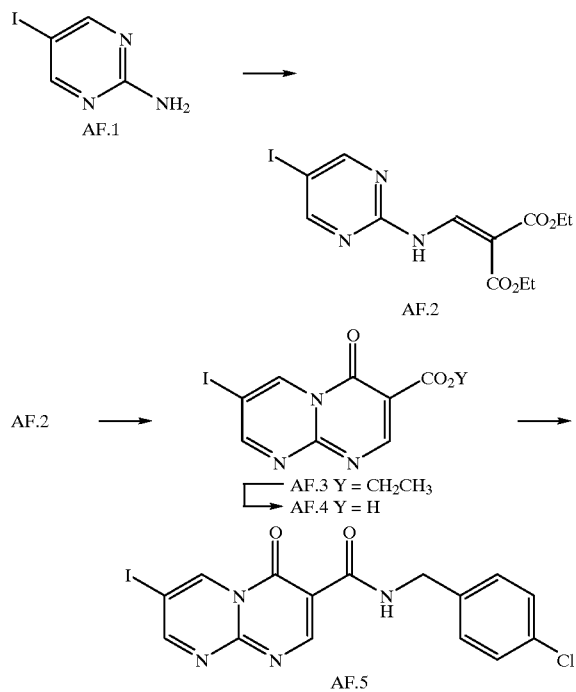

AF.5 →

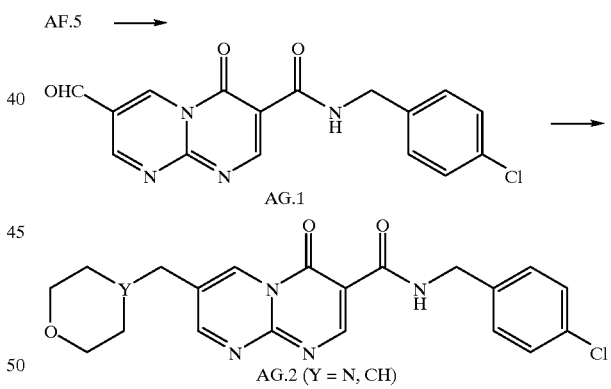

AF.6

AF.7

Specific examples of heterocycle W6.4 where G=4-morpholinomethyl or 4-tetreahydropyranylmethyl are prepared from intermediate AF.5 as described in Chart AG. Compounds of the formula AF.5 are transformed to the corresponding aldehyde AG.1 by reaction with carbon monoxide, tributyltin hydride and a palladium catalyst (e.g. palladium tetrakis-triphenylphosphine) (J. K. Stille *J. Am. Chem. Soc.* 1986, 108, 452–461.). Reductive amination of AG.1 with morpholine, acetic acid, and sodium triacetoxyborohydride provides the morpholinylmethyl derivatives of the formula AG.2 (Y=N). Alternatively, Wittig olefination between AG.1 and 4-tetrahydropyranylphosphonium bromide (Bestmann, H. J.; Stransky, W.; Vostrowsky, O. *Chem. Ber.* 1979, 109, 1694–1700.) employing sodium hexamethyldisilazide as base followed by hydrogenation catalyzed by palladium on carbon provides AG.2 (Y=CH).

CHART AG

W6.5. 8-Oxo-8H-pyrimido[1,2-b][1,2,4]triazine-7-carboxamides. The preparation of specific examples of heterocycle W6.5. follows established precedent as described in Chart AH. The 1-amino-4-iodo pyrazine AH.1 (Jovanovic, M. V. *Heterocycles*, 1984, 22, 1195) is condensed with methyl 2-(((4-chlorobenzyl)amino)carbonyl)-3-methoxy-2-propenoate to afford pyrimidotriazine AH.2. For specific examples where G=CH$_2$NR$^1$R$^2$, AH.2 is transmetallated with n-butyllithium and the resulting anion is reacted with dimethylformamide to afford the corresponding carboxaldehyde AH.3. The resulting aldehyde is then reacted under reductive amination conditions with a primary or secondary amine (e.g. morpholine) in the presence of acetic acid and sodium cyanoborohydride to afford examples such as AH.4. Alternatively for examples where G=3-hydroxypropyl or 3-hydroxy-1-propynyl, iodide AH.2 is coupled with an electron-rich acetylene (e.g. propargyl alcohol) through a modified Sonogashira coupling (Linstrumelle, G.; et. al, *Tetrahedron Lett.* 1993, 34, 6403) to afford compounds such as AH.5. Saturation of the alkyne by hydrogenation catalyzed by palladium on carbon in alcoholic solvents affords alkyl derivatives such as AH.6.

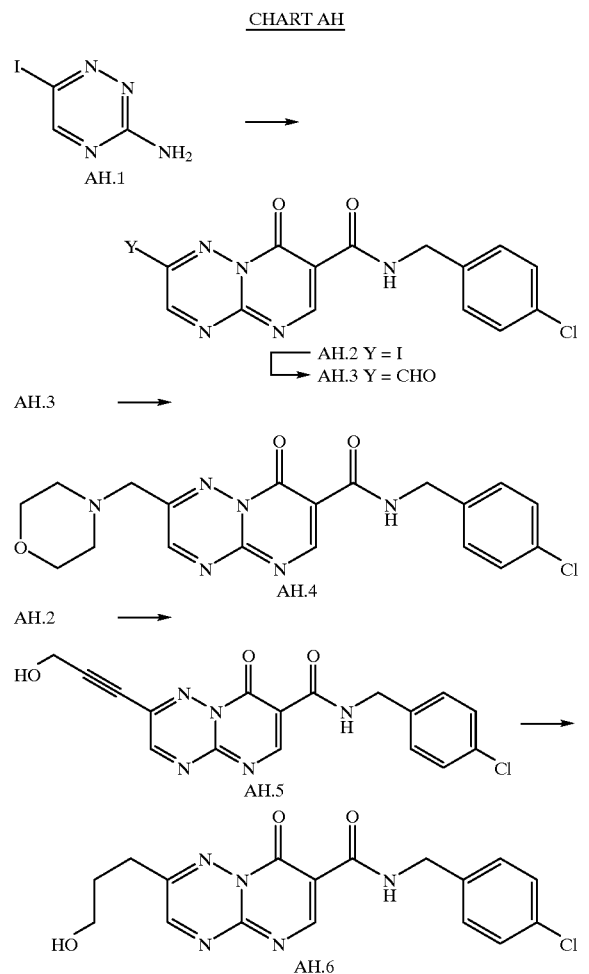

W7.1. 4-Oxo-4H-quinolizine-3-carboxamide. Specific examples of heterocycle W7.1 in which $G=CH_2NR^1R^2$ are prepared as described in Chart AI. 2-Methyl-3-pyridinecarboxylate AI.1 is reduced with lithium aluminum hydride, and the resulting alcohol AI.2 is protected as its methoxymethyl (MOM) ether by treatment with chloromethylmethyl ether in the presence of a suitable base to afford ether AI.3. Deprotonation with n-butyllithium and trapping of the resulting anion with diethyl ethoxymethylenemalonate provides the malonate diester AI.4 (U.S. Pat. No. 4,698,349). Thermal cyclization of AI.4 in refluxing diphenyl ether affords the quinolizine AI.5. The resulting ester AI.5 is then treated with a benzylamine (e.g. 4-chlorobenzylamine, 4-bromobenzylamine, or 4-fluorobenzylamine) at high temperature to afford the corresponding amides of the general formula AI.6, or alternatively, the ester may be saponified to afford the corresponding acid which is then coupled with a benzylamine mediated by 1,1'-carbonyldiimidazole (or other suitable carboxylic acid activating agent) to likewise provide AI.6. Deprotection of the methoxymethyl ether affords the benzyl alcohol AI.7 which is then activated as its mesylate ester by reaction with methanesulfonyl chloride and suitable base. Subsequent nucleophilic displacement by a primary or secondary amine (e.g. morpholine) provides derivatives of the formula AI.8.

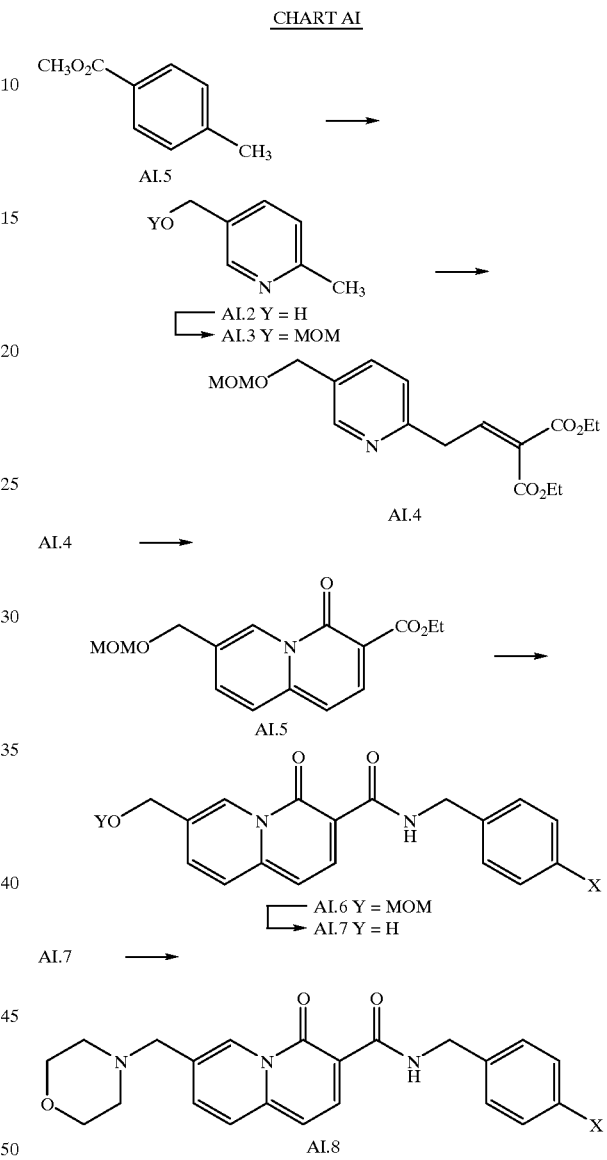

Specific examples of heterocycle W7.1 in which G=3-hydroxypropyl or 3-hydroxy-1-propynyl are prepared as described in Chart AJ. Oxidation of benzyl alcohol AI.7 to under Swern oxidation conditions or other suitable oxidizing conditions affords the corresponding aldehyde AJ.1. Treatment of AJ.1 with the corresponding Wittig reagent diethyl diazomethylphosphonate provides the terminal alkyne AJ.2. Deprotonation of the terminal alkyne with excess methylmagnesium bromide and trapping of the resulting anion with an aldehyde (e.g. formaldehyde) gives alkynyl derivatives of the formula AJ.3. Saturation of the alkyne by hydrogenation catalyzed by palladium on carbon in alcoholic solvents affords the corresponding alkyl derivatives of the formula AJ.4.

CHART AJ

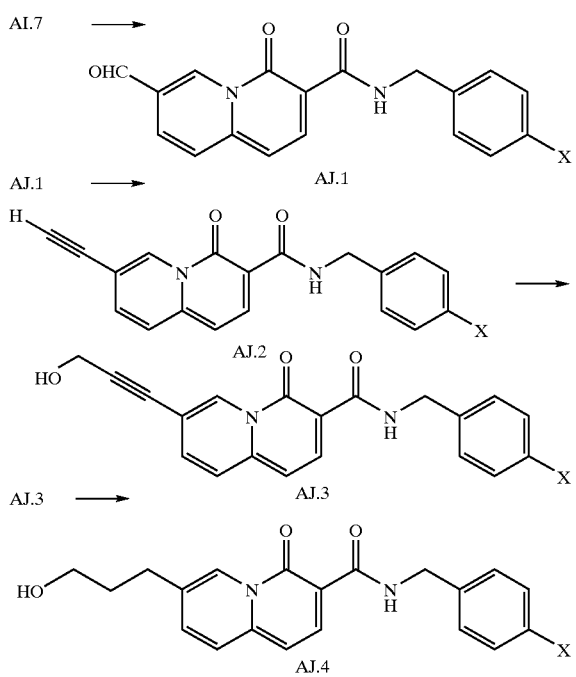

W7.2. 4-Oxo-4H-pyrido[1,2-a]pyrazine-3-carboxamide. Representative examples of heterocycle W7.2 in which G=3-hydroxypropyl or 3-hydroxy-1-propynyl are prepared as described in Chart AK. Saponification of ethyl 7-cyano4-oxo-4H-pyrido[1,2-a]pyrazine carboxylate (AK.1, *J. Chem. Soc. Perkin* 1 1977, 789) with lithium hydroxide in methanol provides the corresponding carboxylic acid AK.2. Carboxylic acid AK.2 is then coupled with a benzylamine (e.g. 4-chlorobenzylamine, 4-bromobenzylamine, or 4-fluorobenzylamine) mediated by 1,1'-carbonyldiimidazole (or other suitable carboxylic acid activating agent) to provide amides of the general formula AK.3. Reduction of the cyano functionality employing Raney nickel and sodium hypophosphite (*J. Chem. Soc.* 1962, 3961–3963.) in an acetic acid and water mixture provides the corresponding aldehyde AK.4. Treatment of the resulting aldehyde with the modified Wittig reagent diethyl diazomethylphosphonate affords the terminal alkyne AK.5. Deprotonation of the alkyne with excess methylmagnesium bromide and condensation with an aldehyde (e.g. formaldehyde) yields substituted alkynes of the general formula AK.6. Saturation of the alkyne by hydrogenation catalyzed by palladium on carbon in alcoholic solvents affords alkyl derivatives of the formula AK.6.

CHART AK

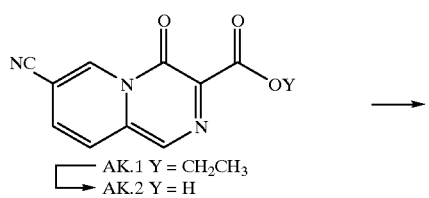

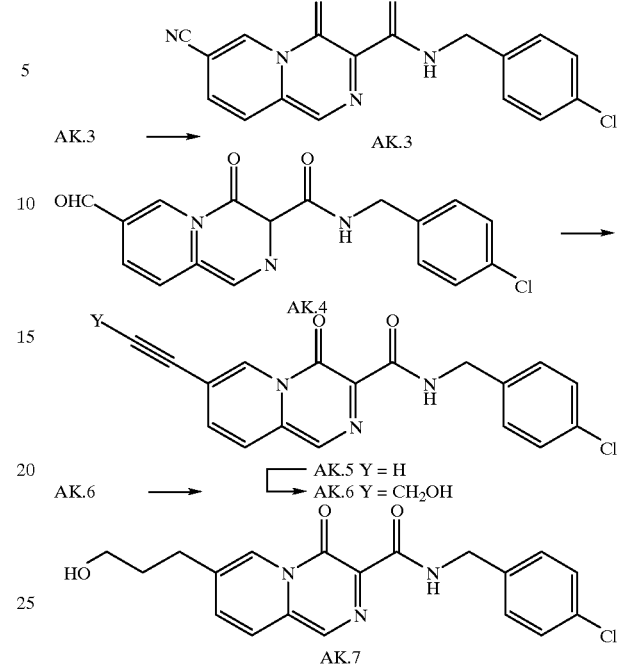

In another aspect, specific examples of heterocycle W7.2 in which G=morpholinyl-methyl are prepared as described in Chart AL. Reductive amination of AK.4 with a primary or secondary amine (e.g. morpholine) and sodium cyanoborohydride affords derivatives of the formula AL.1.

CHART AL

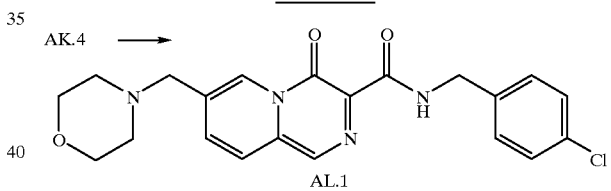

W7.3. 6-Oxo-6H-pyrido[1,2-a]pyrimidine-7-carboxamide. The preparation of specific examples of heterocycle W7.3 follows established literature precedent for 2-pyridones (Li, Q.; et. al. *J. Med. Chem.* 1996, 39, 3070) as described in Chart AM. Acetamidine is condensed with dimethyl methoxymethylenemalonate to afford pyrimidine AM.1. The ester AM.1 is hydrolyzed, heated with thionyl chloride, and the resulting acid chloride is reacted with morpholine to provide the amide AM.2. The chloroamide is then reduced with lithium aluminum hydride to afford pyrimidine AM.3. The pyrimidine is then deprotonated with n-butyllithium and the resulting anion is condensed with methyl 2-(((4-chlorobenzyl)amino)carbonyl)-3-methoxy-2-propenoate and subsequently cyclized to afford pyridopyrimidines of the general formula AM.4.

Chart AM

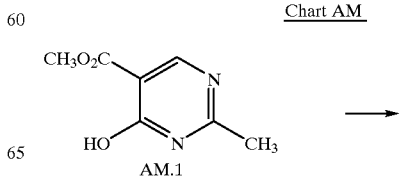

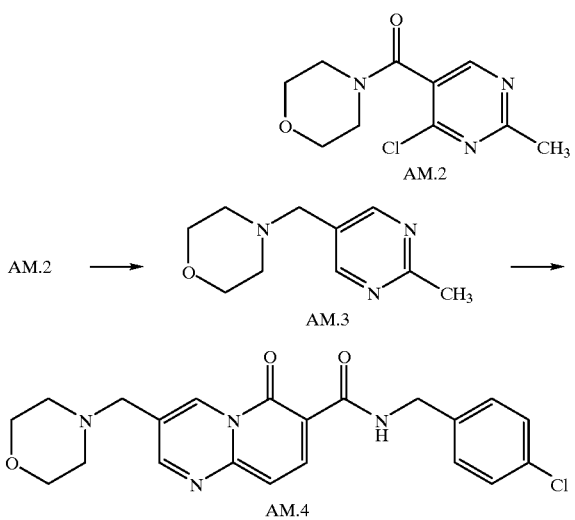

AM.2

AM.2 →

AM.3

AM.4

W8.1. 4-Oxo-4H-chromene-3-carboxamide. Specific examples of heterocycle W8.1 in which G=3-hydroxypropyl or 3-hydroxy-1-propynyl are prepared as described in Chart AN. 6-Bromochromone-3-carboxaldehyde AN.1 is oxidized to the carboxylic acid bromide AN.2 by a light-catalyzed oxidation with N-bromosuccinimide. The resulting acid bromide is then reacted with a benzylamine (e.g. 4-chlorobenzylamine, 4-bromobenzylamine, or 4-fluorobenzylamine) to provide amides of the general formula AN.3. Sonogashira coupling of the aryl bromide AN.3 with an electron-rich acetylene (e.g. propargyl alcohol, Z=CH$_2$OH) provides the alkyne derivatives of the formula AN.4. Saturation of the alkyne by hydrogenation catalyzed by palladium on carbon in alcoholic solvents affords the corresponding alkyl derivatives of the formula AN.5.

CHART AN

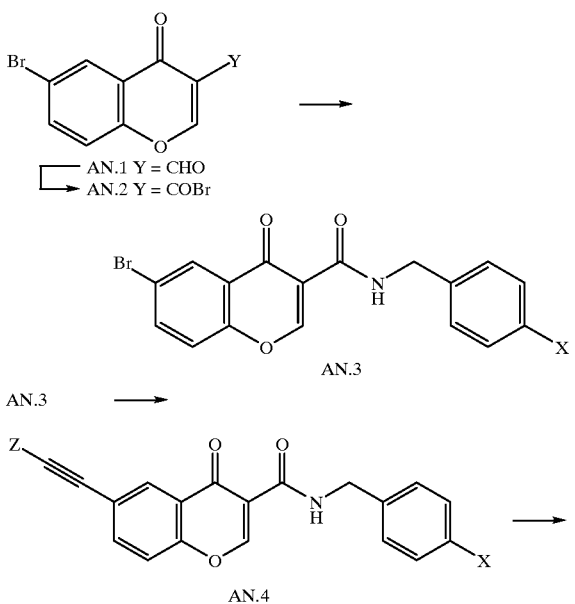

AN.1 Y = CHO
AN.2 Y = COBr

AN.3

AN.3 →

AN.4

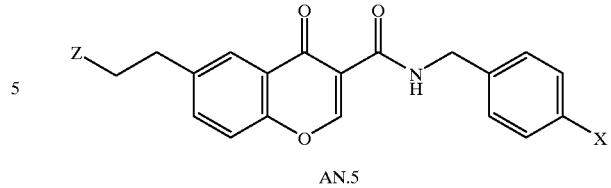

AN.5

In another example, derivatives of heterocycle W8.1 in which G=CH$_2$NR$^1$R$^2$ are prepared as described in Chart AO. 6-Methyl-3-formylchoromone (AO.1, Z=H) is irradiated in the presence of N-bromosuccinimide. The resulting acyl-bromide is then treated with an benzylamine (e.g. 4-chlorobenzylamine, 4-bromobenzylamine, or 4-fluorobenzylamine) to provide an intermediate carboxamide which is treated with a primary or secondary amine (e.g. morpholine) to provide compounds of the formula AO.2 (Z=H). In the case where 6,8-dimethyl-3-formylchoromone (AO.1, Z=CH$_3$) is employed the resulting product AO.2 (Z=morpholinylmethyl) is provided.

CHART AO

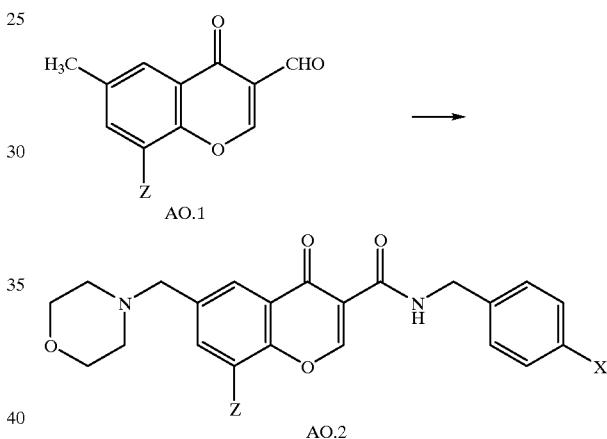

AO.1

AO.2

W8.2. 4-Oxo4H-pyrano[2,3-b]pyridine-3-carboxamide. Preparation of specific examples of heterocycle W8.2 follows an established literature precedent described in Chart AP (*Heterocycles* 1993, 35, 93–97). 3-Pyridylcarboxylic acid AP.1 (*J. Med. Chem.* 1997, 40, 2674–2687) is converted to its corresponding imidazolide with 1,1'-carbonyldiimidazole and coupled with the lithium anion of tert-butyl acetate to afford β-ketoester AP.2. Ring closure is effected by treating AP.2 with MeOCH=NMe$_2$$^+$ MeOSO$_3$$^-$ to afford ester AP.3. The resulting ester AP.3 is then hydrolyzed with trifluoroacetic acid to afford the corresponding carboxylic acid AP.4 which is then coupled with a benzylamine (e.g. 4-chlorobenzylamine, 4-bromobenzylamine, or 4-fluorobenzylamine) mediated by 1,1'-carbonyldiimidazole (or other suitable carboxylic acid activating agent) to provide amides of the general formula AP.5. To prepare derivatives where G=3-hydroxypropyl or 3-hydroxy-1-propynyl, intermediate AP.5 may be further elaborated by Sonogashira coupling with an electron-rich acetylene (e.g. propargyl alcohol, Z=CH$_2$OH) catalyzed by PdCl$_2$(PPh$_3$)$_2$ and copper (I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) provides the corresponding alkynyl derivatives of formula AP.6 (Z=CH$_2$OH). Saturation of the alkyne by hydrogenation catalyzed by palladium on carbon in alcoholic solvents affords alkyl derivatives of formula AP.7 (Z=CH$_2$OH).

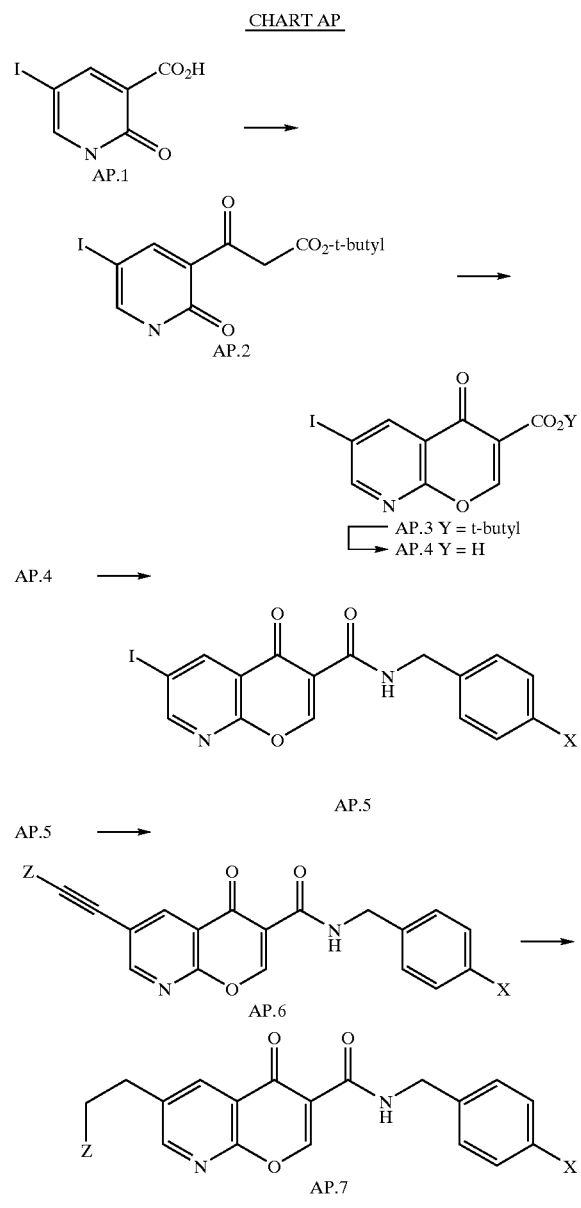

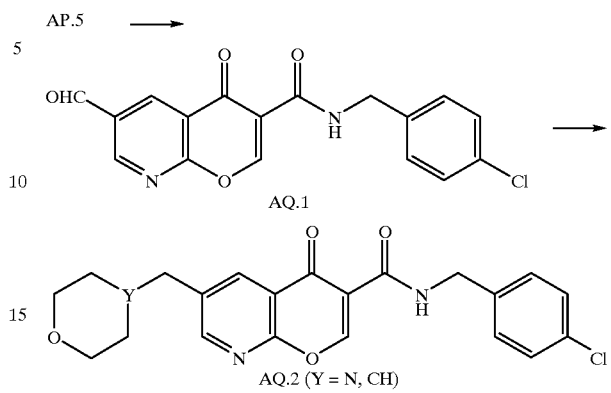

Specific examples of heterocycle W8.2 where G=4-morpholinomethyl or 4-tetreahydropyranylmethyl are prepared from intermediate AP.5 as described in Chart AQ. Compounds of the formula AP.5 are transformed to the corresponding aldehyde AQ.1 by reaction with carbon monoxide, tributyltin hydride and a palladium catalyst (e.g. palladium tetrakis-triphenylphosphine) (J. K. Stille *J. Am. Chem. Soc.* 1986, 108, 452–461.). Reductive amination of AQ.1 with morpholine, acetic acid, and sodium triacetoxyborohydride provides the morpholinylmethyl derivatives of the formula AQ.2 (Y=N). Alternatively, Wittig olefination between AQ.1 and 4-tetrahydropyranylphosphonium bromide (Bestmann, H. J.; Stransky, W.; Vostrowsky, O. *Chem. Ber.* 1979, 109, 1694–1700.) employing sodium hexamethyldisilazide as base followed by hydrogenation catalyzed by palladium on carbon provides AQ.2 Y=CH)

W8.8. 4-Oxo-4H-thiochromene-3-carboxamide. Specific examples of heterocycle W8.8 in which G=morpholinylmethyl are prepared as described in Chart AR. Deprotonation of the 6-methyl-thiochroman-4-one AR.1 with LDA at low temperatures and subsequent treatment of the enolate with HMPA and methylcyanoformate (Mander, L. N.; Sethi, S. P. *Tetrahedron. Lett.* 1983, 24, 5425–5428) provides the β-ketoester AR.2. Bromination alpha to the carbonyl using bromine in a mixture of diethyl ester and carbon tetrachloride affords bromide AR.3. Subsequent elimination is affected using lithium carbonate in DMF at 100° C. to give the thiochromenone AR.4. Benzylic bromination (NBS, benzoyl peroxide, carbon tetrachloride) provides bromide AR.5, which is subsequently displaced with a primary or secondary amine (e.g. morpholine) to give AR.6. The resulting ester is then treated with a dimethylaluminumamide derived from trimethylaluminum and a benzylamine (e.g. 4-chloro-benzylamine, 4-bromobenzylamine, or 4-fluorobenzylamine) to afford amides of the formula AR.7.

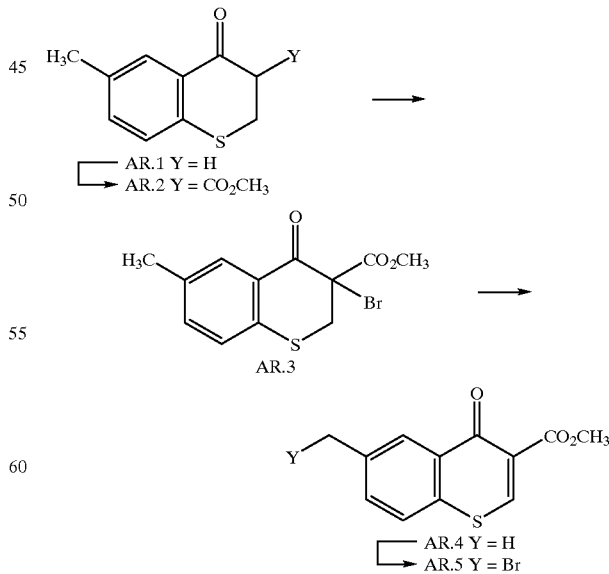

AR.5 ⟶

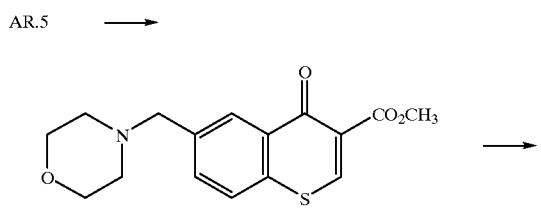

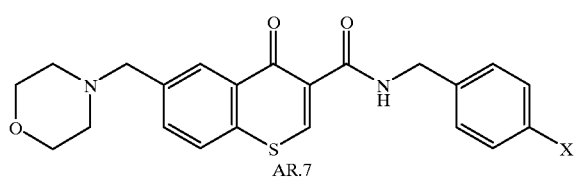

W8.9. 4-Oxo-4H-thiopyrano[2,3-b]pyridine-3-carboxamides. Preparation of specific examples of heterocycle W8.9 follows an established literature precedent described in *Heterocycles* 1993, 35, 93–97. and is analogous to that described above for heterocycle W8.2. employing 2-thiol-5-iodo-3-pyridylcarboxylic acid in the place of AO.1 prepared by N-iodosuccinimide iodination (*J. Med. Chem.* 1997, 40, 2674–2687) of 2-thiol-3-pyridylcarboxylic acid (*J. Heterocyclic Chem.* 1985, 22, 1353.).

Alternatively, derivatives of heterocycle W8.9 where $G=CH_2NR^1R^2$ are prepared as described in Chart AS. Activation of carboxylic acid AS.1 (*Heterocycles*, 1994, 38, 333) with 1,1'-carbonyldiimidazole or another suitable acid-activating agent followed by the addition of the lithium salt of tert-butyl acetate results in compound AS.2. Reaction of AS.2 under McCombie cyclization conditions using $MeOCH=NMe_2^+MeOSO_3^-$ (*Heterocycles*, 1993, 35, 93) affords thiopyranopyridin-4-one AS.3. Bromination at the benzylic position using N-bromosuccinimide and benzoylperoxide provides bromide AS.4, which undergoes nucleophilic displaced by a primary or secondary amine (e.g. morpholine) to afford AS.5. Deprotection of the tert-butylester provides acid AS.6, which is then coupled with 4-chlorobenzylamine via well known methods to afford carboxamide derivatives of the formula AS.7.

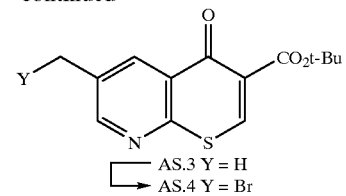

AS.4 ⟶

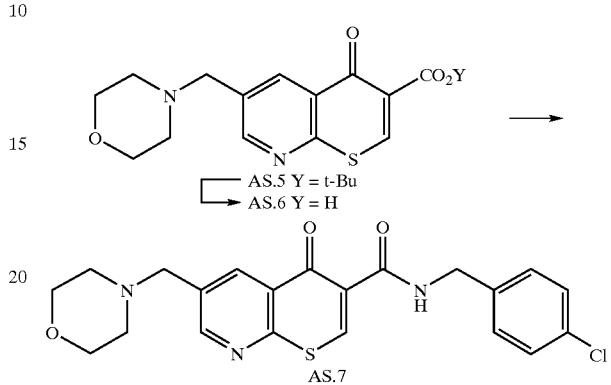

W10.1. 4-Hydroxy-2H-1,2-benzoxazine-3-carboxamides. Preparation of specific examples of heterocycle W10.1 follows an established literature precedent described in Chart AT (G. S. Shchegoleva *Khim. Geterotsikl. Soedin.*, Sb. 1970, 2, 278–281; *Chem. Abst.* 1972, 76, 140675.). Treatment of β-ketoesters of the formula AT.1 (prepared as described in Chart AV, Y=4-morpholinylmethyl; Chart AW, Y=iodo and 3-hydroxypropyl; Chart AX, Y=4-tetrahydropyranylmethyl) with sodium nitrite in acetic acid (*J. Chem. Soc.* 1925, 579) affords oximes of the formula AT.2. Upon heating, oximes AT.2 cyclize to afford compounds of the formula AT.3. The resulting ester AT.3 is then reacted with a benzylamine (e.g. 4-chlorobenzylamine, 4-bromobenzylamine, or 4-fluorobenzylamine) at high temperature or alternatively the ester is saponified to afford the corresponding carboxylic acid which is then coupled with a benzylamine mediated by 1,1'-carbonyldiimidazole (or other suitable carboxylic acid activating agent) to provide amides of the general formula AT.4. In the case where Y=iodo, the resulting amide may be further elaborated as described in Chart AU by Sonogashira coupling with an electron-rich acetylene (e.g. propargyl alcohol, $Z=CH_2OH$) catalyzed by $PdCl_2(PPh_3)_2$ and copper (I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) to provide the corresponding alkynyl derivatives of formula AU.1 ($Z=CH_2OH$).

CHART AS

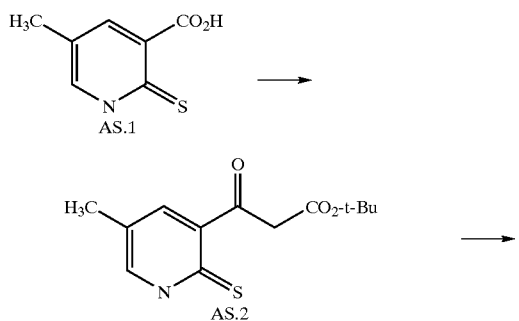

CHART AT

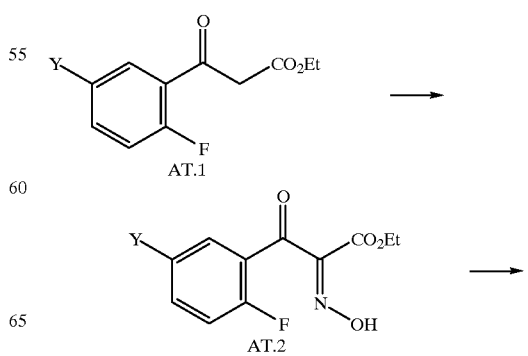

-continued

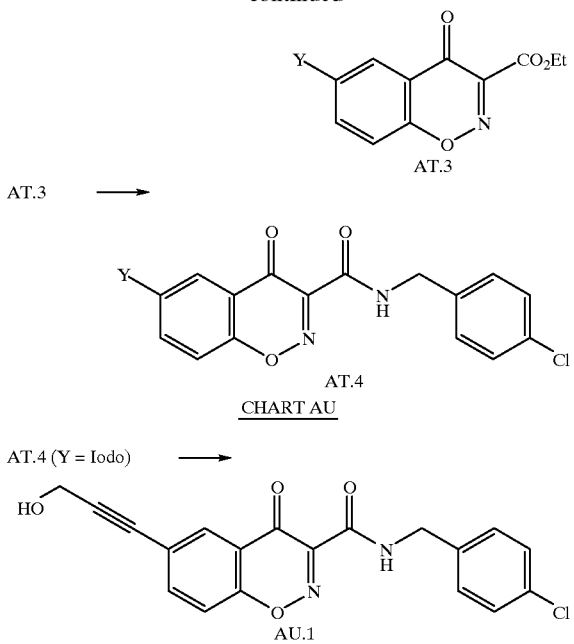

AT.1 (W=morpholinylmethyl) is prepared according to Chart AV. Reductive amination of 3-bromo4-fluorobenzaldehyde (AV.1) with morpholine, acetic acid, and sodium triacetoxyborohydride provides the benzylmorpholine AV.2. Metal-halogen exchange between n-butyllithium and AV.2 at −70° C. in tetrahydrofuran followed by addition of the resulting aryl lithium to N-methoxy-N-methylacetamide yields the methylketone AV.3. Treatment of AV.3 with a base such as sodium hydride in the presence diethylcarbonate affords the β-ketoester AT.1 (W=morpholinylmethyl) which may then be employed as in Chart AT.

CHART AV

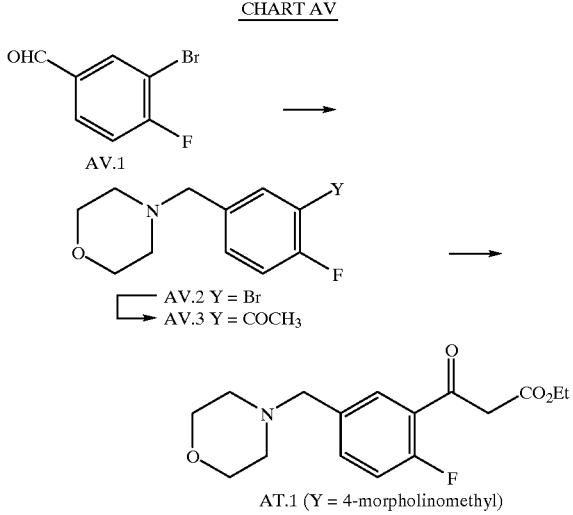

AT.1 (W=iodo) is prepared according to Chart AW. Conversion of 2-fluoro-5-iodobenzoic acid AW.1 (Blackburn, B. K. et. al. J. Med. Chem. 1997, 40, 717–729) to its corresponding imidazolide with 1,1'-carbonyldiimidazole followed by treatment with the trimethylsilyl ester of ethyl hydrogen malonate in the presence of DBU (Wang, X.; Monte, W. T.; Napier J. J.; Ghannam, A. Tetrahedron Lett. 1994, 35, 9323–9326) provides β-ketoester AT.1 (W=iodo) which may be employed as in Chart AT.

AT.1 (W=3-hydroxypropyl) is prepared according to Chart AW. Sonogashira coupling of AT.1 (W=iodo) with propargyl alcohol as described above provides the corresponding alkynyl derivatives AW.2. Saturation of the alkyne by hydrogenation catalyzed by palladium on carbon in alcoholic solvents affords AT.1 (W=3-hydroxypropyl) which may be employed as in Chart AT.

CHART AW

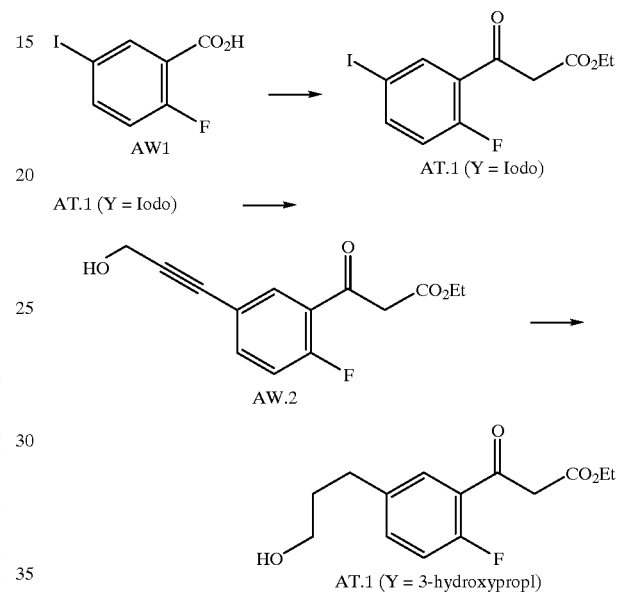

AT.1 (W=4-tetrahydropyranylmethyl) is prepared according to Chart AX. Wittig olefination between 3-bromo-4-fluorobenzaldehyde (AV.1) and 4-tetrahydropyranylphosphonium bromide (Bestmann, H. J.; Stransky, W.; Vostrowsky, O. Chem. Ber. 1979, 109, 1694–1700.) employing sodium hexamethyldisilazide as base provides the olefin AX.1. Metal-halogen exchange between n-butyllithium and AX.1 at −70° C. in tetrahydrofuran followed by addition of the resulting aryl lithium to carbon dioxide yields the carboxylic acid AX.2. Saturation of the olefin by hydrogenation of AX.2 employing palladium on carbon as catalyst affords AX.3. Conversion of AX.3 to its corresponding imidazolide with 1,1'-carbonyldiimidazole followed by treatment with the trimethylsilyl ester of ethyl hydrogen malonate in the presence of DBU (Wang, X.; Monte, W. T.; Napier J. J.; Ghannam, A. Tetrahedron Lett. 1994, 35, 9323–9326) provides 3-ketoester AT.1 (Y=4-tetrahydropyranymethyl) which may be employed as in Chart AT.

CHART AX

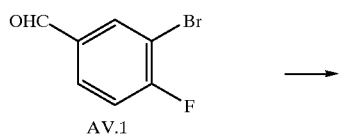

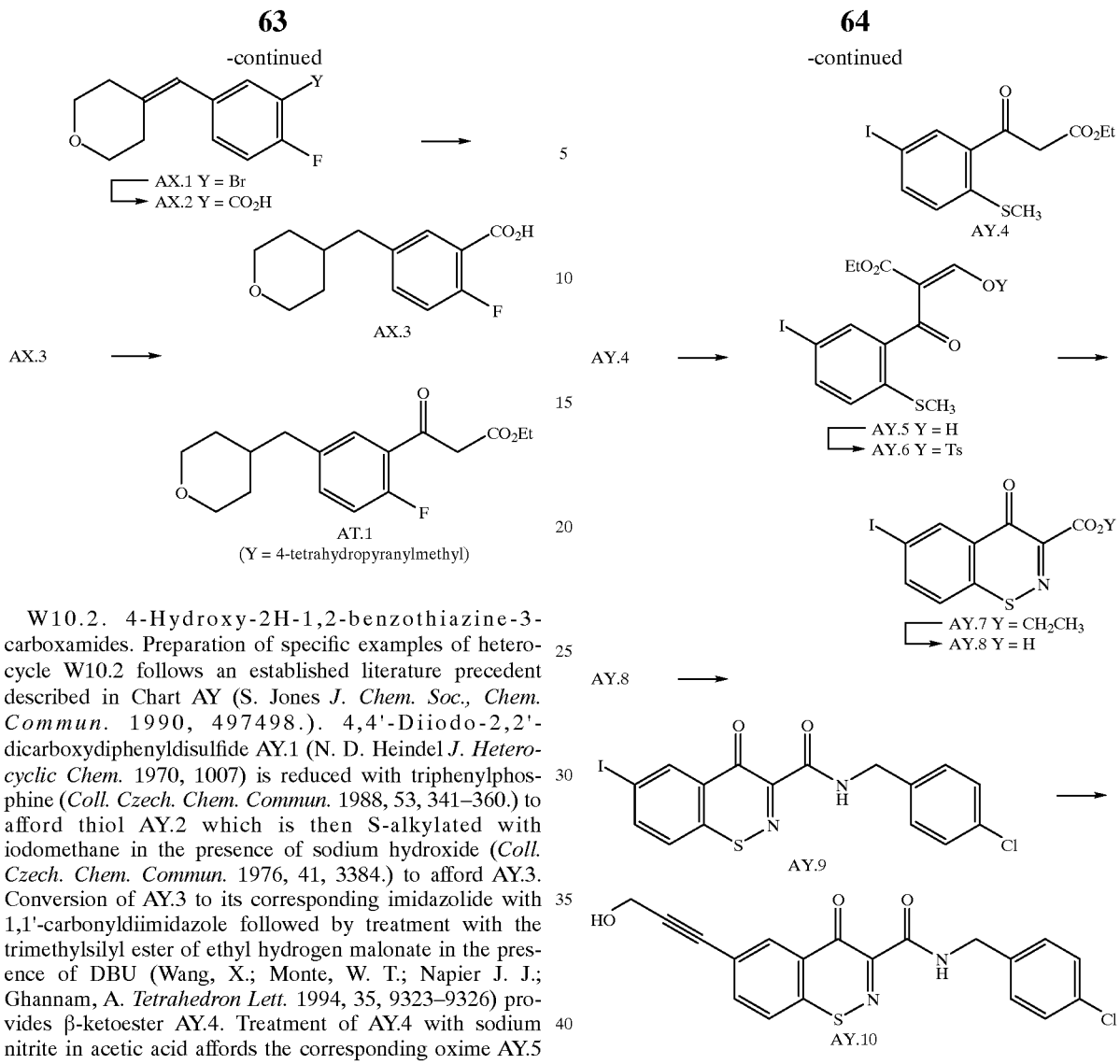

W10.2. 4-Hydroxy-2H-1,2-benzothiazine-3-carboxamides. Preparation of specific examples of heterocycle W10.2 follows an established literature precedent described in Chart AY (S. Jones *J. Chem. Soc., Chem. Commun.* 1990, 497498.). 4,4'-Diiodo-2,2'-dicarboxydiphenyldisulfide AY.1 (N. D. Heindel *J. Heterocyclic Chem.* 1970, 1007) is reduced with triphenylphosphine (*Coll. Czech. Chem. Commun.* 1988, 53, 341–360.) to afford thiol AY.2 which is then S-alkylated with iodomethane in the presence of sodium hydroxide (*Coll. Czech. Chem. Commun.* 1976, 41, 3384.) to afford AY.3. Conversion of AY.3 to its corresponding imidazolide with 1,1'-carbonyldiimidazole followed by treatment with the trimethylsilyl ester of ethyl hydrogen malonate in the presence of DBU (Wang, X.; Monte, W. T.; Napier J. J.; Ghannam, A. *Tetrahedron Lett.* 1994, 35, 9323–9326) provides β-ketoester AY.4. Treatment of AY.4 with sodium nitrite in acetic acid affords the corresponding oxime AY.5 which is then O-tosylated with 4toluenesulfonylchloride and an amine base to provide AY.6. Upon heating AY.6 in toluene with p-toluenesulfonic acid, ring cyclization occurs to afford ester AY.7. The resulting ester AY.7 is then saponified to afford the corresponding carboxylic acid AY.8 which is then coupled with a benzylamine (e.g. 4-chlorobenzylamine, 4-bromobenzylamine, or 4-fluorobenzylamine) mediated by 1,1'-carbonyldiimidazole (or other suitable carboxylic acid activating agent) to provide amides of the general formula AY.9. Sonogashira coupling of AY.9 with propargyl alcohol catalyzed by PdCl$_2$(PPh$_3$)$_2$ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) provides the corresponding alkynyl derivatives of formula AY.10.

Examples of heterocycle W10.2 where G=4-morpholinylmethyl are prepared as described in Chart AZ. Carboxamide AY.9 is treated with carbon monoxide, tributyltin hydride, and a palladium catalyst (e.g. palladium tetrakis-triphenyl-phosphine) (J. K. Stille *J. Am. Chem. Soc.* 1986, 108, 452–461.) to afford the corresponding aldehyde AZ.1. Reductive amination of AZ.1 with morpholine, acetic acid, and sodium triacetoxyborohydride provides the morpholinylmethyl derivatives of the formula AZ.2.

CHART AZ

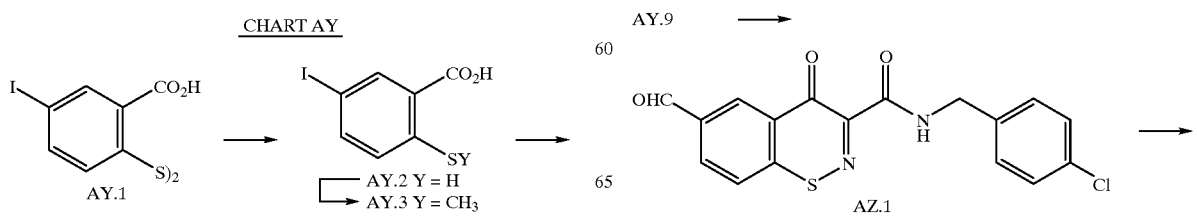

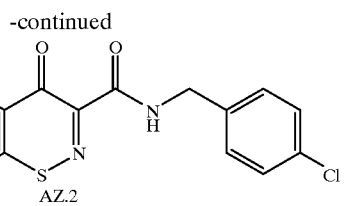

AZ.2

W13.4. 4-Hydroxy-1H-2,1-benzothiazine-3-carboxamide 2,2-dioxides. The preparation of specific examples of heterocycle W13.4 is described in Chart BA. For compounds in which G=CH$_2$NR$^1$R$^2$, 6-bromo-3,4-dihydro-1H-2,1-benzothiazin-4-one 2,2-dioxide BA.1 (B. Loev, K. M. Snader *J. Heterocyclic Chem.*, 1967, 4, 403) is treated with palladium tetrakistriphenylphosphine and tributyltin hydride under an atmosphere of carbon monoxide (Baillageon, V. P., Stille J. K., *J. Am. Chem. Soc.* 1983, 105, 7175) to afford aldehyde BA.2. Reductive amination of BA.2 with a primary or secondary amine (e.g. morpholine) and sodium triacetoxyborohydride affords compounds such as BA.3. Treatment of BA.3 with a benzylisocyanate (e.g. 4-chlorobenzyl isocyanate prepared as described by H. Stark, et. al. *J. Med. Chem.* 1996, 39, 1157–1163.) affords the corresponding carboxamide BA.4.

CHART BA

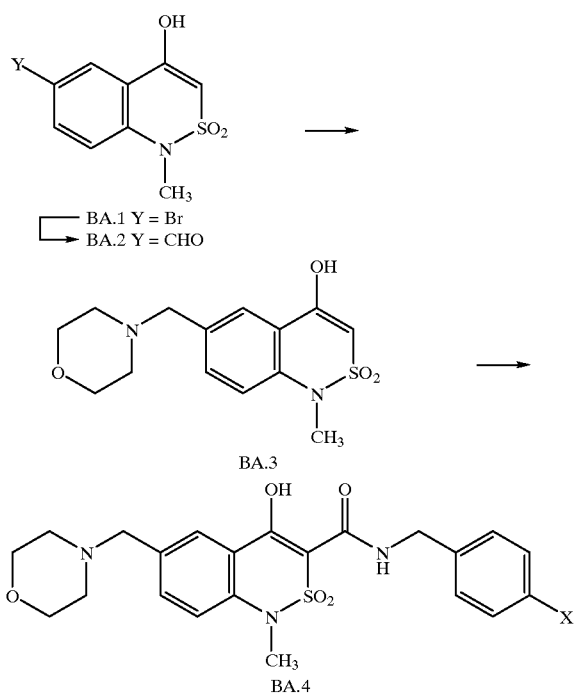

Additional examples of heterocycle W13.4 in which G 3-hydroxypropyl or 3-hydroxy-1-propynyl are prepared as described in Chart BW. 5-Iodoanthranilic acid methyl ester (BW.1) is converted to the corresponding sulfonamide with methane-sulfonyl chloride to afford BW.2. The sulfonamide nitrogen is then alkylated with an optionally substituted alkylhalide (e.g. iodomethane) or other appropriate electrophile in the presence of an inorganic base (e.g. potassium carbonate) to afford BW.3. Sonogashira coupling of BW.3 with an electron-rich acetylene (e.g. tetrahydro-2-(2-propynyloxy)-2H-pyran) provides the corresponding alkynyl derivative of the formula BW.4. Cyclization of BW.4 in the presence of a base (e.g. sodium hydride) affords the benzothiazin-4-one dioxide BW.5. Treatment of BW.5 with a benzylisocyanate (e.g. 4-chlorobenzylisocyanate) as above affords compounds of the formula BW.6. Deprotection of the tetrahydropyran protecting group employing standard conditions (Green, T. W.; Wuts, P. G. M. *Protective Groups in Organic Synthesis,* 1999) affords derivatives of the formula BW.7. Saturation of the alkyne by hydrogenation catalyzed by palladium on carbon in alcoholic solvents affords BW.8.

CHART BW

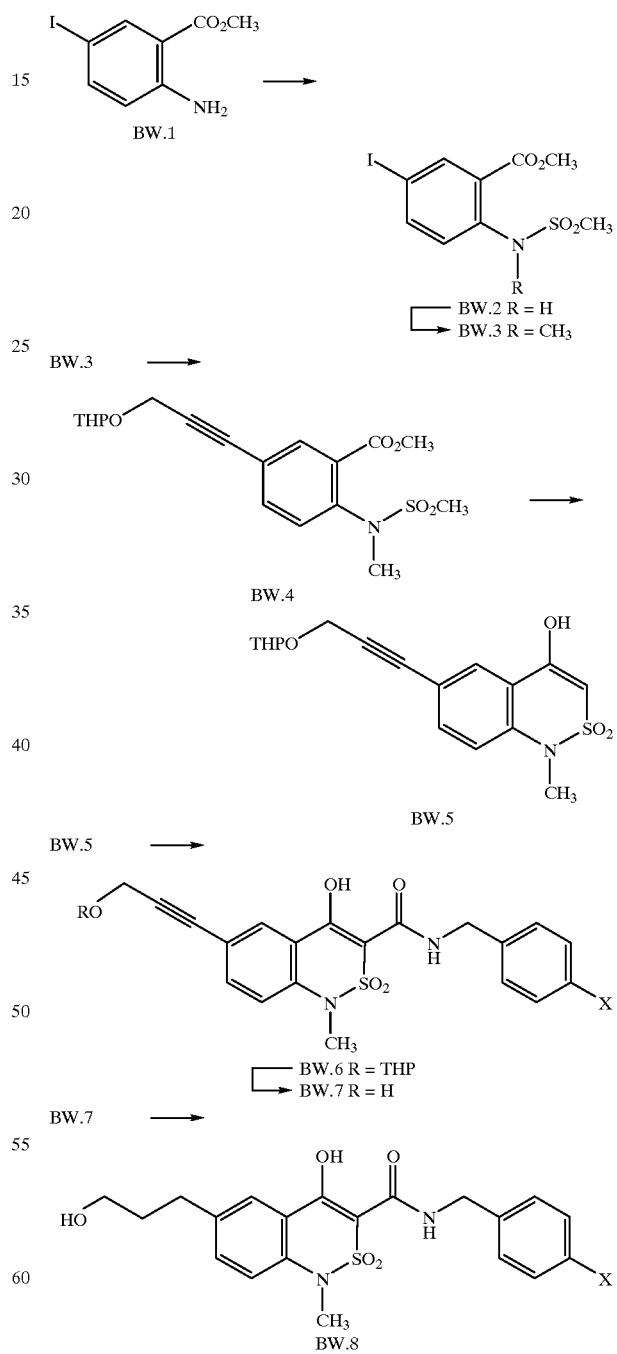

W14.1. 4H-1,4-Benzothiazine-2-carboxamide 1-oxides. Specific examples of heterocycle W14.1 in which G=morpholinylmethyl are prepared as described in Chart BB. 6-Bromo-2-benzothiazolinone BB.1 is transmetallated utilizing n-butyllithium and following the addition of methyl cyanoformate affords ester BB.2. The resulting ester BB.2 is then converted under standard conditions to the amide BB.3 by hydrolysis and amide coupling. Amide BB.3 is then reduced with lithium aluminum hydride to afford the thiol BB.4. The thiol is then cyclized with methyl 2-bromo-3-methoxyacrylate (WO 94/24085) to afford the ester BB.5. The ester is then converted to the benzyl amide followed by m-CPBA oxidation to the sulfoxide BB.6.

CHART BB

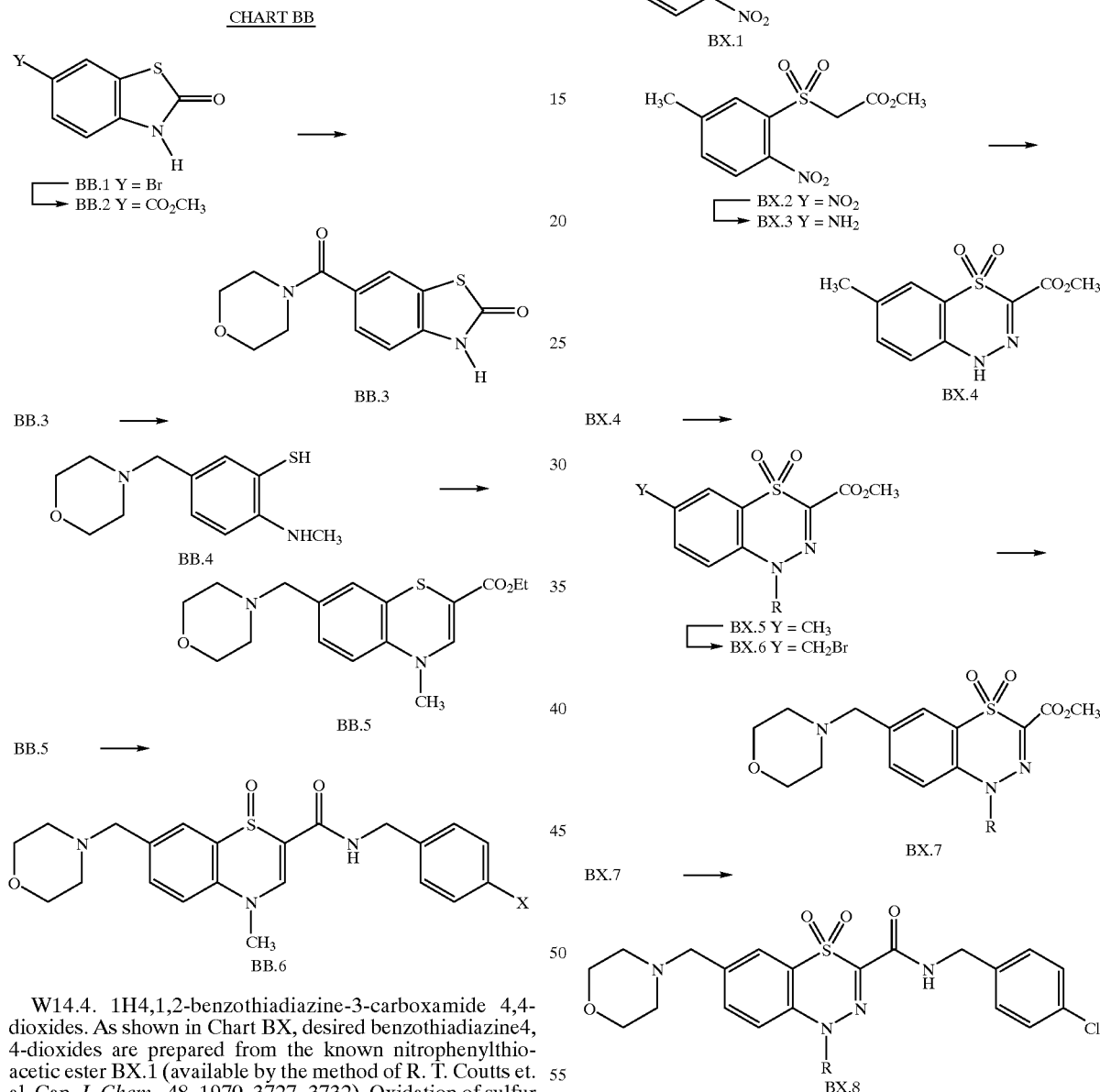

W14.4. 1H4,1,2-benzothiadiazine-3-carboxamide 4,4-dioxides. As shown in Chart BX, desired benzothiadiazine4,4-dioxides are prepared from the known nitrophenylthioacetic ester BX.1 (available by the method of R. T. Coutts et. al. Can. *J. Chem.*, 48, 1970, 3727–3732). Oxidation of sulfur using m-chloroperoxybenzoic acid or another suitable oxidant gives sulfone BX.2 which is reduced to amine BX.3 by catalytic hydrogenation using palladium on carbon and hydrogen gas or by another suitable reducing methodology. Treatment of BX.3 with sodium nitrite in acetic acid results in formation of cyclic product BX.4 which is alkylated at N-1 with iodomethane (R=CH$_3$) in DMF and K$_2$CO$_3$ at 25° C. or with some other suitable alkylating agent to give BX.5 (R=alkyl, substituted alkyl). Compound BX.5 is brominated for example with N-bromosuccinimide initiated by light in a suitable solvent such as dichloroethane to obtain the benzyl bromide BX.6 which can be reacted with morpholine to obtain compound BX.7. Finally, ester BX.7 can be reacted with 4-chlorobenzylamine, for example at elevated temperature in methanol with a trace of sodium methoxide or via another suitable amide formation route, to give desired products of the formula BX.8.

Chart BX

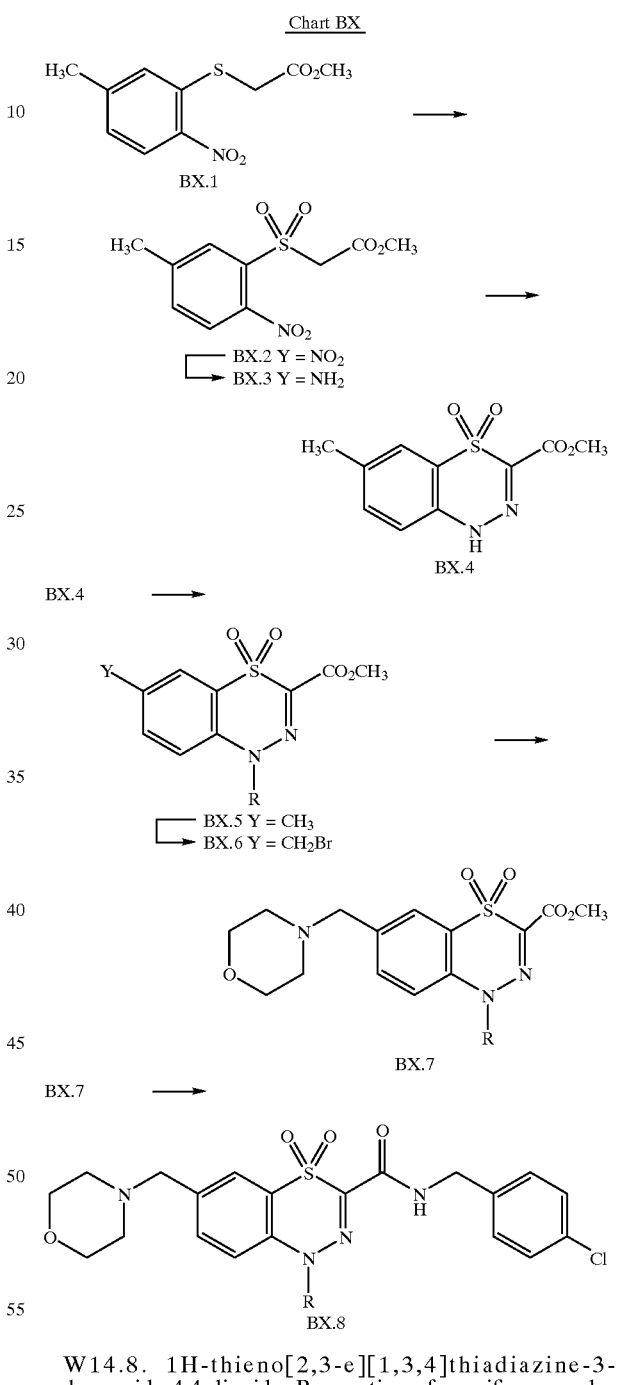

W14.8. 1H-thieno[2,3-e][1,3,4]thiadiazine-3-carboxamide 4,4-dioxide. Preparation of specific examples of heterocycle W14.8 follows an established precedent for the corresponding ring synthesis (*J. Heterocycl. Chem.* 1998, 35, 933–938), Chart BC. Aminothiophene BC.1 is prepared as described in the literature (Stephens, C. E.; Sowell, J. W. *J. Heterocyclic Chem.* 1998, 35, 933.). Condensation of this ester with a benzylamine (e.g. 4-chlorobenzylamine, 4-bromobenzylamine, or 4-fluorobenzylamine) at high temperatures affords amides of the formula BC.2. Treatment of this amine with sodium nitrite in acetic acid provides thienothiadiazine BC.3. Bromination of BC.3 with N-bromosuccinimide affords BC.4. Examples where G=CH$_2$NR$^1$R$^2$ are then prepared from BC.4 by formylation with PdCl$_2$(PPh$_3$)$_2$, carbon monoxide, and sodium formate in DMF to give BC.5 according to the procedure of Okano (*Bull Chem Soc Jpn* 1994, 67, 2329. This material is subjected to reductive amination conditions with a primary or secondary amine (e.g. morpholine) to afford BC.6 which is then subjected to alkylation at nitrogen to provide BC.7 by well know methods to those skilled in the art.

CHART BC

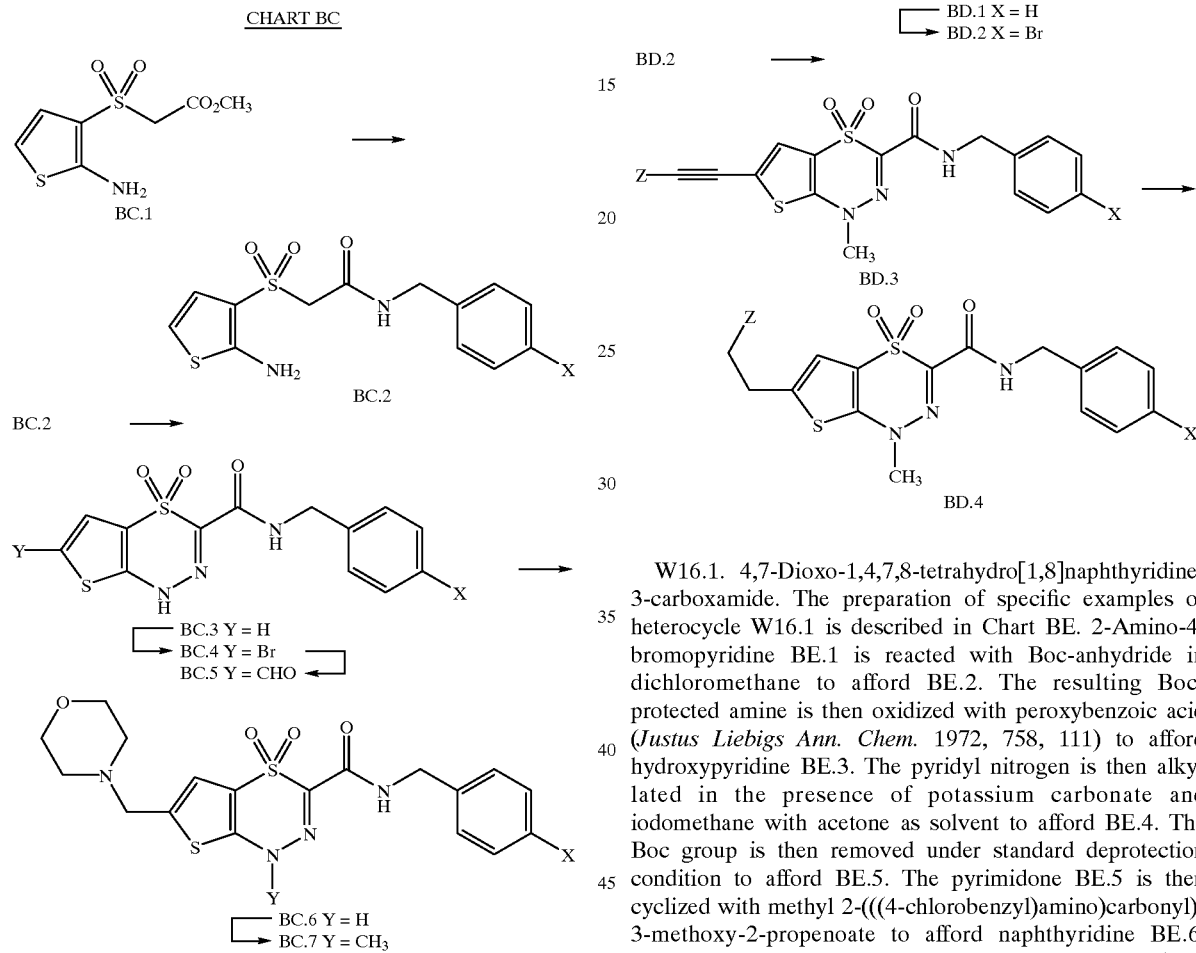

Specific examples of heterocycle W14.8 where G=3-hydroxypropyl or 3-hydroxy-1-propynyl are prepared as described in Chart BD. From intermediate BC.3, alkylation of the nitrogen is achieved using iodomethane and a carbonate base (e.g. potassium carbonate) in DMF giving compound BD.1. Bromination on the thiophene ring using NBS in DMF at room temperature provides compound BD.2. This material is then coupled with an electron-rich acetylene (e.g. propargyl alcohol, Z=CH$_2$OH) catalyzed by PdCl$_2$(PPh$_3$)$_2$ and copper(I)iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) to provide the corresponding alkynyl derivative BD.3. Saturation of the alkyne by hydrogenation catalyzed by palladium on carbon in alcoholic solvents affords derivatives of the formula BD.4.

W16.1. 4,7-Dioxo-1,4,7,8-tetrahydro[1,8]naphthyridine-3-carboxamide. The preparation of specific examples of heterocycle W16.1 is described in Chart BE. 2-Amino-4-bromopyridine BE.1 is reacted with Boc-anhydride in dichloromethane to afford BE.2. The resulting Boc-protected amine is then oxidized with peroxybenzoic acid (*Justus Liebigs Ann. Chem.* 1972, 758, 111) to afford hydroxypyridine BE.3. The pyridyl nitrogen is then alkylated in the presence of potassium carbonate and iodomethane with acetone as solvent to afford BE.4. The Boc group is then removed under standard deprotection condition to afford BE.5. The pyrimidone BE.5 is then cyclized with methyl 2-(((4-chlorobenzyl)amino)carbonyl)-3-methoxy-2-propenoate to afford naphthyridine BE.6. Reaction of BE.6 with an alkylating agent (e.g. iodomethane) in the presence of potassium carbonate with acetone as solvent affords compounds such as BE.7. Compound BE.7 is then coupled through a modified Sonogashira coupling (Linstrumelle, G.; et. al, *Tetrahedron Lett,* 1993, 34 6403) with an electron-rich acetylene (e.g. propargyl alcohol, Z=CH$_2$OH) to afford the alkyne derivative BE.8. Saturation of the alkyne by hydrogenation catalyzed by palladium on carbon in alcoholic solvents affords alkyl derivatives of formula BE.9 (Z=CH$_2$OH).

Chart BE

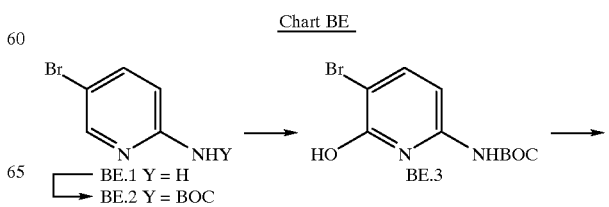

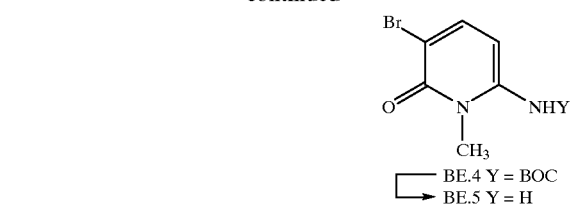

BE.4 Y = BOC
BE.5 Y = H

BE.5 →

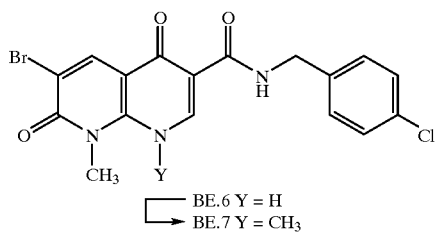

BE.6 Y = H
BE.7 Y = CH₃

BE.7 →

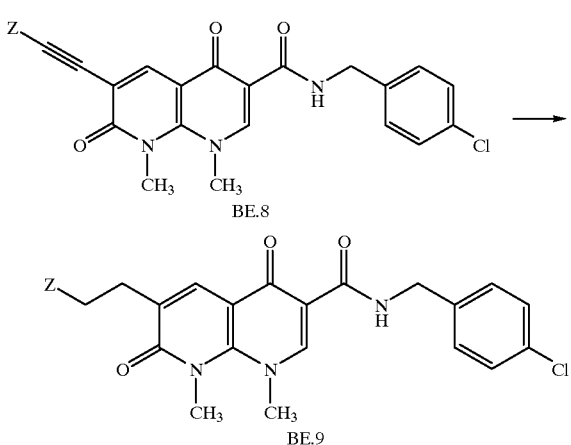

BE.8

BE.9

Specific examples of heterocycle W16.1 in which G=CH₂NR¹R² are prepared as described in Chart BF. Naphthyridine BE.7 is coupled under modified Negishi coupling conditions with vinylzinc in the presence of Pd(PPh₃)₄ (Palmgren, A.; et. al. *J. Org. Chem.* 1998, 63, 3764) to afford the vinyl derivative BF.1. Oxidative cleavage of the olefin with osmium tetroxide and sodium periodiate provides the aldehyde BF.2. The resulting aldehyde is then reacted under reductive amination conditions with a primary or secondary amine (e.g. morpholine) in the presence of acetic acid and sodium cyanoborohydride to afford compounds such as BF.3.

Chart BF

BE.7 →

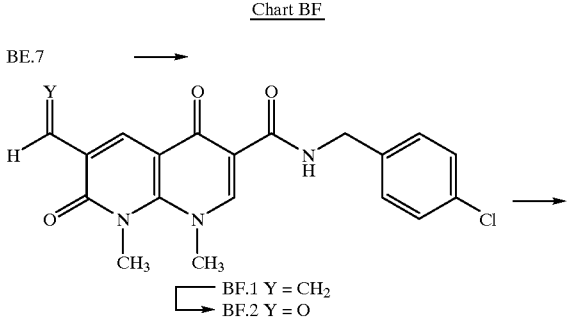

BF.1 Y = CH₂
BF.2 Y = O

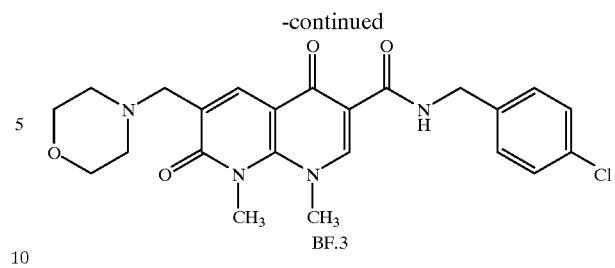

BF.3

W17. 4-Oxo-4H-pyrido[2,1-c][1,2,4]triazine-3-carboxamide. Preparation of specific examples of heterocycle W17 follows an established literature precedent described in Chart BG (U.S. Pat. No, 4,081,545). 2-Hydrazino-5-iodopyridine BG.1 is condensed with diethyl ketomalonate and subjected to thermal cyclization in 1,2,4-trichloroethane to provide pyridotriazine ester BG.2. The resulting ester BG.2 is then treated with a benzylamine (e.g. 4-chlorobenzylamine, 4-bromobenzylamine, or 4-fluorobenzylamine) at high temperature to afford the corresponding amides of the general formula BG.3 or ester BG.2 may be saponified to afford the corresponding acid which is then coupled with a benzylamine mediated by 1,1'-carbonyldiimidazole (or other suitable carboxylic acid activating agent) to provide amides of the general formula BG.3. Sonogashira coupling of BG.3 with an electron-rich acetylene (e.g. propargyl alcohol, Z=CH₂OH) provides the alkynes of the general formula BG.4. Saturation of the alkyne by hydrogenation catalyzed by palladium on carbon in alcoholic solvents affords the corresponding alkyl derivatives of the formula BG.5.

CHART BG

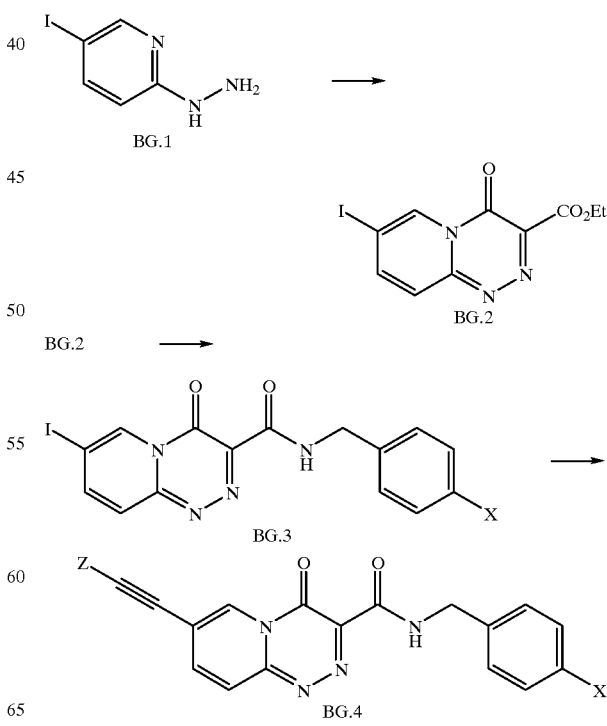

BG.4 ⟶

-continued

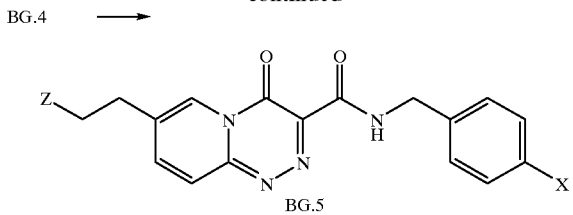

BG.5

Specific examples of heterocycle W17 in which G=4-morpholinylmethyl are prepared as described in Chart BH. Palladium catalyzed carbonylation of BG.3 in the presence of tributyltin hydride gives the corresponding aldehyde BH.1. Reductive amination of the resulting aldehyde with a primary or secondary amine (e.g. morpholine) and sodium cyanoborohydride affords the aminomethyl substituted derivatives such as those of formula BH.2.

CHART BH

BG.3 ⟶

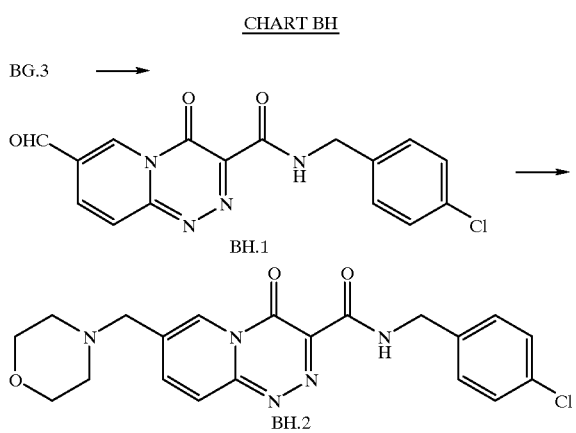

W18. 4-Hydroxy-1-benzothiophene-5-carboxamides. The preparation of specific examples of heterocycle W18 is described in Charts BI. 6,7-dihydro-1-benzthiophen-4(5H) one BI.1 is deprotonated alpha to the carbonyl by treatment with LDA at low temperature. The resulting enolate is then quenched with HMPA and methylcyano-formate (Mander, L. N.; Sethi, S. P. Tetrahedron. Lett. 1983, 24, 5425–5428.) to give β-ketoester BI.2. Bromination of BI.2 with an electophilic bromine source (e.g. bromine) provides bromide BI.3. Elimination of BI.3 is achieved using lithium carbonate in DMF at 100° C. to give benzothiophenol BI.4. Heating BI.4 in excess benzylamine (e.g. 4-chlorobenzylamine) gives amide BI.5. Treatment of BI.5 with the Mannich reagent 4-methylenemorpholin-4-ium chloride in refluxing acetonitrile (Dowle, M. D.; Hayes, R.; Judd, D. B.; Williams, C. N. Synthesis, 1983, 73–75.) affords compounds of the general formula BI.6.

Chart BI

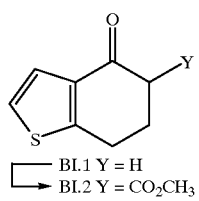

BI.1 Y = H
BI.2 Y = CO₂CH₃

-continued

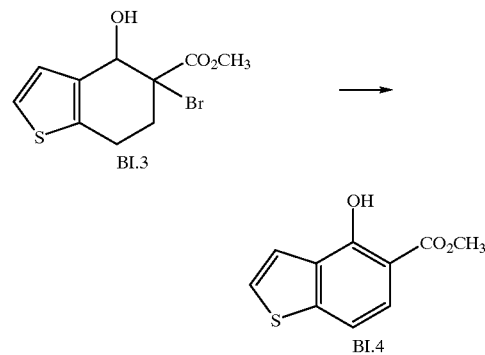

BI.4 ⟶

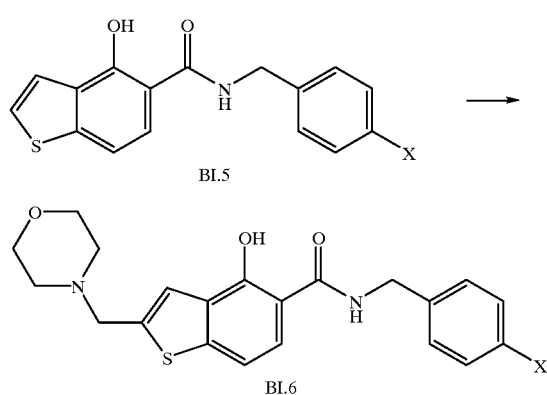

Other specific examples of heterocycle W18 in which G=3-hydroxypropyl or 3-hydroxy-1-propynyl are prepared as described in Chart BJ. Bromination of BI.5 adjacent to the sulfur using NBS in DMF affords the bromide BJ.1. Sonogashira coupling of BJ.1 with propargyl alcohol catalyzed by PdCl₂(PPh₃)₂ and copper(I) iodide either in diethylamine (Sonogashira, K.; Tohada, Y.; Hagihara, N. Tetrahedron Lett. 1975, 50, 4467.) or in a mixture of DMF and triethylamine (Fisher, M. J. et. al. J. Med. Chem. 1997, 40, 2085.) provides the corresponding alkynes of the general formula BJ.2. Saturation of these alkynes by hydrogenation catalyzed by palladium on carbon in alcoholic solvents affords alkyl derivatives BJ.3.

Chart BJ

BI.5 ⟶

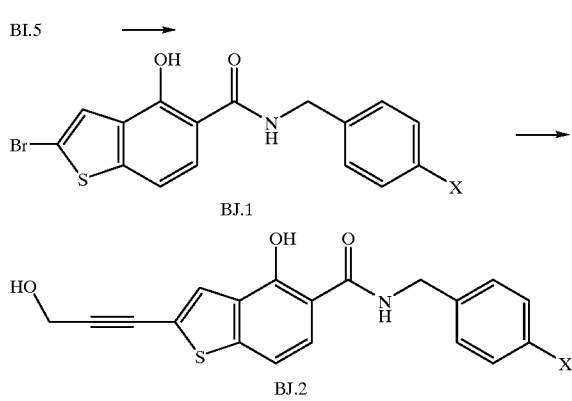

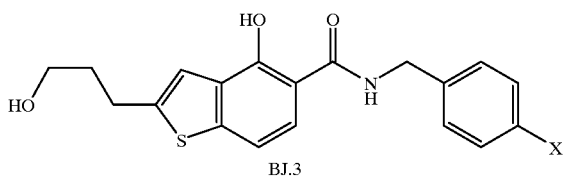

BJ.2 →

W19.1. 5-Hydroxy-5H-[1,3]thiazolo[3,2-a]pyrimidine-6-carboxamides. Specific examples of heterocycle W19.1 are prepared as described in Chart BK. Allylic bromination of thiazolopyrimadine BK.1 employing N-bromosuccinimide and benzoyl peroxide affords the halide BK.2. Displacement of the bromide leaving group by morpholine provides BK.3. The resulting ester is then saponified to afford the corresponding acid which is then coupled with a benzylamine (e.g. 4-chlorobenzylamine, 4-bromobenzylamine, or 4-fluorobenzylamine) mediated by 1,1'-carbonyldiimidazole (or other suitable carboxylic acid activating agent) to provide amides of the general formula BK4.

CHART BK

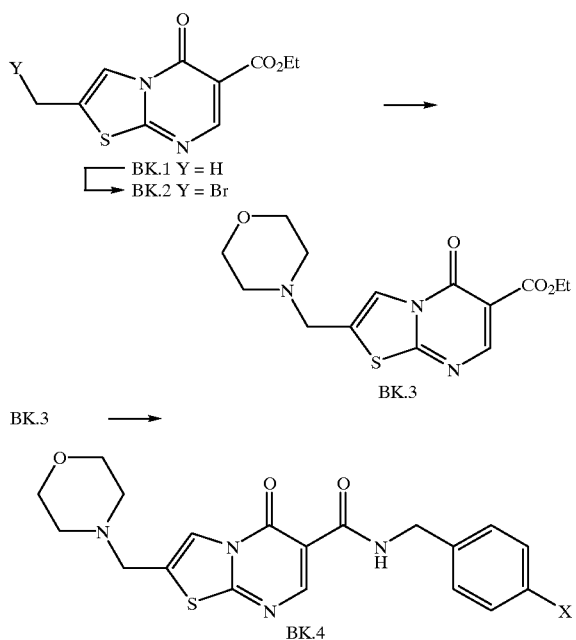

W19.2. 5-Hydroxy-5H-[1,3,4]thiadiazolo[3,2-a]pyrimidine-6-carboxamides. As described in Chart BL, (4-morpholinyl)acetic acid trifluoroacetic acid salt BL.1 (*J. Med. Chem.* 1994, 37, 4538–4554) is cyclized to the thiadiazole BL.2 with aminoguanidine in polyphosphoric acid. Condensation of BL.2 with diethyl ethoxymethylenemalonate followed by thermal cyclization affords thiadiazolopyrimidine BL.3. The resulting ester BL.3 is then saponified to afford the corresponding acid BL.4 which is then coupled with a benzylamine (e.g. 4-chlorobenzylamine) mediated by 1,1'-carbonyldiimidazole (or other suitable carboxylic acid activating agent) to provide amides of the general formula BL.5. A specific example of heterocycle W19.2 in which $R^8$=OH is also prepared as described in Chart BL. Thiadiazole BL.2 is heated in xylenes with diethyl 2-(((4-chlorobenzyl)amino) carbonyl)malonate (prepared by the reaction of 4-chlorobenzyl-amine with triethyl methanetricarboxylate) to afford thiadiazolopyrimidine BL.6.

CHART BL

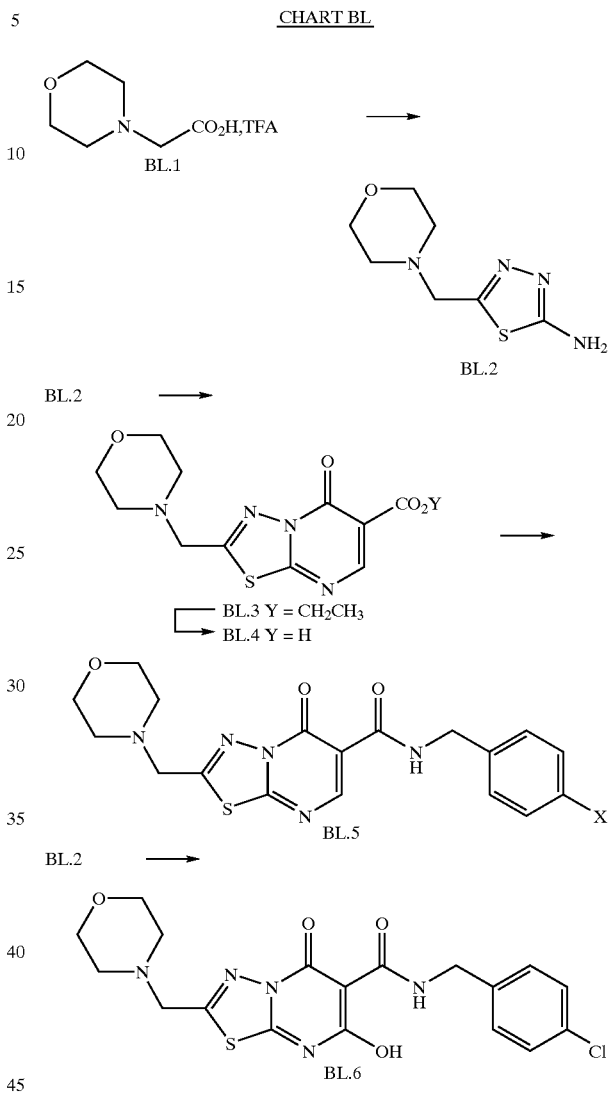

W20.1. 7-Oxo-4,7-dihydro[1,3]thiazolo[5,4-b]pyridine-6-carboxamides. Preparation of specific examples of heterocycle W20.1 follows an established literature precedent described in Chart BM (A. Haemers *J. Heterocyclic Chem.* 1984, 21, 401–406.). Morpholine is condensed with chloroacetyl chloride to afford 4-(chloroacetyl)-morpholine (BM.1) which is transformed to the dithiocarboxylate methyl ester (BM.2) by the reaction with sulfur, an amine base (e.g. triethylamine) and iodomethane. Condensation of BM.2 with aminoacetonitrile bisulfate in the presence of triethylamine affords the thiazole BM.3. Subsequent reduction of the carboxamide with borane provides BM.4 which is condensed with diethyl ethoxymethylenemalonate to give BM.5. Alkylation of the enamine nitrogen with an alkylhalide (e.g. iodomethane) or other suitable electrophile in the presence of an inorganic base affords BM.6. Cyclization of BM.6 by heating in a mixture of Eaton's reagent provides the thiazolopyridine BM.7. The resulting ester is then treated with a benzylamine (e.g. 4-chlorobenzylamine, 4-bromobenzylamine, or 4-fluorobenzylamine) at high temperature or the ester may be saponified to afford the corresponding acid which is then coupled with a benzylamine mediated by 1,1'-carbonyldiimidazole (or other suitable carboxylic acid activating agent) to provide amides of the general formula BM.8.

Chart BM

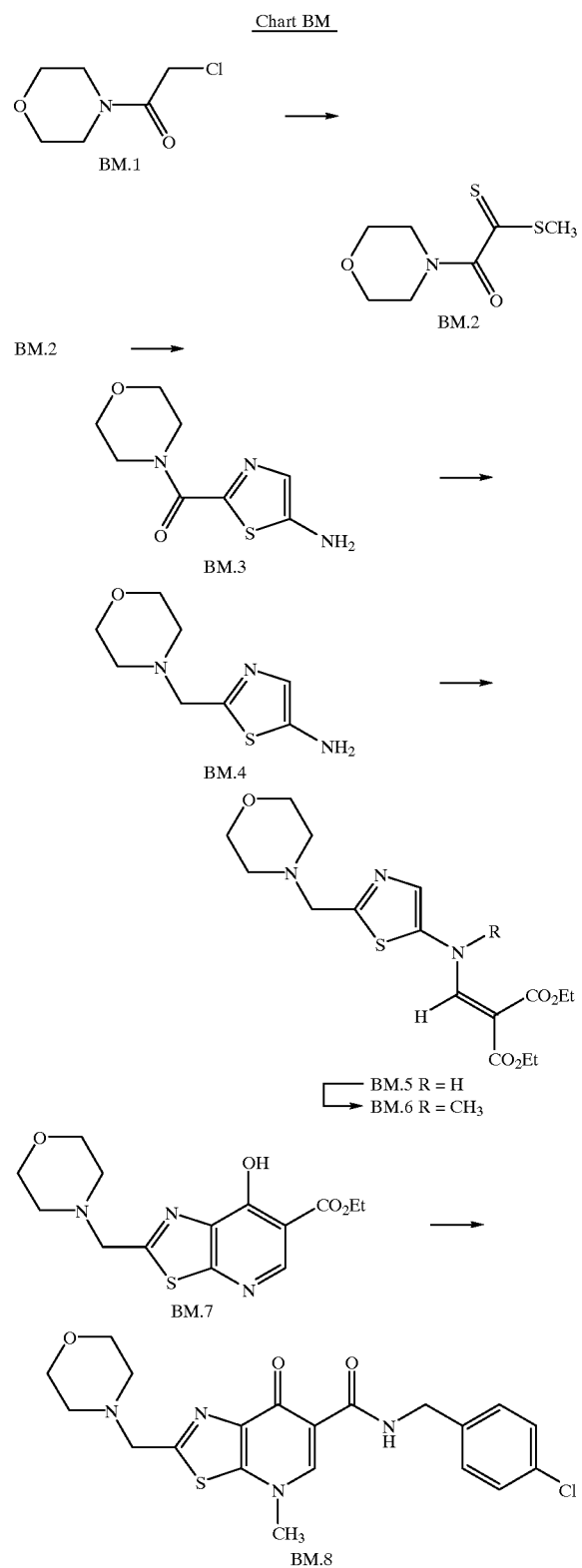

W20.2. 4-Oxo-1,4-dihydrothieno[2,3-c]pyridazine-3-carboxamides. Preparation of specific examples of heterocycle W20.2 follows an established literature precedent described in Chart BN-BO (J. Prakt. Chem. 1997, 339, 284–287.). As described in Chart BN, diazotization of β-ketoesters BN.1 (prepared as described in Chart BQ, where Y=4-morpholiylmethyl; Chart BR, where Y=bromo) with tosyl azide provides BN.2. Reductive cyclization of BN.2 with triphenylphosphine affords the thienopyridazine BN.3. The ring nitrogen atom of compound BN.3 may then be optionally substituted by a group R inclusive to the group $R^7$ consisting of a substituted or unsubstituted, alkyl or cycloalkyl group by reaction of BN.3 in the presence of a base and a species R-leaving group (e.g. iodomethane) or by the reaction of BN.3 with a species ZOH (e.g. methanol) under Mitsunobu conditions (Synthesis 1981, 1) to afford compounds of the formula BN.4. Esters BN.3 or BN.4 are then treated with a benzylamine (e.g. 4-chlorobenzylamine, 4-bromobenzylamine, or 4-fluorobenzylamine) at high temperature to afford the corresponding amides of the general formula BN.5, or alternatively, the ester is saponified to afford the corresponding acid which is then coupled with a benzylamine mediated by 1,1'-carbonyldiimidazole (or other suitable carboxylic acid activating agent) to likewise provide amides of the general formula BN.5.

CHART BN

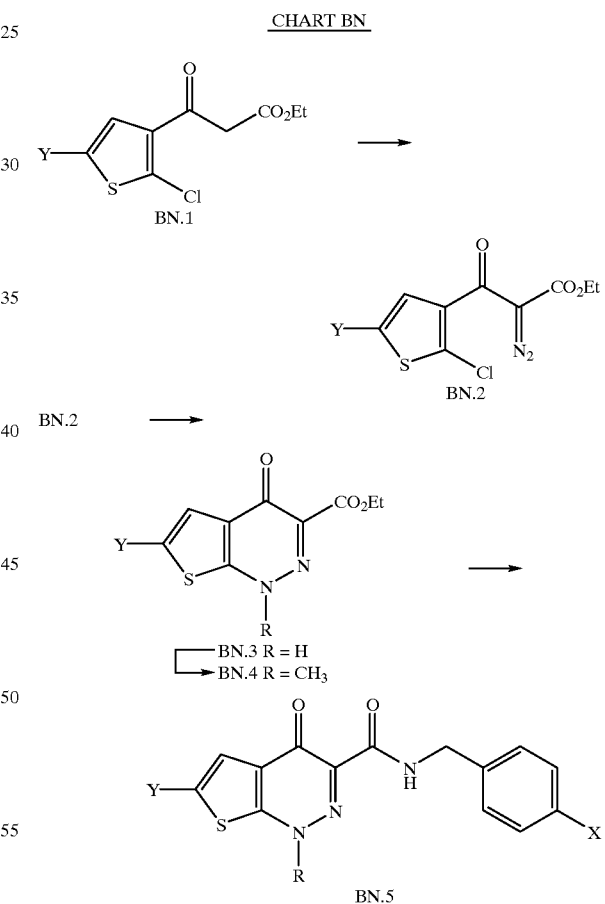

In another aspect, specific examples of heterocycle W20.2 in which $R^7$=aryl or het are prepared as described in Chart BO. Treatment of compounds of the formula BN.1 with an aryl- or heteroaryldiazonium chloride affords the hydrazone BO.1. Hydrazone BO.1 cyclizes to afford the thienopyridazine BO.2 upon treatment with an appropriate base (e.g. potassium carbonate). The resulting ester may be transformed to the corresponding carboxamides of the general formula BO.3 in a similar fashion to that described in Chart BN.

CHART BO

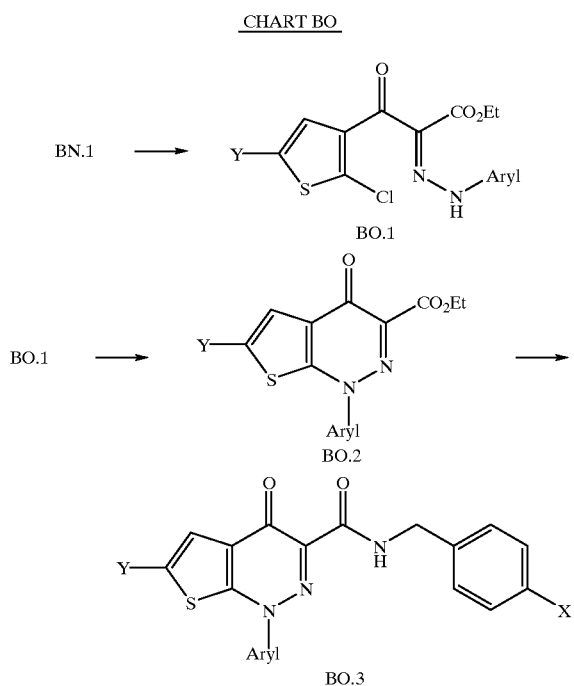

As specified in Chart BN and Chart BO, when Y=bromo, intermediates BN.5 or BO.3 may be further elaborated to provide specific examples of heterocycle W4.1 where G=3-hydroxypropyl or 3-hydroxy-1-propynyl as described in Chart BP. Intermediates BN.5 and BO.3 undergo Sonogashira coupling with an electron-rich acetylene (e.g. propargyl alcohol, Z=CH$_2$OH) catalyzed by PdCl$_2$(PPh$_3$)$_2$ and copper (I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) provides the corresponding alkynyl derivatives of formula BP.1 (Z=CH$_2$OH). Saturation of the alkyne by hydrogenation catalyzed by palladium on carbon in alcoholic solvents affords alkyl derivatives of formula BP.2 (Z=CH$_2$OH).

CHART BP

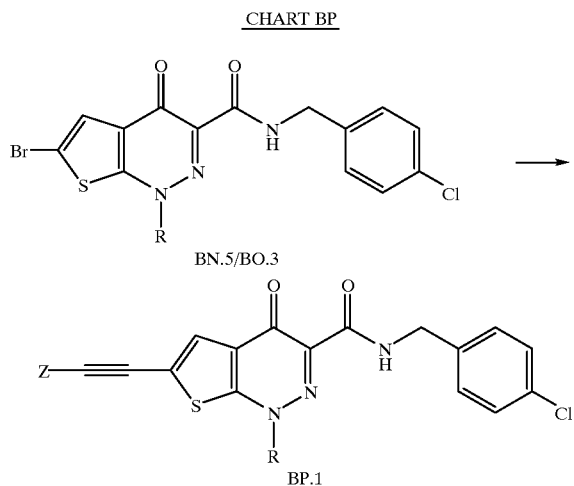

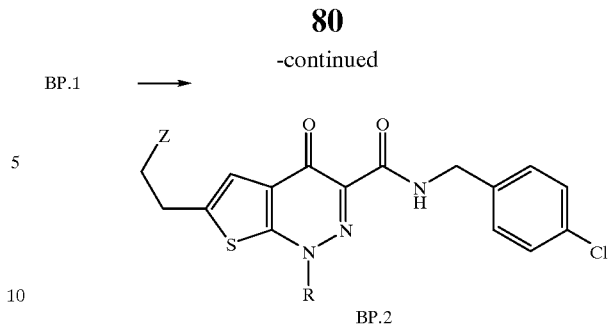

BN.1 (Y=morpholinylmethyl) is prepared according to Chart BQ. Metalation of 3-bromo-2-chlorothiophene BQ.1 (U.S. Pat. No. 5,276,025) at low temperature with lithium diisopropylamide followed by quenching with N,N-dimethylformamide and acid work-up provides thiophenecarboxaldehyde BQ.2. Reductive amination of BQ.2 with morpholine, acetic acid, and sodium triacetoxyborohydride provides the morpholinylmethyl BQ.3. Metal-halogen exchange between n-butyllithium and BQ.2 at −70° C. in diethyl ether followed by addition of the resulting aryl lithium to N-methoxy-N-methylacetamide yields the methylketone BQ.4. Treatment of BQ.4 with a base (e.g. sodium hydride) in the presence of diethylcarbonate affords the β-ketoester BN.1 (Y=morpholinylmethyl) which may then be employed as in Chart BN.

CHART BQ

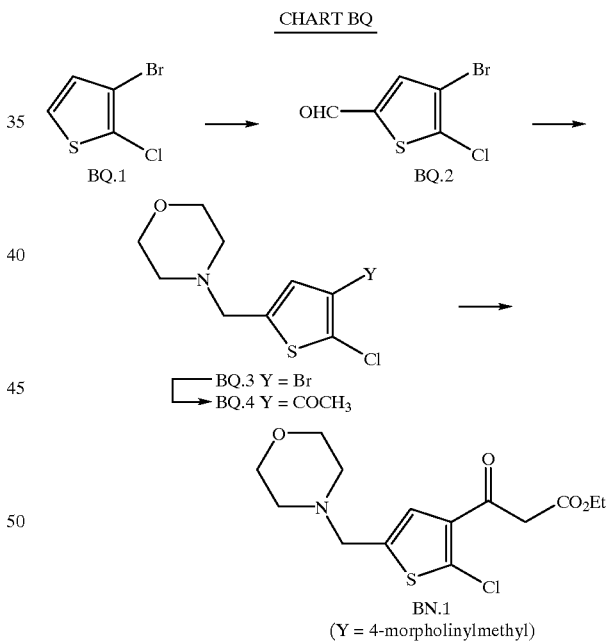

BN.1 (W=bromo) is prepared according to Chart BR. Conversion of 2-chloro-5-bromo-3-thiophenecarboxylic acid BR.1 (WO 97/11705) to its corresponding Weinreb amide with N,O-dimethylhydroxylamine according to established procedures (Einhon, J.; Einhon, C.; Luche, J. L. *Syn. Commun.* 1990, 20, 1105–1112) followed by treatment with methylmagnesium bromide provides the methylketone BR.2. Treatment of BR.2 with a base (e.g. sodium hydride) in the presence of diethylcarbonate affords the β-ketoester BN.1 (W=bromo) which may be employed as in Chart BN.

CHART BR

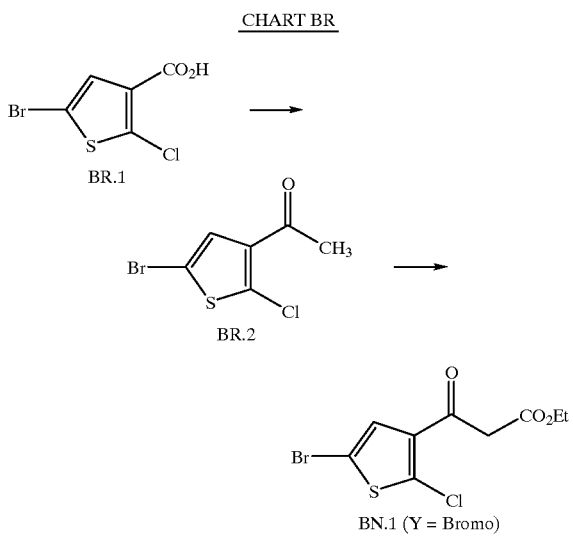

W22.2. 4-Hydroxy-1H-thieno[2,3-c][1,2]thiazine-3-carboxamide-2,2-dioxides. Representative examples of heterocyle W22.2 (G=3-hydroxy-1-propynyl or 3-hydroxypropyl) are prepared as described in Chart BS. Methyl 2-aminothiophene-carboxylate (BS.1) is converted to the corresponding sulfonamide with methane-sulfonyl chloride to afford BS.2. The sulfonamide nitrogen is then alkylated with an optionally substituted alkylhalide (e.g. iodomethane) or other appropriate electrophile in the presence of an inorganic base (e.g. potassium carbonate) to afford BS.3. Cyclization of BS.3 in the presence of a base (e.g. sodium hydride) affords the thieno-thiazine dioxide BS.4. The resulting product is then iodinated employing mercury(II) oxide and iodine or under similar halogenation conditions to afford iodide BS.5. Sonogashira coupling of BS.5 with an electron-rich acetylene (e.g. tetrahydro-2-(2-propynyloxy)-2H-pyran) provides the corresponding alkynyl derivative of the formula BS.6. Treatment of BS.6 with a benzylisocyanate (e.g. 4-chlorobenzylisocyanate) affords compounds of the formula BS.7. Deprotection of the tetrahydropyran protecting group employing standard conditions (Green, T. W.; Wuts, P. G. M. *Protective Groups in Organic Synthesis*, 1999) affords derivatives of the formula BS.8. Saturation of the alkyne by hydrogenation catalyzed by palladium on carbon in alcoholic solvents affords BS.9.

CHART BS

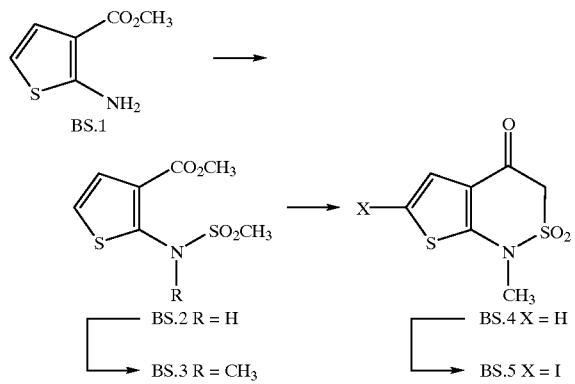

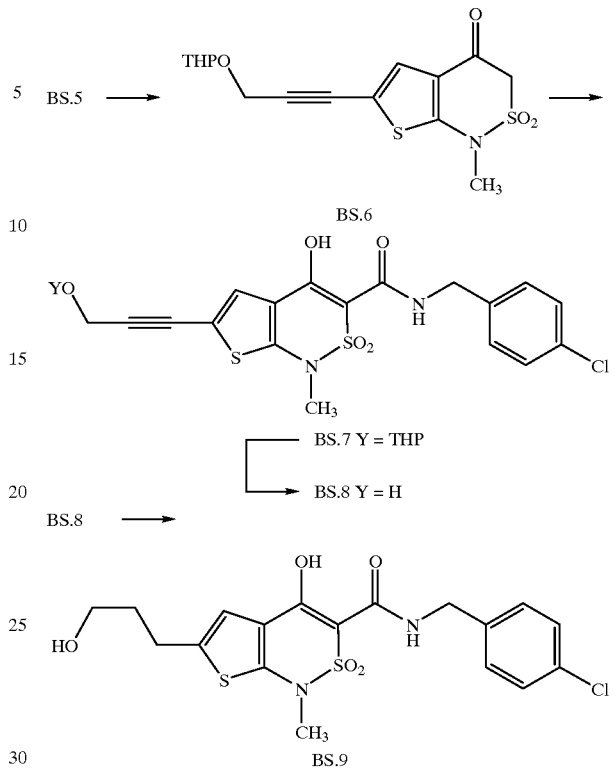

The inventive compounds may be used in their native form or as salts. In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, etoglutarate, and glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically (including but not limited to surface treatment, transdermal application, and nasal application), intravaginally, orally, or rectally, depending on whether the preparation is used to treat internal or external viral infections.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices such as the osmotic release type devices developed by the Alza Corporation under the OROS trademark.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The exact regimen for administration of the compounds and compositions disclosed herein will necessarily be dependent upon the needs of the individual subject being treated, the type of treatment and, of course, the judgment of the attending practitioner. The compounds of the present invention can be administered to an animal in need of treatment. In most instances, this will be a human being, but the treatment of livestock and companion animals is also specifically contemplated as falling within the scope of the instant invention.

The compounds of formula (I) and pharmaceutically acceptable salts thereof are useful as antiviral agents. Thus, they are useful to combat viral infections in animals, including man. The compounds are generally active against herpesviruses, and are particularly useful against the varicella zoster virus, the Epstein-Barr Virus, the herpes simplex virus types 1 and 2 (HSV-1 and 2), the human herpes virus types 6, 7 and 8 (HHV-6, 7and 8) and the human cytomegalovirus (HCMV).

The invention will be further described by the following non-limiting examples.

Preparation 1
2-Amino-5-iodopyridine [Y.2].

A mixture of 2-aminopyridine (4.0 g), periodic acid dihydrate (1.94 g), and iodine (4.31 g) is heated in a solution of acetic acid (25.5 mL), water (5.1 mL), and sulfuric acid (0.76 mL) at 80° C. for 4 h. The reaction is allowed to cool to room temperature, then poured into 300 mL of a dilute solution of sodium bisulfite. An orange solid precipitates and is filtered and discarded. The filtrate is neutralized (pH ~5–6) with saturated $NaHCO_3$ and then partitioned against $CH_2Cl_2$. The aqueous layer is further washed with $CH_2Cl_2$ (2×). The combined organic layers are dried ($Na_2SO_4$), filtered, and condensed to afford a solid. The crude product is recrystallized from ether/hexanes to afford 2.69 g (29%) of the title compound as a yellow solid. Physical characteristics: m.p. 126–129° C.; $^1$H NMR (300 MHz, DMSO-$d_6$) δ 8.04, 7.58, 6.35, 6.13; MS (ESI+) m/z 221 (M+H)$_+$; Anal. found: C, 27.40; H, 2.06; N, 12.75.

Preparation 2
Ethyl 7-iodo-4-oxo-4H-pyrido[1,2-a]pyrimidine-3-carboxylate [Y.3].

In a 3-necked round-bottom connected to a Dean-Stark trap, a solution of 2-amino-5-iodopyridine (Preparation 1, 500 mg) and diethyl ethoxymethylenemalonate (0.92 mL) is heated at 130° C. for 2 h. The reaction is cooled to room temperature. Diphenyl ether (5 mL) is added and the reaction is heated at 250° C. for 1 h. Upon cooling the mixture to room temperature, a solid precipitates and is filtered and washed with hexanes. The crude solid is adsorbed onto silica and chromatographed eluting with $CH_2Cl_2$ (2 L). Product-containing fractions are combined and concentrated to afford a solid. The crude product is recrystallized from $CH_2Cl_2$/hexanes to yield 251 mg (32%) of the title compound as a yellow solid. Physical characteristics: m.p. 166–168° C.; $^1$H NMR (300 MHz, DMSO-$d_6$) δ 9.24, 8.85, 8.38, 7.62, 4.27, 1.30; IR (drift) 1747, 1611, 1558, 1506, 1473, 1355, 1345, 1291, 1266, 1258, 1152, 1140, 1118, 840, 796 cm$^{-1}$; MS (ESI+) m/z 345; Anal. found: C, 38.37; H, 2.48; N, 8.11.

Preparation 3
N-(4-chlorobenzyl)-7-iodo-4-oxo-4H-pyrido[1,2-a] pyrimidine-3-carboxamide [Y.4].

To a solution of 4-chlorobenzylamine (0.071 mL) in toluene (1.5 mL) at 0° C. is added trimethylaluminum (2M solution in toluene, 0.29 mL). After stirring the solution at 0° C. for 5 min, ethyl 7-iodo-4-oxo-4H-pyrido[1,2-a] pyrimidine-3-carboxylate (Preparation 2, 200 mg) is added. The solution is stirred at 0° C. for an additional 10 min, then allowed to stir at room temperature overnight. The reaction mixture is poured into 3 N HCl (7.5 mL) and water, then extracted with $CH_2Cl_2$ (3×). The combined organic layers are dried ($Na_2SO_4$), filtered, and concentrated to afford a solid. The impurities are removed by dissolving the crude product in $CH_2Cl_2$ and filtering the insoluble solid. The filtrated is concentrated to afford 148 mg (58%) of title compound as a yellow solid. Physical characteristics: m.p. 191–194° C.; $^1$H NMR (300 MHz, DMSO-$d_6$) δ 9.36, 9.27, 9.03, 8.38, 7.68, 7.40, 4.57; IR (drift) 3319, 1683, 1637, 1612, 1560, 1541, 1507, 1478, 1347, 1339, 1295, 837, 792, 641, 625 cm$^{-1}$; MS (ESI+) m/z 440 (M+H)$^+$; Anal. found: C, 43.58; H, 2.48; N, 9.38.

EXAMPLE 1
N-(4-chlorobenzyl)-7-(3-hydroxy-1-propynyl)4-oxo-4H-pyrido[1,2-a]pyrimidine-3-carboxamide [Y.5]

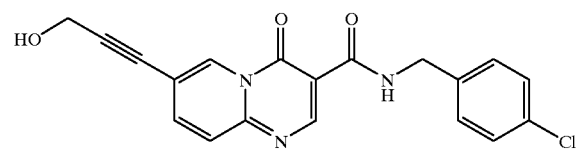

To a solution of N-(4-chlorobenzyl)-7-iodo-4-oxo-4H-pyrido[1,2-a]pyrimidine-3-carboxamide (Procedure 3, 500 mg), $PdCl_2(PPh_3)_2$ (21 mg), and $Et_3N$ (0.73 mL) in anhydrous DMF (3 mL) is added propargyl alcohol (0.094 mL). The mixture is heated at 90° C. for 1 h, then allowed to cool to room temperature. The reaction mixture is placed under high vacuum to remove the DMF. The resulting solid is dissolved in $CH_2Cl_2$ and washed with water. The aqueous layer is extracted with $CH_2Cl_2$ (2×). The combined organic layers are dried ($Na_2SO_4$), filtered, and condensed to afford a solid. The crude solid is adsorbed onto silica and chromatographed (1% MeOH/$CH_2Cl_2$ (1 L), 1.5% MeOH/$CH_2Cl_2$ (1 L), and 2% MeOH/$CH_2Cl_2$ (1.5 L)). Product-containing fractions are combined and concentrated to afford 243 mg (58%) of the title compound as a creme solid. Physical characteristics: m.p. 179–181° C.; $^1$H NMR (300 MHz, DMSO-$d_6$) δ 9.34, 9.07, 9.00, 8.10, 7.85, 7.36, 5.50, 4.54, 4.36; IR (drift) 3294, 1676, 1632, 1618, 1561, 1541, 1521, 1490, 1353, 1335, 1131, 1061, 1040, 842, 797 cm$^{-1}$; MS (ESI+) m/z 368 (M+H)$^+$; Anal. found: C, 61.96; H, 3.69; N, 11.44.

Preparation 4
5-(4-Morpholinylmethyl)-1,3,4-thiadiazol-2-ylamine [BL.2]

(4-Morpholinyl)acetic acid trifluoroacetic acid salt (1.0 g) and thiosemicarbazide (0.25g) are heated in polyphosphoric acid (2.0 g) at 70° C. for 1 h. The mixture is cooled to room temperature and basified with sodium carbonate, which is extracted with $CH_2Cl_2$. The organic layer is dried (MgSO$_4$), concentrated, and the residue is chromatographed (CH$_2$Cl$_2$/methanol, 9/1) to give 150 mg of the title compound as a white solid. Physical characteristics: MS (ESI+) m/z 201 (M+H)$^+$.

Preparation 5

Diethyl 2-(((4-Chlorobenzyl)amino)carbonyl)malonate.

Triethyl methanetricarboxylate (2.32 g) and 4-chlorobenzylamine (1.42 g) are stirred at room temperature for 16 h. Insoluble material is filtered off and the filtrate is purified by column chromatography (hexanes/acetone, 5/1) to give 1 g (12%) of the title compound as an oil which slowly solidifies. Physical characteristics: MS (ESI+) m/z 330 (M+H)$_+$. $^1$H NMR (CDCl$_3$) δ 7.70, 7.31, 7.26, 4.48, 4.38, 4.28, 1.30.

EXAMPLE 2

N-(4-chlorobenzyl)-5-hydroxy-2-(4-morpholinylmethyl)-7-oxo-7H-[1,3,4]thiadiazolo-[3,2-a]pyrimidine-6-carboxamide [BL.6].

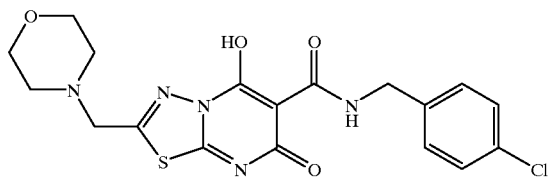

Diethyl 2-(((4-chlorobenzyl)amino)carbonyl)malonate (Preparation 5, 33 mg) and 5-(4-morpholinylmethyl)-1,3,4-thiadiazol-2-ylamine (Preparation 4, 20 mg) are dissolved in xylene and heated to reflux for 5 h. The solvent is evaporated and the residue is triturated with ether. The resulting percipitate is filtered and dried to afford 17 mg of the title compound as a brown solid. Physical characteristics: MS (ESI+) m/z 438 (M+H)$^+$. $^1$H NMR (DMSO) δ 7.42, 7.38, 4.60, 3.92, 3.62, 2.62.

Preparation 6

5-(3-(Tetrahydro-2H-pyran-2-yloxy)-1-propynyl)-2-pyridinylamine [AA.1].

2-(2-Propynyloxy)tetrahydro-2H-pyran (360 mg), 5-iodo-2-pyridinylamine (440 mg), CuI (140 mg) and dichlorobis(triphenylphosphine)palladium (60 mg) are dissolved in diethylamine (10 mL). After the mixture is stirred for 1 h at room temperature, water (40 mL) and CH$_2$Cl$_2$ (80 mL) are added. The organic layer is separated, dried (MgSO$_4$) and concentrated. The resulting residue is purified on a silica gel plate (CH$_2$Cl$_2$/methanol, 9/1) to give 230 mg (50%) of the title compound as an oil which slowly solidifies. MS (ESI+) m/z 233 (M+H)$^+$. $^1$H NMR (CDCl$_3$) δ 8.10, 7.60, 6.65, 5.90, 4.86, 4.48, 3.90, 3.5–3.6, 1.55–1.9.

Preparation 7

N-(4-chlorobenzyl)-4-hydroxy-2-oxo-7-[3-(tetrahydro-2H-pyran-2-yloxy)-1-propynyl]-2H-pyrido[1,2-a]pyrimidine-3-carboxamide [AA.2].

5-(3-(Tetrahydro-2H-pyran-2-yloxy)-1-propynyl)-2-pyridinylamine (Preparation 6, 30 mg) and diethyl 2-(((4-chlorobenzyl)amino)carbonyl)malonate (Preparation 5, 50 mg) are dissolved in xylene and heated to reflux for 3 h. The solvent is evaporated and the residue is crystallized from ether/hexanes and dried to afford 20 mg of the a brown solid. Physical characteristics: MS (ESI+) m/z 470 (M+H)$^+$. $^1$H NMR (CDCl$_3$) δ 9.80, 9.12, 7.80, 7.52, 7.32, 7.27, 4.86, 4.65, 4.51, 3.90, 3.5–3.6, 1.55–1.9.

EXAMPLE 3

N-(4-Chlorobenzyl)-4-hydroxy-7-(3-hydroxy-1-propynyl)-2-oxo-2H-pyrido[1,2-a]-pyrimidine-3-carboxamide [AA.3].

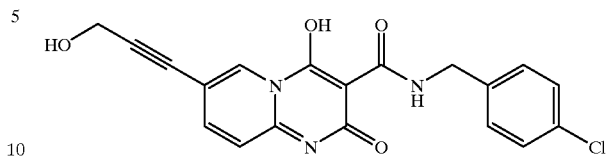

N-(4-Chlorobenzyl)-4-hydroxy-2-oxo-7-(3-(tetrahydro-2H-pyran-2-yloxy)-1-propynyl)-2H-pyrido[1,2-a] pyrimidine-3-carboxamide (Preparation 7, 12 mg) is dissolved in CH$_2$Cl$_2$ and treated with 0.5 M HCl in methanol (0.5 mL). The reaction mixture is stirred for 16 h at room temperature. The mixture is concentrated, and the residue is crystallized from ether/hexanes and dried to afford 7 mg of the title compound as a brown solid. Physical characteristics: $^1$H NMR (CD$_3$OD) δ 9.2, 8.35, 7.75, 7.4–7.5, 4.80, 4.50; MS (ESI+) m/z 386 (M+H)$^+$.

Preparation 8

Ethyl 2-methyl-5-oxo-5H-[1,3]thiazolo[3,2-a]pyrimidine-6-carboxylate [BK.1]

A mixture of 2-amino-5-methyl thiazole (1.14 g) and diethyl ethoxymethylenemalonate (2.16 g) is heated at 135° C. in xylene (20 mL) for 2 h allowing for removal of the ethanol product. After the solvent is removed, the mixture is suspended in diphenyl ether (10 mL). The mixture is then heated to reflux with removal of ethanol for 30 min. The reaction mixture is cooled to rt and hexanes (20 mL) is added. The resulting precipitate is filtered, washed with diethyl ether (2×10 mL) and dried to afford 2.1 g (86%) of the title compound as a tan solid. Physical characteristics: $^1$H NMR (DMSO) δ 8.61, 8.05, 4.25, 2.48, 1.28; MS (ESI+) m/z 239 (M+H)$^+$.

Preparation 9

Ethyl 2-(bromomethyl)-5-oxo-5H-[1,3]thiazolo[3,2-a]pyrimidine-6-carboxylate [BK.2].

A mixture of ethyl 2-methyl-5-oxo-5H-[1,3]thiazolo[3,2-a]pyrimidine-6-carboxylate (Preparation 8, 1.19 g), NBS (1.07 g) and benzoyl peroxide (25 mg) is heated to reflux in carbon tetrachloride (50 mL) for 6 h. After the mixture is cooled to rt, the precipitate is filtered. The precipitate is re-dissolved in methylene chloride (100 mL) and washed with water. The organic layer is separated, dried (MgSO$_4$), and concentrated to afford 1.0 g (60%) of the title compound as a pale yellow solid. Physical characteristics: MS (ESI+) m/z 317, 319 (M+H)$^+$. $^1$H NMR (CDCl$_3$)δ 9.80, 8.15, 4.42, 1.40.

Preparation 10

Ethyl 2-(4-morpholinylmethyl)-5-oxo-5H-[1,3]thiazolo[3,2-a]pyrimidine-6-carboxylate [BK.3].

A mixture of ethyl 2-(bromomethyl)-5-oxo-5H-[1,3]thiazolo[3,2-a]pyrimidine-6-carboxylate (Preparation 9, 159 mg) and morpholine (0.5 mL) in DMF (10 mL) is stirred for 4 h at rt. The mixture is diluted with CH$_2$Cl$_2$ (100 mL) and is washed with water. The organic layer is dried (MgSO$_4$) and concentrated to afford 130 mg (80%) of the title compound as a white solid. Physical characteristics: MS (ESI+) m/z 324 (M+H)$^+$. $^1$H NMR (DMSO) δ 8.62, 8.22, 4.25, 3.75, 3.59, 2.49, 1.28.

EXAMPLE 4

N-(4-Chlorobenzyl)-2-(4-morpholinylmethyl)-5-oxo-5H-[1,3]thiazolo[3,2-a]-pyrimidine-6-carboxamide [BK.4]

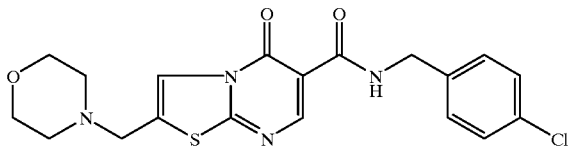

A 1 N aqueous solution of sodium hydroxide (2 mL) is added dropwise via an additional funnel to a solution of ethyl 2-(4-morpholinylmethyl)-5-oxo-5H-[1,3]-thiazolo[3,2-a]pyrimidine-6-carboxylate (Preparation 10, 80 mg) in a mixture of THF/MeOH (1/1, 6 mL). The mixture is heated to 50° C. for 1 h. The reaction mixture is then cooled to rt, and a 1 N aqueous solution of hydrochloric acid is added to adjust to pH 5. After the mixture is concentrated, the residue is suspended in a mixture of $CH_2Cl_2$/MeOH (9/1, 15 mL). The solid is filtered off and the filtrate is concentrated to give the acid as a solid (53 mg). The resulting acid is dissolved in DMF (3 mL) and treated with 1.1'-carbonyldiimidazole (48 mg). The mixture is heated to 60° C. for 18 h, is allowed to cool to rt, and is treated with 4-chlorobenzylamine (141 mg). After 2 h at rt, the mixture is taken up in $CH_2Cl_2$ (20 mL) and is washed with water. The organic layer is separated, dried ($MgSO_4$), and concentrated. The resulting residue is purified on a silica gel plate ($CH_2Cl_2$/methanol, 20/1) to give 15 mg of the title compound as a white solid. Physical characteristics: MS (ESI+) m/z 421 (M+H)$^+$. $^1$H NMR (DMSO)δ 8.75, 8.25, 7.36, 4.53, 3.76, 3.59, 2.49.

Preparation 11

Methyl 4-oxo-4,5,6,7-tetrahydro-1-benzothiophene-5-carboxylate [BI.2]

n-Butyl lithium (2.5 M, 15.8 mL) is added dropwise via syringe to a solution of diisopropyl amine (55 mL) in anhydrous THF (20 mL) at −10° C. under an atmosphere of nitrogen. After stirring for 30 min at this temperature, the solution is cooled to −78° C. and a solution of containing 6,7-dihydro-1-benzthiophen-4(5H)one (BI.1, 5.00 g) in anhydrous THF (20 mL) is added dropwise over 15 minutes. The solution is warmed to 0° C. and stirred for one hour at that temperature. After re-cooling to −78° C., HMPA (5.7 mL) and methyl-cyanoformate (3.1 mL) are sequentially added. The solution is stirred for 10 minutes at −78° C. The reaction mixture is quickly poured into cold water (100 mL) and extracted with ether (250 mL). The organic phase is washed with brine, dried over $Na_2SO_4$, filtered, and concentrated to give a red oil. This oil is chromatographed on a Biotage column eluting with 0–30% ethyl acetate in heptane (500 mL each 10%) to give 3.87 g (56%) of the title compound as a white solid. Physical characteristics. Mp. 85–86° C.; MS (ESI+) m/z 211.0 (M+H)$^+$; HRMS (FAB) m/z 211.0425 ($C_{10}H_{10}O_3S$+H). Anal. Found: C, 57.15; H, 4.84.

Preparation 12

Methyl 5-bromo-4-oxo-4,5,6,7-tetrahydro-1-benzothiophene-5-carboxylate [BI.3].

Methyl 4-oxo4,5,6,7-tetrahydro-1-benzothiophene-5-carboxylate (Preparation 11, 3.50 g) is dissolved in anhydrous ether (30 mL) and carbon tetrachloride (20 mL). This solution is cooled to −10° C. and a solution of bromine (2.66 g) in carbon tetrachloride (5 mL) with 3 drops of ether. Each drop of the bromine solution is added only after the orange color dissipated from the prior drop. After completion of addition, the solution is allowed to stir for 15 minutes at −10° C., 15 minutes at 0° C., and then overnight at rt. This reaction mixture is poured into water (100 mL) and extracted with ether (100 mL). The ether phase is washed with brine, dried over $Na_2SO_4$, filtered, and concentrated to give 4.80 g (99%) of the title compound as a yellow oil. Physical characteristics: MS (ESI+) m/z 289.0/291.0 (M+H)$^+$.

Preparation 13

Methyl 4-hydroxy-1-benzothiophene-5-carboxylate [BI.4].

A solution containing methyl 5-bromo4-oxo-4,5,6,7-tetrahydro-1-benzothiophene-5-carboxylate (Preparation 12, 1.18 g) and lithium carbonate (1.81 g) in anhydrous DMF (10 mL) is heated at 100° C. overnight. After cooling, the solids are removed by filtration and the filtrate is partitioned between ethyl acetate (50 mL) and water (50 mL). The organic layer is washed with brine, dried over $Na_2SO_4$, filtered, and concentrated to give a brown solid. This crude product is chromatographed on a Biotage column eluting with 0–20% ethyl acetate in heptane (250 mL each 10%) to give 270 mg (32%) of the title compound as a white solid. Physical characteristics: Mp 94–95° C.; MS (ESI−) m/z 207.0 (M−H)$^-$. Anal. found: C, 57.26; H, 3.88; N, 0.17.

Preparation 14

N-(4-Chlorobenzyl)-4-hydroxy-1-benzothiophene-5-carboxamide [BI.5, X=Cl].

A mixture of 4-chlorobenzylamine (1 mL) and methyl 4-hydroxy-1-benzothiophene-5-carboxylate (Preparation 13, 0.50 g) is heated to 120° C. under an atmosphere of nitrogen for 4 hours. After cooling, the residue is diluted with ethyl acetate and methanol (1:1) and absorbed onto silica gel. Chromatography on a Biotage column eluting with 500 mL of toluene gave 520 mg (68%) of the title compound as a white solid. Physical characteristics: Mp 168–169° C.; MS (ESI−) m/z 316.1 (M−H)$^-$. Anal. Found: C, 60.82; H, 3.87; N, 4.33.

EXAMPLE 5

N-(4-Chlorobenzyl)-4-hydroxy-2-(4-morpholinylmethyl)-1-benzothiophene-5-carboxamide [BI.6, X=Cl].

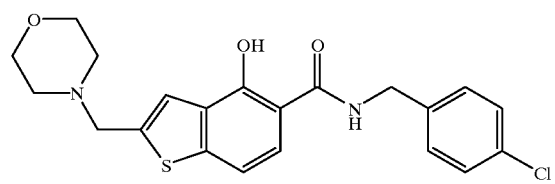

A mixture of N-(4-chlorobenzyl)-4-hydroxy-1-benzothiophene-5-carboxamide (Preparation 14, 0.15 g), 4-methylenemorpholin4-ium chloride (0.13 g), and anhydrous acetonitrile (5 mL) is heated at reflux for 2 hours. Upon cooling, a saturated solution of sodium bicarbonate is added until the pH=9 and this solution is partitioned between ethyl acetate (50 mL) and water (50 mL). The organic layer is washed with brine, dried over $Na_2SO_4$, filtered, and concentrated to give a pink oil. Chromatography on a Biotage column eluting with 20% ethyl acetate in heptane (250 mL) and 50% ethyl acetate in heptane (500 mL) affords 140 mg (76%) of the title compound as a white solid. Physical characteristics: Mp 200° C.; MS (ESI+) for $C_{21}H_{21}ClN_2O_3S$ m/z 417 (M+H)$^+$.

EXAMPLE 6
N-(4-Chlorobenzyl)-6-(3-hydroxy-1-propynyl)-4-oxo-4H-chromene-3-carboxamide [AN.4, Z=CH$_2$OH].

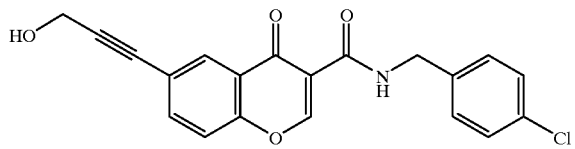

A mixture of 6-bromo-3-formylchromone (1.2 g) and N-bromosuccinimide (0.82 g) in carbon tetrachloride (30 mL) is irradiated with a sun lamp (625 watt) for 20 minutes. The cooled reaction is then treated with 4-chlorobenzylamine (2 mL) and stirred 30 minutes. The resulting amide intermediate is purified by chromatography on silica gel 60 in ethyl acetate/CH$_2$Cl$_2$ mixtures and then recrystallized from CH$_2$Cl$_2$/hexane. (54%, M.p. 182–183° C.) A portion of the resulting amide (0.2 g) in dioxane is combined under argon with bis(benzonitrile) palladium (II) chloride (6 mg), copper(I) iodide (4 mg), a 0.5 M solution of tri-t-butylphosphine in cyclohexane (0.064 mL), diisopropylamine (0.085 mL), and propargyl alcohol (0.037 mL). The reaction is stirred at room temperature overnight. The mixture is diluted with ethyl acetate and filtering. The crude product is purified by column chromatography on silica gel 60 in ethyl acetate/CH$_2$Cl$_2$ mixtures and is then crystallized from methanol/CH$_2$Cl$_2$/ethyl acetate to afford the title compound (23%). Physical characteristics: m.p. 185–186° C. $^1$H NMR (CDCl$_3$) δ 1.95, 4.52, 4.62, 7.30, 7.50, 7.75, 8.27, 8.98, 9.63; MS (ESI) [M+Na]$^+$ 390.

Preparation 15
Ethyl 3-(2-fluoro-5-iodophenyl)-3-oxopropanoate [AT.1, Y=Iodo]

Employing the method utilized by Wang (Wang, X., Monte, W. T., Napier, J. J., Ghannam, A. *Tetrahedron. Lett.* 1994, 35, 9323), 1,1'-carbonyldiimidazole (1.82 g) in THF (20 mL) at 0° C. is treated with 2-fluoro-5-iodobenzoic acid (2.66 g) prepared according to literature procedures (Blackburn, B. K., Lee, A., Baier, M., Kohl, B., Olivero, A. G., Matamoros, R., Robarge, K. D., McDowell, R. S. *J. Med Chem.* 1997, 40, 717–729.) in portions over a 10 minute period. The mixture is stirred for 1 h and then allowed to warm to room temperature for an additional 1 h. The solution is then added dropwise into an enolate solution of ethyl trimethylsilymalonate at 5° C. prepared by the addition of DBU (3.35 g) to a solution of ethyl trimethylsilylmalonate (2.25 g) in acetonitrile (20 mL) at 5° C. with stirring for 45 minutes. The reaction mixture is allowed to warm to room temperature and stirred overnight. The orange solution is quenched with 100 mL of aqueous 10% citric acid solution and extracted with ethyl acetate. The organic extract is washed with aqueous 10% sodium bicarbonate solution and water, dried (Na$_2$SO$_4$), and concentrated in vacuo to give 2.4 g of the title compound as a yellow liquid. Physical characteristics: tlc R$_f$=0.66 (silica gel G; 20% EtOAc/hexane, visualize with I$_2$).

Preparation 16
Ethyl 3-(2-fluoro-5-iodophenyl)-2-(hydroxyimino)-3-oxopropanoate [AT.2, Y=Iodo]

Employing the method utilized by Fray (Fray, J. M., Cooper, K., Parry, M. J., Richardson, K., Steele, J. *J. Med. Chem.* 1995, 38, 3514–3523), a solution of sodium nitrite (0.52 g) in water (3 mL) is added dropwise to a solution of ethyl 3-(2-fluoro-5-iodophenyl)-3-oxopropanoate (Preparation 15, 2.4 g) in glacial acetic acid (3 mL) at 5° C. with stirring. After 1.5 h, the mixture is poured into saturated aqueous sodium chloride and extracted with dichloromethane. The organic extracts are washed with saturated aqueous sodium chloride and saturated aqueous sodium bicarbonate, dried (Na$_2$SO$_4$), and concentrated in vacuo to give a sticky oil which is flash chromatographed on silica gel (230–400 mesh, 10 g) eluting with 20% ethyl acetate and hexane to give, after concentration of product fractions, 1.31 g of the title compound as a yellow liquid (~3/1 ratio of oxime isomers). Physical characteristics: MS (ESI+) m/z 366 (M+H)$^+$.

Preparation 17
Ethyl 6-Iodo-4-oxo-4H-1,2-benzoxazine-3-carboxylate [AT.3, Y=Iodo].

A solution of ethyl 3-(2-fluoro-5-iodophenyl)-2-(hydroxyimino)-3-oxopropanoate (Preparation 16, 1.3 g) in toluene (20 mL) is heated to reflux under nitrogen for 48 h. The reaction mixture is cooled to room temperature and concentrated in vacuo to give 1.33 g of a crude yellow solid which is recrystallized from ether to afford 0.65 g of the title compound as a yellow crystalline solid. Physical characteristics: mp 130–131: $^1$H NMR (300 MHz, CDCl$_3$) δ 1.45, 4.51, 7.35, 8.09, 8.50; IR (drift) 2475, 2425, 2382, 2350, 2260, 1742, 1663, 1456, 1332, 1240, 1195, 1150, 1010, 987, 831 cm$^{-1}$; HRMS (FAB) m/z 345.9581 (C$_{11}$H$_8$INO$_4$+H). Anal. Found: C, 38.03; H, 2.52; N, 4.06.

Preparation 18
N-(4-Chlorobenzyl)-6-iodo-4-oxo-4H-1,2-benzoxazine-3-carboxamide [AT.4, Y=Iodo].

A mixture of ethyl 6-iodo-4-oxo4H-1,2-benzoxazine-3-carboxylate (Preparation 17, 48 mg) and 4-chlorobenzylamine (41 mg) and toluene (1 mL) is heated to 100° C. for 2 minutes. The mixture is cooled and concentrated in vacuo, and the residue is crystallized from ethanol-ether mixture to give 0.60 g (48%) of the title compound. Physical characteristics: mp 188–190° C.; $^1$H NMR (400 MHz, DMSO-d$_6$) δ 4.49, 7.41, 7.59, 8.25, 8.32, 9.2; IR (drift) 3284, 1680, 1656, 1599, 1571, 1490, 1453, 1433, 1199, 1158, 928, 921, 819, 782, 619 cm$^{-1}$; MS (FAB) m/z 441 (MH$^+$, 65); HRMS (FAB) m/z 440.9507 (C$_{16}$H$_{10}$ClIN$_2$O$_3$+H). Anal. Found: C, 43.56; H, 2.43; N, 6.32; Cl, 8.04.

EXAMPLE 7
N-(4-Chlorobenzyl)-6-(3-hydroxy-1-propynyl)-4-oxo-4H-1,2-benzoxazine-3-carboxamide [AU. 1].

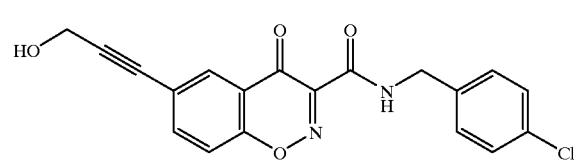

Under an argon atmosphere, a mixture of N-(4-chlorobenzyl)-6-iodo-4-oxo-4H-1,2-benzoxazine-3-carboxamide (Preparation 18, 0.117 g), dichlorobis(triphenyl-phosphine)palladium (12.8 mg), copper(I) iodide (3.7 mg), and triethylamine (1 mL) in THF (6 mL) is cooled in an ice-brine bath. A solution of propargyl alcohol (32 mg) in THF (3 mL) is added slowly via a syringe to the reaction mixture. The reaction mixture is stirred at ice-brine temperature for 2 h and then allowed to warm to room temperature overnight. The mixture is concentrated in vacuo and the residue is flash chromatographed on silica gel (230–400 mesh, 8 g), eluting with 1% methanol in dichloromethane, pooling desirable fractions and concentrating in vacuo provides the title compound as a pale yellow solid. Physical characteristics: m.p. 117–120° C.; $^1$H NMR (400 MHz, DMSO-d$_6$) δ 4.35, 4.50, 5.55, 7.42, 7.77, 7.97, 9.4; $^{13}$C NMR (DMSO-d$_6$) δ 49.2, 49.3, 67.8, 79.4, 81.8, 91.8, 117.5, 119.8, 120.2, 126.6, 128.3, 129.0, 131.6, 137.2, 138.8, 155.2, 159.2, 160.3, 165.2; MS (FAB) m/z 369 (MH$^+$, 99); HRMS (FAB) m/z 369.0645 (C$_{19}$H$_{13}$ClN$_2$O$_4$+H).

Preparation 19
Ethyl 3-(2-chloro-5-iodo-3-pyridinyl)-2-diazo-3-oxopropanoate [P.2, Y=Iodo].

A mixture of 5-iodo-2-hydroxynicotinic acid (8.04 g) and thionyl chloride (50 mL) is heated to reflux overnight under nitrogen. The solution is cooled to room temperature and concentrated in vacuo at 60° C. to give 9.2 g of the crude acid chloride. The resulting acid chloride is dissolved in chloroform (5 mL), cooled to 5° C., and then treated with ethyl diazoacetate (8.65 g) in small portions over a 2 minute period. After stirring at 5° C. for 1 h, the reaction mixture is heated to 55° C. for 2 h and then cooled to room temperature. The reaction mixture is concentrated at 50° C. under high vacuum to give 11.13 g of a yellow liquid. Flash chromatography on silica gel (53 g) eluting with 10% ethyl acetate/hexane followed by crystallization from hexane at room temperature affords 7.13 g (62%) of the title compound. Physical characteristics: mp 84–85° C.; $^1$H NMR (300 MHz, CDCl$_3$) δ 1.20, 4.22, 7.89, 8.68; IR (drift) 2149, 1714, 1624, 1405, 1383, 1373, 1327, 1281, 1235, 1167, 1141, 1109, 954, 903, 771 cm$^{-1}$; MS (FAB) m/z 380 (MH$^+$, 99); HRMS (FAB) m/z 379.9296 (C$_{10}$H$_7$ClN$_3$O$_3$+H). Anal. Found: C, 31.31; H, 1.92; N, 10.55; Cl, 9.86.

Preparation 20
Ethyl 3-(2-chloro-5-iodo-3-pyridinyl)-2-hydrazono-3-oxopropanoate.

Triphenylphosphine(1.95 g) is added in one portion to a solution of ethyl 3-(2-chloro-5-iodo-3-pyridinyl)-2-diazo-3-oxopropanoate (Preparation 19, 2.57 g) in diisopropyl ether (25 mL) and chloroform (15 mL) at room temperature. The yellow solution is stirred under nitrogen for 18 h. The mixture is then treated with water (0.125 mL), heated to reflux for 2 h, and then stirred overnight at room temperature. The mixture is filtered, and the solids are washed with hexane and dried to give 1.83 g of the title compound. After concentration, the filtrate is purified by flash chromatography on silica gel eluted with 10% ethyl acetate/hexane to provide an additional 0.36 g to yield a combined total of 2.19 g (85%) of the title compound as a pale yellow solid. Physical characteristics: $^1$H NMR (300 MHz, CDCl$_3$) δ 1.39, 1.63, 4.38, 7.94, 8.63; IR (drift) 3378, 3182, 1675, 1651, 1568, 1564, 1483, 1324, 1303, 1286, 1199, 923, 770, 664, 620 cm$^{-1}$; MS (ESI+) m/z 382 (M+H)$^+$. Anal. Found: C, 31.78; H, 2.43; N, 10.91; Cl, 9.63.

Preparation 21
Ethyl 6-iodo-4-oxo-1,4-dihydropyrido[2,3-c]pyridazine-3-carboxylate [P.3, Y=Iodo].

A mixture of ethyl 3-(2-chloro-5-iodo-3-pyridinyl)-2-hydrazono-3-oxopropanoate (Preparation 20, 1.0 g) and sodium bicarbonate (0.33 g) in 1,4-dioxane (15 mL) is heated to reflux for 24 h. The reaction mixture is cooled to room temperature and concentrated in vacuo to give a slurry which is treated with water (ca. 1 mL), ethyl acetate (ca. 3 mL), and hexane (ca. 2 mL). The mixture is filtered and the solid is washed with aq. ethanol (2 mL) to give, from several crops, a total of 0.48 g (54% yield) of the title compound. Physical characteristics: mp 238–242° C.; $^1$H NMR (300 MHz, DMSO-d$_6$) δ 1.30, 4.23, 8.73, 8.93; IR (drift) 1675, 1561, 1526, 1468, 1390, 1374, 1339, 1313, 1304, 1249, 1209, 1158, 1141, 826, 601 cm$^{-1}$; MS (ESI-) m/z 344 (M-H)$^-$; HRMS (FAB) m/z 345.9692 (C$_{10}$H$_8$IN$_3$O$_3$+H).

Preparation 22
N-(4-Chlorobenzyl)-6-iodo-4-oxo-1,4-dihydropyrido[2,3-c]pyridazine-3-carboxamide [P.4, X=Cl, Y=Iodo].

A mixture of ethyl 6-iodo-4-oxo-1,4-dihydropyrido[2,3-c]pyridazine-3-carboxylate (Preparation 21, 0.40 g) and 4-chlorobenzylamine (2 mL) is heated under argon to 100° C. for 4 h. The mixture is cooled to room temperature and diluted with ethyl acetate (10 mL), and the resulting suspension is filtered and washed with ether to give 0.50 g of a mixture of product and starting amine impurity. The mixture is suspended in ethanol and water at room temperature and the solid is collected by filtration to give 0.12 g of the title compound as an off-white solid. Physical characteristics: mp>300° C.; $^1$H NMR (300 MHz, DMSO-d$_6$) δ 4.58, 7.39, 8.84, 8.95, 11.0; IR (drift) 1640, 1559, 1542, 1514, 1493, 1454, 1357, 1325, 1273, 1263, 1169, 823, 814, 791, 645 cm$^{-1}$; MS (ESI-) for m/z 439 (M-H)$^{31}$; HRMS (FAB) m/z 440.9608 (C$_{15}$H$_{10}$ClIN$_4$O$_2$+H).

Preparation 23
N-(4-Chlorobenzyl)-6-iodo-1-methyl-4-oxo-1,4-dihydropyrido[2,3-c]pyridazine-3-carboxamide [P.5, X=Cl, Y=Iodo].

Iodomethane (0.6 mL) is added to a mixture of N-(4-chlorobenzyl)-6-iodo-4-oxo-1,4-dihydropyrido[2,3-c]pyridazine-3-carboxamide (Preparation 22, 0.196 g) and triethyl-amine (70 μL) in acetonitrile (10 mL) and the mixture is stirred at room temperature for 48 h. The reaction mixture is concentrated, and the residue is dissolved in chloroform and water. The organic phase is dried (Na$_2$SO$_4$) and concentrated in vacuo. The crude product is purified by flash chromatography on silica gel (240–400 mesh, 7 g) eluting with 2% methanol/chloroform. The product fractions are pooled and concentrated in vacuo to give 0.16 g of the title compound as a yellow solid. Physical characteristics: mp 207–208° C.; $^1$H NMR (400 MHz, CDCl$_3$) δ 4.39, 4.70, 7.33, 9.0, 9.1, 10.0; IR (drift) 1676, 1608, 1574, 1550, 1493, 1470, 1397, 1393, 1370, 1320, 1267, 1257, 812, 673, 666 cm$^{-1}$; MS (EI) m/z 454 (M$^+$, 61); HRMS (FAB) m/z 454.9767 (C$_{16}$H$_{12}$ClIN$_4$O$_2$+H). Anal. Found: C, 42.10; H, 2.61; N, 12.22.

EXAMPLE 8
N-(4-Chlorobenzyl)-6-(3-hydroxy-1-propynyl)-1-methyl-4-oxo-1,4-dihydropyrido [2,3-c] pyridazine-3-carboxamide [R.1, R=CH$_3$, Z=CH$_2$OH].

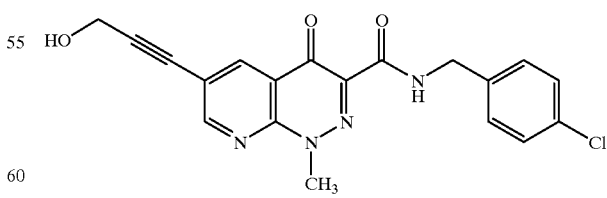

Under an argon atmosphere, a mixture of N-(4-chlorobenzyl)-6-iodo-1-methyl4-oxo-1,4-dihydropyrido[2,3-c]pyridazine-3-carboxamide (Preparation 23, 0.053 g), dichlorobis(triphenylphosphine)palladium (II) (4.1 mg), copper(I) iodide (18.3 mg), and diethylamine (1.5 mL) is treated with a solution of propargyl alcohol (11 μL). The reaction mixture is stirred at room temperature overnight. The mixture is diluted with EtOAc and then filtered through a Celite-packed, sintered-glass funnel. The cake is washed with CHCl$_3$ until the washings are colorless. The organic filtrate is washed with aqueous saturated ammonium chloride and water, dried (Na$_2$SO$_4$) and concentrated in vacuo. The crude solid is triturated with ether, filtered and washed with ether to give 0.032 g (71%) of the title compound as a light brown solid. Physical characteristics: mp 201–206° C.; $^1$H NMR (400 MHz, DMSO-d$_6$) δ 4.21, 4.39, 4.54, 5.51, 7.40, 8.52, 9.0, 9.7; IR (drift) 3368, 1660, 1612, 1597, 1551, 1479, 1410, 1397, 1377, 1353, 1256, 1036, 812, 674, 650 cm$^{-1}$; MS (EI) m/z 382 (M$^+$, 6); HRMS (FAB) m/z 383.0917 (C$_{19}$H$_{15}$ClN$_4$O$_3$+H).

Preparation 24
4-(Chloroacetyl)morpholine [BM.1]

To a stirring mixture of morpholine (1.00 g) and triethylamine (1.6 mL) in EtOAc (10 mL) at 0° C. is added chloroacetyl chloride (1.83 mL) dropwise. The mixture is stirred at 0° C. for 35 min., diluted with 10% HCl (25 mL) and extracted with EtOAc (3×50 mL). The organic layer is dried over MgSO$_4$, and the solvent removed. The residue is purified by SiO$_2$ flash column chromatography (eluent 35% EtOAc/hexane) to afford 1.42 g (76%) of the title compound as a yellow liquid. Physical characteristics: $^1$H NMR (CDCl$_3$) δ 3.54, 3.64, 3.72, 4.07; IR (liq.) 2859, 1654, 1463, 1438, 1302, 1270, 1251, 1233, 1115, 1069, 1040, 965, 790, 657, 604 cm$^{-1}$; MS (ESI+) m/z 164 (M+H)$^+$. Anal. Found: C, 43.66; H, 6.17; N, 8.58.

Preparation 25
Methyl 4-Morpholinyl(oxo)ethanedithioate [BM.2]

To a stirring mixture of sulfur (4.86 g) and triethylamine (23.02 mL) in DMF (30 mL) at ambient temperature is added 4-(chloroacetyl)morpholine (Preparation 24, 12.36 g) in DMF (15 mL). The mixture is stirred for 2 h, cooled to 0° C., and iodomethane (5.19 mL) added. The mixture is stirred for an additional 2 h while warming to ambient temperature. The mixture is diluted with water (150 mL) and extracted with EtOAc (3×100 mL). The organic layer is dried over MgSO$_4$, and the solvent removed. The residue is purified via SiO$_2$ flash column chromatography (eluent 35% EtOAc/hexane) to afford 4.44 g (29%) of the title compound as an orange oil. Physical characteristics: $^1$H NMR (CDCl$_3$) δ 2.75, 3.45, 3.69, 3.76; IR (liq.) 2916, 2855, 1640, 1456, 1438, 1275, 1250, 1136, 1113, 1070, 1042, 980, 809, 701, 663 cm$^{-1}$; MS (ESI+) m/z 206 (M+H)$^+$; HRMS (FAB) m/z 206.0311 (C$_7$H$_{11}$NO$_2$S$_2$+H).

Preparation 26
2-(4-Morpholinylcarbonyl)-1,3-thiazol-5-amine [BM.3]

To a stirring mixture of methyl 4-morpholinyl(oxo)ethanedithioate (Preparation 25, 500 mg) and aminoacetonitrile bisulfate (564 mg) in MeOH (10 mL) at 0° C. is added triethylamine in MeOH (5 mL). The mixture is stirred overnight and allowed to warm to ambient temperature. The solution is filtered, and solvent removed from the filtrate. The residue is washed with water (15 mL) and extracted with EtOAc (3×20 mL), dried over MgSO$_4$, and the solvent removed. The residue is purified by SiO$_2$ flash column chromatography (eluent 3/1 EtOAc/hexane) to afford 161 mg (31%) of the title compound as a light brown solid. Physical characteristics: $^1$H NMR (CDCl$_3$) δ 3.78, 4.35, 7.05; IR (diffuse reflectance) 3321, 3217, 2858, 1580, 1438, 1418, 1348, 1276, 1178, 1113, 1003, 834, 783, 731, 619 cm$^{-1}$; MS (ESI+) m/z 214 (M+H)$^+$. Anal. Found: C, 45.24; H, 5.33; N, 19.42.

Preparation 27
2-(Morpholin-4-ylmethyl)-1,3-thiazol-5-amine [BM.4]

To a solution of 2-(4-morpholinylcarbonyl)-1,3-thiazol-5-amine (Preparation 26, 1.0 g) in THF (10 mL) under nitrogen at ambient temperature is added borane (1.0 M solution in THF, 9.39 mL). The bright yellow mixture is heated to reflux (85° C.) for 1 h. The mixture is cooled to ambient temperature, quenched with aq. NH$_4$Cl, and extracted with EtOAc (3×75 mL). The organic layer is dried (MgSO$_4$) and the solvent removed. The residue is purified by column chromatography (eluent 2% MeOH/CH$_2$Cl$_2$) to afford 329 mg (35%) of the title compound as a yellow oil. Physical characteristics: $^1$H NMR (CDCl$_3$) δ 2.49, 3.61, 3.65, 6.84; MS (ESI+) m/z 200 (M+H)$^+$.

Preparation 28
Diethyl 2-(((2-(Morpholin-4-ylmethyl)-1,3-thiazol-5-yl)amino)methylene)malonate [BM.5]

To a solution of 2-(morpholin-4-ylmethyl)-1,3-thiazol-5-amine (Preparation 27, 1.13 g) in pyridine (10 mL) at 45° C. is added diethyl ethoxymethylenemalonate (2.26 mL). The mixture is stirred overnight, diluted with water (100 mL), and extracted with EtOAc (3×75 mL). The organic layer is dried (MgSO$_4$) and the solvent removed. The residue is purified by column chromatography (eluent 50% EtOAc/hexane) to afford 1.51 g (86%) of the title compound as a brown oil. Physical characteristics: $^1$H NMR (CDCl$_3$) δ 1.27–1.37, 2.58, 3.72, 3.73, 4.20–4.30, 8.10, 11.02; IR (diffuse reflectance) 1687, 1637, 1596, 1416, 1337, 1301, 1274, 1268, 1243, 1234, 1114, 1094, 1011, 867, 801 cm$^{-1}$; HRMS (FAB) m/z 370.1420 (C$_{16}$H$_{23}$N$_3$O$_5$S+H). Anal. Found: C, 51.80; H, 6.32; N, 11.26.

Preparation 29
Diethyl 2-((Methyl(2-(morpholin-4-ylmethyl)-1,3-thiazol-5-yl)amino)methylene)-malonate [BM.6]

To a mixture of diethyl 2-(((2-(morpholin4-ylmethyl)-1,3-thiazol-5-yl)amino)-methylene)malonate (Preparation 28, 1.51 g) and K$_2$CO$_3$ (1.19 g) in DMF (15 mL) at ambient temperature is added iodomethane (0.28 mL). The mixture is heated to 75° C. in a sealed pressure tube and stirred overnight. The solution is cooled to ambient temperature and the solvent is removed. The mixture is diluted with water (75 mL) and extracted with EtOAc (3×75 mL). The organic layer is dried (MgSO$_4$) and the solvent removed to afford 0.984 g (63%) of the title compound as a light brown solid. Physical characteristics: $^1$H NMR (CDCl$_3$) δ 1.24–1.33, 2.60, 3.31, 3.74, 4.17–4.24, 7.60; IR (liq.) 1702, 1608, 1535, 1453, 1383, 1365, 1293, 1270, 1232, 1206, 1117, 1096, 1071, 1010, 865 cm$^{-1}$; HRMS (FAB) m/z 384.1600 (C$_{17}$H$_{25}$N$_3$O$_5$S+H). Anal. Found: C, 53.18; H, 6.64; N, 10.41.

Preparation 30
Ethyl 4-Methyl-2-(morpholin-4-ylmethyl)-7-oxo-4,7-dihydro[1,3]thiazolo[5,4-b]pyridine-6-carboxylate [BM.7]

A mixture of Eaton's Reagent (1.5 mL) and diethyl 2-((methyl(2-(morpholin-4-yl-methyl)-1,3-thiazol-5-yl)amino)methylene)malonate (Preparation 29, 452 mg) is heated to 110° C. for 20 min. with a stream of nitrogen over the reaction. The mixture is cooled to ambient temperature and transferred to a cooled beaker. The solution is diluted with ice chips and neutralized by dropping Na$_2$CO$_3$ into the solution. The mixture is then extracted with CH$_2$Cl$_2$ (3×50 mL), the organic layer dried (MgSO$_4$), and the solvent is removed. The residue is purified by column chromatography (eluent 5% MeOH/CH$_2$Cl$_2$) to afford 11 mg (28%) of the title compound as a brown solid. Physical characteristics: $^1$H NMR (CDCl$_3$) δ 1.39, 2.67, 3.77, 3.89, 3.90, 4.38, 8.25; IR (diffuse reflectance) 1726, 1716, 1679, 1632, 1614, 1609, 1586, 1507, 1330, 1300, 1236, 1194, 1113, 863, 801 cm$^{-1}$. Anal. Found (C$_{15}$H$_{19}$N$_3$O$_4$S.0.75 H$_2$O): C, 51.34; H, 5.94; N, 11.88.

EXAMPLE 9
N-(4-Chlorobenzyl)-4-methyl-2-(morpholin-4-ylmethyl)-7-oxo-4,7-dihydro[1,3]-thiazolo[5,4-b]pyridine-6-carboxamide [BM.8]

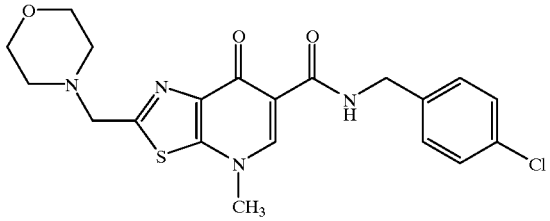

A mixture of ethyl 4-methyl-2-(morpholin-4-ylmethyl)-7-oxo-4,7-dihydro[1,3]-thiazolo[5,4-b]pyridine-6-carboxylate (Preparation 30, 105 mg) and 4-chlorobenzylamine (1 mL) is heated to 190° C. for 40 min. and then allowed to cool to ambient temperature. The solvent is removed in vacuo. The mixture is diluted with ether to precipitate 89 mg (66%) of the title compound as a tan solid. Physical characteristics: $^1$H NMR (DMSO-d$_6$) δ 2.59, 3.64, 3.91, 4.00, 4.56, 7.33–7.36, 8.75, 10.59; IR (diffuse reflectance) 2857, 2809, 1662, 1599, 1569, 1550, 1531, 1526, 1517, 1492, 1346, 1296, 1116, 797, 732 cm$^{-1}$. Anal. Found: C, 55.50; H, 4.98; N, 12.00.

Preparation 31
Methyl 2-((Methylsulfonyl)amino]thiophene-3-carboxylate [BS.2]

To a stirring solution of methyl-2-aminothiophene carboxylate (10 g) in CH$_2$Cl$_2$ (350 ml) at 0° C. is added triethylamine (13.51 g). Methanesulfonyl chloride (15.28 g) is then added dropwise at 0° C. over 15 min. The mixture is stirred for 16 h allowing the solution to warm to ambient temperature. The organic layer is washed with water (100 ml) and dried over MgSO$_4$. The solvent is removed in vacuo to afford a crude residue. This material is dissolved in MeOH (400 ml) and a solution of NaOMe in methanol is added (2.92 g Na metal in 150 ml MeOH) at ambient temperature. The resulting heterogeneous mixture is stirred at ambient temperature overnight. The mixture is concentrated to approximately 150 mL volume, cooled to 0° C., and filtered to afford 14.5 g (88%) of the title compound as a tan solid (Na salt). Physical characteristics: $^1$H NMR (DMSO-d$_6$) δ 2.68, 3.61, 6.23, 6.91; IR (diffuse reflectance) 1683, 1507, 1464, 1316, 1248, 1233, 1222, 1190, 1150, 1124, 1075, 979, 787, 763, 685 cm$^{-1}$; MS (CI) m/z 258 (MH$^+$).

Preparation 32
Methyl 3-(Methyl(methylsulfonyl)amino)thiophene-2-carboxylate [BS.3]

To a stirring mixture of methyl 2-((methylsulfonyl)amino]thiophene-3-carboxylate (Preparation 31, 12.06 g) and K$_2$CO$_3$ (14.89 g) in DMF at ambient temperature is added iodomethane (3.2 mL). The resulting mixture is stirred at ambient temperature overnight and the solvent removed in vacuo. The residue is suspended between water/EtOAc (100 mL each). The organic layer is separated and dried over MgSO$_4$. The solvent is removed and the residue recrystallized from Et$_2$O to afford 11.62 g (90%) of the title compound as a light green solid. Physical characteristics: $^1$H NMR (CDCl$_3$) δ 2.97, 3.31, 3.87, 7.15, 7.45; IR (diffuse reflectance) 1712, 1531, 1443, 1343, 1334, 1290, 1243, 1203, 1153, 988, 978, 864, 771, 759, 717 cm$^{-1}$; MS (EI) m/z 249 (M$^+$); Anal. Found: C, 38.51; H, 4.43; N, 5.66.

Preparation 33
1-Methyl-1H-thieno[2,3-c][1,2]thiazin-4(3H)-one 2,2-Dioxide [BS.4]

To a stirring solution of methyl 3-(methyl(methylsulfonyl)amino)thiophene-2-carboxylate (Preparation 32, 7.0 g) in DMF (150 ml) at 0° C. is added NaH (3.37 g, 60% dispersion) portionwise. After complete addition, the mixture is allowed to stir overnight while slowly warming to ambient temperature. The resulting mixture is cooled to 0° C. and MeOH (20 ml) is slowly added. The mixture is stirred for 20 min and then the solvent is removed. The residue is suspended between EtOAc/10% HCl (100 mL each). The organic layer is separated and dried over MgSO$_4$. The solvent is removed in vacuo and the residue is recrystallized from EtOAc to afford 3.46g (57%) of the title compound as a yellow solid. Physical characteristics: $^1$H NMR (CDCl$_3$) δ 3.43, 4.44, 6.81, 7.33; IR (diffuse reflectance) 3105, 2975, 2910, 1667, 1512, 1475, 1411, 1342, 1294, 1248, 1162, 1134, 1040, 785, 750 cm$^-$; MS (EI) m/z 217 (M$^+$); Anal. Found: C, 38.78; H, 3.31; N, 6.41.

Preparation 34
6-Iodo-1-methyl-1H-thieno[2,3-c][1,2]thiazin-4(3H)-one 2,2-Dioxide [BS.5]

To a stirring solution of 1-methyl-1H-thieno[2,3-c][1,2]thiazin-4(3H)-one 2,2-dioxide (Preparation 33, 1.0 g) in CHCl$_3$ (100 ml) at ambient temperature is added HgO (1.19 g) and iodine (1.17 g). The resulting mixture is stirred overnight at ambient temperature and the solids removed by filtration through diatomaceous earth. The solvent is removed in vacuo and the residue purified via flash column chromatography (4/1, hexanes/EtOAc) to afford 0.68 g (43%) of the title compound as a tan solid. Physical characteristics: $^1$H NMR (CDCl$_3$) δ 3.40, 4.20, 7.53; IR (diffuse reflectance) 2986, 1675, 1664, 1505, 1478, 1405, 1338, 1327, 1275, 1245, 1177, 1158, 1129, 818, 781 cm$^{-1}$; MS (EI) m/z 343 (M$^+$). Anal. Found: C, 24.65; H, 1.82; N, 4.08.

Preparation 35
1-Methyl-6-(3-(tetrahydro-2H-pyran-2-yloxy)prop-1-ynyl)-1H-thieno[2,3-c][1,2]-thiazin-4(3H)-one 2,2-Dioxide [BS.6]

To a stirring mixture of 6-iodo-1-methyl-1H-thieno[2,3-c][1,2]thiazin-4(3H)-one 2,2-dioxide (Preparation 34, 1.0 g), triethylamine (1.5 mL) CuI (13.8 mg), and tetrahydro-2-(2-propynyloxy)-2H-pyran (0.49g) in toluene (50 mL) at ambient temperature is added tetrakis triphenylphosphine palladium (40 mg). The resulting mixture is stirred overnight at ambient temperature. MeOH (50 mL) is added, the mixture is stirred 20 min and the solvent is removed in vacuo. The residue is partitioned between 10% HCl/H$_2$O/EtOAc (100 ml each), and the organic layer is separated. The solvent is removed in vacuo and the residue purified by flash column chromatography (4/1, hexanes/EtOAc) to afford 0.68 g (66%) of the title compound as a white solid. Physical characteristics: $^1$H NMR (CDCl$_3$) δ 1.52–1.86, 3.39, 3.55, 3.84, 4.21, 4.45, 4.81, 7.38; MS (ESI–) m/z 354 (M–H)$^-$. Anal. Found: C, 50.70; H, 4.89; N, 3.95.

Preparation 36
N-(4-Chlorobenzyl)4-hydroxy-1-methyl-6-(3-(tetrahydro-2H-pyran-2-yloxy)prop-1-ynyl)-1H-thieno[2,3-c][1,2]thiazine-3-carboxamide 2,2-Dioxide [BS.7]

To a stirring solution of 1-methyl-6-(3-(tetrahydro-2H-pyran-2-yloxy)prop-1-ynyl)-1H-thieno[2,3-c][1,2]thiazin-4(3H)-one 2,2-dioxide (Preparation 35, 0.64 g) and triethylamine (0.27 g) in DMSO (15mL) at ambient temperature is added 4-chloro-benzylisocyanate (0.45 g). The resulting red solution is stirred overnight at ambient temperature and diluted with 10% aqueous HCl (20 mL). The aqueous layer is extracted with EtOAc (3×25 ml). The combined organic layers are dried over $MgSO_4$ and concentrated in vacuo. The residue is dissolved in EtOAc (15 mL) and allowed to stand at ambient temperature overnight. The resulting solid is collected by filtration, washed with EtOAc (10 ml) and dried in vacuo at 50° C. to afford 0.29 g (31%) of the title compound as a tan solid. Physical characteristics: $^1$H NMR ($CDCl_3$) δ 1.58–1.82, 3.49, 3.60, 3.89, 4.50, 4.56, 4.86, 7.30, 7.42, 7.71, 15.62; IR (diffuse reflectance) 3353, 2945, 1615, 1581, 1541, 1493, 1431, 1366, 1345, 1308, 1296, 1276, 1183, 1119, 1031 $cm^{-1}$; MS (EI) m/z 522 ($M^+$). Anal. Found: C, 53.17; H, 4.49; N, 5.67.

EXAMPLE 10
N-(4-Chlorobenzyl)-4-hydroxy-6-(3-hydroxyprop-1-ynyl)-1-methyl-1H-thieno[2,3-c][1,2]thiazine-3-carboxamide 2,2-Dioxide [BS.8]

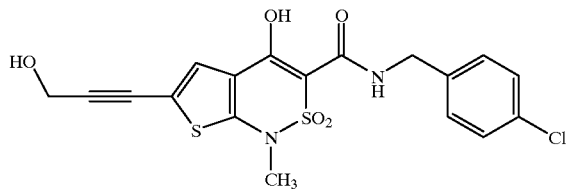

To a stirring suspension of N-(4-chlorobenzyl)-4-hydroxy-1-methyl-6-(3-(tetrahydro -2H-pyran-2-yloxy)prop-1-ynyl)-1H-thieno[2,3-c][1,2]thiazine-3-carboxamide 2,2-dioxide (Preparation 36, 0.20 g) in MeOH (20 mL) at ambient temperature is added p-toluenesulfonic acid monohydrate (0.030 g). The resulting solution is heated at 60° C. for 45 min. The mixture is cooled to 0° C. and the resulting solid is filtered to afford 0.087g (52%) of the title compound as a white solid. Physical characteristics; $^1$H NMR (DMSO-$d_6$) δ 3.44, 4.30, 4.48, 7.35, 7.37, 8.50; IR (diffuse reflectance) 3354, 1618, 1570, 1538, 1493, 1436, 1367, 1351, 1304, 1291, 1189, 1151, 1092, 1015, 815 $cm^{-1}$; MS (EI) m/z 438 ($M^+$). Anal. Found: C, 49.23; H, 3.49; N, 6.38.

Preparation 37
Methyl ((5-Methyl-2-nitrophenyl)sulfonyl)acetate [BX.2]

A solution of methyl [(5-methyl-2-nitrophenyl)sulfanyl]acetate (4.70 g) in MeOH (20 mL) is stirred at 0° C. under nitrogen and a solution of 64% m-chloroperoxybenzoic acid (25.81 g) in THF (120 mL) is added. The mixture is stirred for 20 hours at room temperature and then heated to 50° C. for 3 hours. Most of the solvent is removed by rotary evaporation under reduced pressure at room temperature until the mixture is a slurry. $CH_2Cl_2$ (400 mL) is added and the solution washed with 1M $Na_2SO_4$ solution (2×200 mL) and then saturated $NaHCO_3$ (2×200 mL). The organic layer is dried ($Na_2SO_4$), filtered, and evaporated to a thick oil. The crude material is chromatographed with EtOAc/Heptane (30–40% gradient) and then recrystallized from EtOAc/Heptane to obtain 4.30 g (81%) of the title compound as a pale yellow solid. Physical characteristics: MS (ESI−) m/z 272 (M−H).

Preparation 38
Methyl ((2-Amino-5-methylphenyl)sulfonyl)acetate [BX.3]

Palladium (10%) on carbon is added to a solution of methyl ((5-methyl-2-nitro-phenyl)sulfonyl)acetate (Preparation 37, 2.0 g) in MeOH (60 mL) and the solution is shaken on a Parr apparatus under 30 psi of hydrogen. After 3 hours the solution is filtered through Celite and the filter cake eluted with MeOH (60 mL). The combined MeOH eluant is evaporated and the remaining residue placed under high vacuum overnight to obtain 1.76 g (99%) of the title compound as a dark solid. Physical characteristics: MS (ESI+) m/z 244 (M+H).

Preparation 39
Methyl 6-Methyl-1H-4,1,2-benzothiadiazine-3-carboxylate 4,4-Dioxide [BX.4]

A solution of methyl ((2-amino-5-methylphenyl)sulfonyl)acetate (Preparation 38, 1.5 g) in glacial acetic acid (20 mL) is added dropwise with vigorous stirring to a mixture of sodium nitrite (0.47 g) in water (6 mL) at room temperature. The mixture is stirred for 1 h. The resulting precipitate is filtered and washed with excess water. The solid is collected and placed under high vacuum overnight to obtain 1.05 g (67%) of the title compound as a green powder. Physical characteristics: MS (ESI−) m/z 253 (M−H).

Preparation 40
Methyl 1,6-Dimethyl-1H-4,1,2-benzothiadiazine-3-carboxylate 4,4-Dioxide [BX.5]

Potassium carbonate (2.25 g) and iodomethane (0.60 g) is added to a solution of methyl 6-methyl-1H-4,1,2-benzothiadiazine-3-carboxylate 4,4-dioxide (Preparation 39, 0.83 g) in DMF (20 mL). The mixture is stirred at room temperature for 5 hours and then added to $CH_2Cl_2$ (120 mL) and washed with water (4×100 mL). The organic layer is dried with $Na_2SO_4$, filtered and the solvent evaporated. The crude solid is recrystallized (1% $CH_2Cl_2$/MeOH) to obtain 0.74 g (85%) of the title compound as a yellow crystalline solid. Physical characteristics: MS (ESI+) m/z 269 (M+H).

Preparation 41
Methyl 1-Methyl-6-(4-morpholinylmethyl)-1H-4,1,2-benzothiadiazine-3-carboxylate 4,4-Dioxide [BX.7]

N-Bromosuccinimide (0.239 g) and methyl 1,6-dimethyl-1H-4,1,2-benzothiadiazine-3-carboxylate 4,4-dioxide (Preparation 40, 0.30 g) are dissolved in dichloroethane (100 mL). The solution is exposed to light from a 650 W sunlamp with stirring for 25 minutes. The solvent is evaporated and the crude solid obtained is dissolved in DMF (8 mL). Morpholine (0.43 g) is added and the mixture is stirred for 3 hours. The mixture is poured into $CH_2Cl_2$ (200 mL) and washed with water (3×200mL). The organic layer is dried with $Na_2SO_4$, filtered and the solvent evaporated. The crude solid is chromatographed with MeOH/$CH_2Cl_2$ (1–5%) to obtain 0.23 g (59%) of the title compound as an off-white solid. Physical characteristics: MS (ESI+) m/z 254 (M+H).

EXAMPLE 11

N-(4-Chlorobenzyl)-1-methyl-6-(4-morpholinylmethyl)-1H-4,1,2-benzothiadiazine-3-carboxamide 4,4-Dioxide [BX.8]

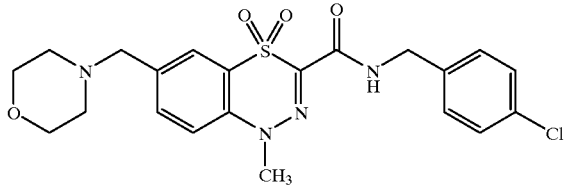

4-Chlorobenzylamine (0.66 mL) and a 0.5 M solution of NaOMe in CH$_3$OH (0.060 mL) is added to a solution of methyl 1-methyl-6-(4-morpholinylmethyl)-1H-4,1,2-benzothiadiazine-3-carboxylate 4,4-dioxide (Preparation 41, 0.16 g) in CH$_3$OH (15 mL) at room temperature. The mixture is heated for 12 hours at 70° C. and then the solvent is evaporated. The crude material is triturated with CH$_3$CN and the organic layer is decanted. The remaining solid is chromatographed with MeOH/CH$_2$Cl$_2$ (1-5%) to obtain 0.174 g (83%) of the title compound as a white solid. Physical characteristics: MS (ESI+) m/z 463 (M+H).

Preparation 42

Diethyl 2-(((2-Chloro-6-methyl-3-pyridinyl)amino)methylene) malonate [BT.2]

A mixture of 2-chloro-6-methyl-3-pyridinylamine (8.5 g) and diethyl ethoxy-methylenemalonate (22.0 mL) is heated at 140° C. for 18 hours. The mixture is cooled to room temperature and the resulting solids are recrystallized from a mixture of heptane (400 mL) and CH$_2$Cl$_2$ (2 mL) to obtain 17.9 g (95%) of the title compound as a pale red solid. Physical characteristics: MS (ESI+) m/z 313 (M+H).

Preparation 43

Ethyl 8-Chloro-6-methyl-4-oxo-1,4-dihydro[1,7]naphthyridine-3-carboxylate [BT.3]

A mixture of diethyl 2-(((2-chloro-6-methyl-3-pyridinyl)amino)methylene) malonate (Preparation 42, 0.59 g) is added to diphenyl ether (15 mL) and the mixture is degassed by alternately bubbling in nitrogen then subjecting to high vacuum. The mixture is heated rapidly to reflux and after 30 minutes cooled to room temperature. Diphenyl ether is distilled away under high vacuum and the residue taken up in CH$_2$Cl$_2$ (40 mL). The solid is collected by filtration and washed with CH$_2$Cl$_2$ with a second crop obtained by reducing the solvent volume of CH$_2$Cl$_2$ filtrate and collecting more solid. The title compound is obtained as a pale green powder, 0.24 g (47%). Physical characteristics: MS (ESI+) m/z 267 (M+H).

Preparation 44

Ethyl 8-Chloro-1,6-dimethyl-4-oxo-1,4-dihydro[1,7]naphthyridine-3-carboxylate [BT.4]

Ethyl 8-chloro-6-methyl-4-oxo-1,4-dihydro[1,7]naphthyridine-3-carboxylate (Preparation 43, 1.86 g) is dissolved in DMF (20 mL) and K$_2$CO$_3$ (2.4 g) is added followed by iodomethane (1.28 g) at room temperature. The mixture is stirred for 5 hours and then added to water (120 mL). The solid is washed with additional water, collected and dried under high vacuum to obtain 0.72 g (37%) of the title compound as a pale green powder. Physical characteristics: MS (ESI+) m/z 281 (M+H).

Preparation 45

Ethyl 8-Chloro-1-methyl-6-(4-morpholinylmethyl)-4-oxo-1,4-dihydro[1,7]-naphthyridine-3-carboxylate [BT.6]

Ethyl 8-chloro-1,6-dimethyl-4-oxo-1,4-dihydro[1,7]naphthyridine-3-carboxylate (Preparation 44, 0.62 g) and N-bromosuccinimide (0.45 g) are dissolved in dichloroethane (100 mL). The solution is subjected to light by shining a 650 W sunlamp with stirring for 25 minutes. Solvent is evaporated and the crude solid obtained is dissolved in DMF (15 mL). Morpholine (0.86 g) is added and the mixture stirred for 18 hours. The mixture is poured into CH$_2$Cl$_2$ (200 mL) and then washed with water (3×200 mL). The organics are dried with Na$_2$SO$_4$, filtered and the solvent evaporated. The crude solid is chromatographed with MeOH/CH$_2$Cl$_2$ (0–5%) to obtain 0.32 g (40%) of the title compound as a light orange solid. Physical characteristics: MS (ESI+) m/z 366 (M+H).

EXAMPLE 12

8-Chloro-N-(4-chlorobenzyl)-1-methyl-6-(4-morpholinylmethyl)-4-oxo-1,4-dihydro-1,7]naphthyridine-3-carboxamide [BT.7]

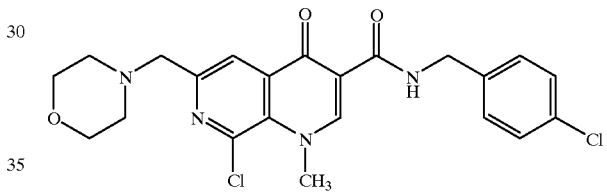

Ethyl 8-chloro-1-methyl-6-(4-morpholinylmethyl)-4-oxo-1,4-dihydro[1,7]-naphthyridine-3-carboxylate (Preparation 45, 0.11 g) is dissolved in CH$_2$Cl$_2$ (5 mL) and 4-chlorobenzylamine (0.073 mL) added followed by 0.20 mL of a 2.0M solution of AlCl$_3$ in toluene at room temperature. After 3 hours the mixture is partitioned between CH$_2$Cl$_2$ (30 mL) and water (30 mL). The organics are dried with Na$_2$SO$_4$, filtered and solvent evaporated. The remaining solid is chromatographed with MeOH/CH$_2$Cl$_2$ (1–4%) to obtain 0.110 g (79%) of the title compound as a yellow solid. Physical characteristics: MS (ESI+) m/z 461 (M+H).

Preparation 46

Ethyl-1-methyl-6-(4-morpholinylmethyl)-4-oxo-1,4-dihydro[1,7]naphthyridine-3-carboxylate [BU.1]

A mixture of ethyl-8-chloro-1-methyl-6-(4-morpholinylmethyl)-4-oxo-1,4-dihydro-[1,7]naphthyridine-3-carboxylate (Preparation 45, 0.090 g), potassium acetate (0.015 g) and 10% Pd/C (20 mg) in isopropyl alcohol is hydrogenated (balloon) for 18 hours. The mixture is filtered through celite and the filter cake washed with MeOH. The solvent is evaporated and the crude solid chromatographed with CH$_2$Cl$_2$\CH$_3$OH\TEA (90\9\1) to obtain 0.58 g (70%) of the title compound as an off-white solid. Physical characteristics: MS (ESI+) m/z 332 (M+H).

EXAMPLE 13

N-(4-Chlorobenzyl)-1-methyl-6-(4-morpholinylmethyl)-4-oxo-1,4-dihydro[1,7]-naphthyridine-3-carboxamide [BU.2]

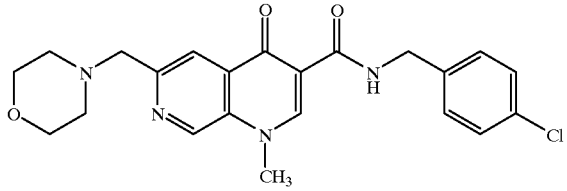

At 0° C., a solution of 2.0M AlCl₃ in toluene (0.14 mL) is added to a solution of 4-chlorobenzylamine (0.044 mL) in CH₂Cl₂ (5 mL). The compound from ethyl-1-methyl-6-(4-morpholinylmethyl)-4-oxo-1,4-dihydro[1,7]naphthyridine-3-carboxylate (Preparation 46, 0.058 g) is added and the mixture allowed to stir at room temperature for 3 hours at which time the mixture is partitioned between CH₂Cl₂ (30 mL) and water (30 mL). The organics are dried with Na₂SO₄, filtered and the solvent evaporated. The remaining solid is chromatographed with MeOH/CH₂Cl₂ (1–4%) to obtain 0.049 g (67%) of the title compound as an off-white solid. Physical characteristics: MS (ESI+) m/z 427 (M+H).

Preparation 47

Ethyl 4-Hydroxy-6,8-dimethyl-1,7-naphthyridine-3-carboxylate [BV.3]

A mixture of 2,6-dimethyl-3-aminopyridine (0.85 g) and diethyl ethoxymethylenemalonate (1.53 g) is heated at 135° C. in xylene (30 mL) for 2 h allowing for removal of ethanol. After the solvent is removed, the mixture is suspended in diphenyl ether (15 mL). The mixture is then heated to reflux with removal of ethanol for 30 min. The reaction mixture is cooled to room temperature and hexanes (20 mL) is added. The resulting precipitate is filtered, washed with diethyl ether (2×10 mL) and dried to give 0.5 g (30%) of the title compound as a brown solid. Physical chracteristics: MS (ESI+) m/z 247 (M+H)⁺; ¹H NMR (DMSO) δ 8.67, 7.97, 4.38, 2.85,2.67, 1.40.

Preparation 48

Ethyl 1,6,8-Trimethyl-4-oxo-1,4-dihydro-1,7-naphthyridine-3-carboxylate [BV.4]

Ethyl 4-hydroxy-6,8-dimethyl-1,7-naphthyridine-3-carboxylate (Preparation 47, 460 mg) is dissolved in DMF (30 mL) and treated with Na₂CO₃ (396 mg). Iodomethane (0.3 mL) is slowly added to the mixture, and it is then heated to reflux for 1 h. The reaction mixture is cooled to room temperature, quenched with water (20 mL) and extracted with CH₂Cl₂ (50 mL). The organic layer is separated, dried (MgSO₄), and concentrated in vacuo. The residue is purified by silica gel column chromatography (5% methanol/CH₂Cl₂) to give 100 mg (21%) of the title compound as a white solid. Physical characteristics: MS (ESI+) m/z 261 (M+H)⁺; ¹H NMR (DMSO) δ 8.61, 7.78, 4.23, 4.18, 3.00, 2.56, 1.28.

EXAMPLE 14

N-(4-Chlorobenzyl)-1-methyl-6,8-bis(morpholin-4-ylmethyl)-4-oxo-1,4-dihydro-1,7-naphthyridine-3-carboxamide [BV.6]

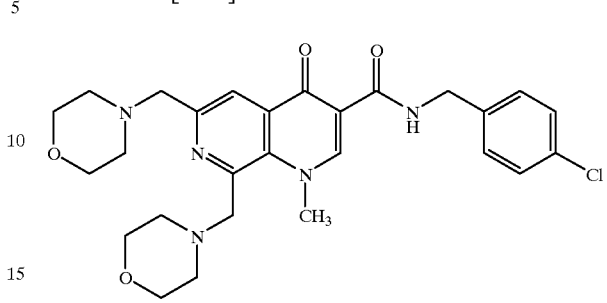

A mixture of ethyl 1,6,8-trimethyl-4-oxo-1,4-dihydro-1,7-naphthyridine-3-carboxylate (Preparation 48, 78 mg) and NBS (164 mg) is irradiated with a 650 W halogen lamp in dichloroethane (15 mL) for 15 min. After the mixture is cooled to room temperature, it is diluted with CH₂Cl₂ (20 mL) and washed with water. The organic layer is separated, dried (MgSO₄), and concentrated to give a residue which is redissioved in DMF (10 mL) and treated with morpholine (0.5 mL) at room temperature for 20 min. The mixture is diluted with CH₂Cl₂(20 mL) and washed with water. The organic layer is separated, dried (MgSO₄), and concentrated to give a residue which is purified on silica gel (5% methanol/CH₂Cl₂) to give the corresponding ester (30 mg) as a white solid. This product is dissolved in 4-chlorobenzylamine (100 mg) and the mixture is heated to 100° C. for 2h. The reaction mixture is cooled to room temperature and subjected to chromatography using 5% MeOH/CH₂Cl₂. The crude product is recrystallised from CH₂Cl₂/Et₂O to give 8 mg of the title compound as a white solid. Physical characteristics: ¹H NMR (DMSO) δ 10.30, 8.85, 8.29, 7.38, 7.35, 4.57, 4.50, 4.10, 3.72, 3.60, 3.52, 2.45, 2.33; MS (ESI+) m/z 526 (M+H)⁺; HRMS (FAB) m/z 526.2221.

Preparation 49

Methyl 5-Iodo-2-((methylsulfonyl)amino)benzoate [BW.2]

To a solution of 5-iodoanthranilic acid methyl ester (1.00 g) and triethylamine (1.01 mL) in CH₂Cl₂ (25 mL) is added methanesulfonyl chloride (0.59 mL) at 0° C. The ice bath is removed and after 3 h at room temperature the solution is poured into water (20 mL) and extracted with CH₂Cl₂ (2×20 mL). The organic layers are combined, dried over MgSO₄ and the solvent removed in vacuo. The resulting residue is dissolved in CH₃OH (20 mL) and sodium methoxide (20 mL) is added. After 45 min, the solvent is removed in vacuo. The residue is diluted with Et₂O (20 mL) and washed with water (20 mL). The organic layer is separated, dried over MgSO₄, filtered, and concentrated in vacuo. The crude black liquid is purified by silica gel column chromatography (4/1, hexanes/EtOAc ) to afford 0.58g (46%) of the title compound as a brown solid. Physical characteristics: m.p. 119–120° C.; ¹H NMR (300 MHz, CDCl₃) δ 10.41, 8.36, 7.82, 7.52, 3.94, 3.06; IR (diffuse reflectance) 1700, 1682, 1483, 1385, 1335, 1328, 1307, 1249, 1213, 1159, 1147, 1093, 1086, 978, 971 cm⁻¹; MS (FAB) m/z 356 (MH⁺); HRMS (FAB) m/z 355.9447 (C₉H₁₀INO₄S+H). Anal. Found: C, 30.49; H, 2.88; N, 3.96.

Preparation 50

Methyl 5-Iodo-2-(methyl(methylsulfonyl)amino)benzoate [BW.3]

To a solution of methyl 5-iodo-2-((methylsulfonyl)amino) benzoate (Preparation 49, 0.50 g) and $K_2CO_3$ (0.41 g) in DMF (10 mL) is added iodomethane (0.10 mL) at ambient temperature. After 24 hrs, the solvent is removed in vacuo and the residue is partitioned between $Et_2O$ (20 mL) and water (20 mL). The organic layer is separated, dried over $MgSO_4$, filtered, and concentrated in vacuo. The crude yellow liquid is purified by silica gel column chromatography (4/1, hexanes/EtOAc) to afford 0.48 g (92%) of the title compound as a white solid. Physical characteristics: m.p. 105–106° C.; $^1$H NMR (300 MHz, CDCl$_3$) δ 8.22, 7.86, 7.18, 3.91, 3.27, 2.96; IR (diffuse reflectance) 1718, 1443, 1330, 1289, 1258, 1150, 1056, 970, 964, 957, 888, 839, 772, 732, 712 cm$^{-1}$; MS (ESI+) m/z 370 (MH$^+$). Anal. Found: C, 32.74; H, 3.30; N, 3.81.

Preparation 51

Methyl 2-(Methyl(methylsulfonyl)amino)-5-(3-(tetrahydro-2H-pyran-2-yloxy)-1-propynyl)benzoate [BW.4]

To a solution of triethylamine (7 mL) and tetrahydro-2-(2-propylnyloxy)-2H-pyran (0.58 mL) in toluene (10 mL) is added methyl 5-iodo-2-(methyl(methylsulfonyl)-amino) benzoate (Preparation 50, 1.00 g), Pd(PPh$_3$)$_4$ (0.03 g), and CuI (0.01 g). The reaction mixture is allowed to stir for 72 hrs. Methanol (5 mL) is added to the reaction vessel and the solvent is removed in vacuo. The resulting residue is treated with $Et_2O$ (40 mL) and filtered. The filtrate is washed sequentially with 10% HCl, water, and brine. The organic layer is separated, dried over $MgSO_4$, filtered, and concentrated in vacuo. The crude orange liquid is purified via silica gel column chromatography (1/1, hexanes/EtOAc) to afford 1.03 g (100%) of the title compound as a brown liquid. Physical characteristics: $^1$H NMR (300 MHz, CDCl$_3$) δ 7.97, 7.59, 7.39, 4.87, 4.48, 3.90, 3.86, 3.56, 3.27, 2.96, 1.78, 1.61; IR (liq.) 2948, 1732, 1494, 1437, 1342, 1304, 1255, 1232, 1151, 1121, 1098, 1058, 1026, 962, 902 cm$^{-1}$; MS (ESI+) m/z 382 (MH$^+$); HRMS (FAB) m/z 382.1332 ($C_{18}H_{23}NO_6S$+H). Anal. Found:

Preparation 52

1-Methyl-6-(3-(tetrahydro-2H-pyran-2-yloxy)-1-propynyl)-1H-2,1-benzothiazin-4(3H)-one 2,2-Dioxide [BW.5]

To a solution of methyl 2-(methyl(methylsulfonyl) amino)-5-(3-(tetrahydro-2H-pyran -2-yloxy)-1-propynyl) benzoate (Preparation 51, 0.93 g) in DMF (15 mL) at 0° C. is added NaH (0.20 g; 60% dispersion in mineral oil) portionwise. The reaction mixture is warmed to ambient temperature stirring for 1 h upon which methanol (4 mL) is added and the organic portion is washed with a saturated solution of citric acid (50 mL). The aqueous layer is extracted with $Et_2O$ (2×50 mL). The organic layer is separated, dried over $MgSO_4$, filtered, and concentrated in vacuo. The crude orange liquid is purified by silica gel column chromatography (2/1, hexanes/EtOAc) to afford 0.59g (69%) of the title compound as a white solid. Physical characteristics: m.p. 107–108° C.; $^1$H NMR (300 MHz, CDCl$_3$) δ 8.21, 7.71, 7.10, 4.87, 4.48, 4.33, 3.88, 3.55, 3.44, 1.79, 1.62; IR (diffuse reflectance) 2962, 2908, 1684, 1493, 1339, 1211, 1204, 1156, 1135, 1130, 1123, 1030, 899, 886, 838 cm$^{-1}$; MS (ESI-) 348 (M-H$^-$). Anal. Found: C, 58.37; H, 5.58; N, 3.96.

Preparation 53

N-(4-Chlorobenzyl)4-hydroxy-1-methyl-6-(3-(tetrahydro-2H-pyran-2-yloxy)-1-propynyl)-1H-2,1-benzothiazine-3-carboxamide 2,2-Dioxide [BW.6]

To a solution of 1-methyl-6-(3-(tetrahydro-2H-pyran-2-yloxy)-1-propynyl)-1H-2,1-benzothiazin4(3H)-one 2,2-dioxide (Preparation 52, 1.00 g) and triethylamine (0.60 mL) in DMSO (25 mL) is added a solution of 4-chlorobenzylisocyanate (0.72 g) in DMSO (5 mL) at ambient temperature. After 4 h, 10% HCl (100 mL) is added to the reaction vessel and the aqueous layer is extracted with EtOAc (3×100 mL). The organic layers are combined, dried over $MgSO_4$, filtered, and concentrated in vacuo to afford 0.42g (28%) of the title compound as a lime green solid. Physical characteristics: m.p. 148–149° C.; $^1$H NMR (300 MHz, CDCl$_3$) δ 15.81, 8.22, 7.93, 7.71, 7.33, 7.16, 4.91, 4.60, 4.52, 3.91, 3.60, 3.48, 1.86, 1.62; IR (diffuse reflectance) 3373, 2940, 1616, 1574, 1543, 1493, 1390, 1327, 1297, 1279, 1253, 1116, 1097, 1077, 1037 cm$^{-1}$; MS (FAB) m/z 517 (MH$^+$); HRMS (EI) m/z 516.1140 ($C_{25}H_{25}ClN_2O_6S$). Anal. Found: C, 57.55; H, 4.95; N, 5.63.

EXAMPLE 15

N-(4-Chlorobenzyl)-4-hydroxy-6-(3-hydroxy-1-propynyl)-1-methyl-1H-2,1-benzothiazine-3-carboxamide 2,2-Dioxide [BW.7]

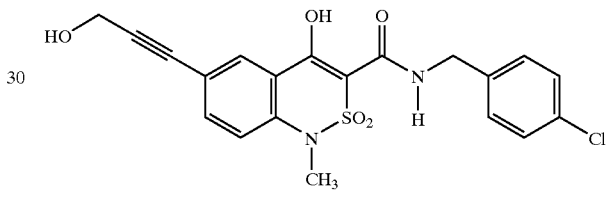

To a solution of N-(4-chlorobenzyl)-4-hydroxy-1-methyl-6-(3-(tetrahydro-2H-pyran-2-yloxy)-1-propynyl)-1H-2,1-benzothiazine-3-carboxamide 2,2-dioxide (Preparation 53, 0.30 g) in $CH_3OH$ (30 mL) is added p-TsOH.$H_2O$ (30 mg). The reaction mixture is heated to 55° C. for 2 h. The solvent is evaporated in vacuo and the residue is diluted with $Et_2O$ (20 mL) and sonicated. The resulting precipitate is filtered and washed with $Et_2O$ to afford 0.16 g (61%) of the title compound as a white solid. Physical characteristics: m.p. 167–168° C.; $^1$H NMR (300 MHz, CDCl$_3$) δ 15.82, 8.21, 7.93, 7.69, 7.36, 7.17, 4.60, 4.53, 3.49, 2.21; IR (diffuse reflectance) 3344, 1615, 1579, 1554, 1540, 1490, 1392, 1385, 1325, 1310, 1293, 1279, 1160, 1093, 1031 cm$^{-1}$; MS (ESI+) m/z 433 (MH$^+$); HRMS (FAB) m/z 433.0614 ($C_{20}H_{17}ClN_2O_5S$+H). Anal. Found: C, 54.57; H, 4.16; N, 6.10.

Preparation 54

2-((2-Amino-3-thienyl)sulfonyl)-N-(4-chlorobenzyl) acetamide, (BC.2, X=Chloro).

A solution containing methyl ((2-amino-3-thienyl) sulfonyl)acetate (0.30 g) (Stephens, C. E.; Sowell, J. W. *J. Heterocyclic Chem.* 1998, 35, 933.) and 4-chlorobenzylamine (0.8 mL) is heated to 110° C. under a stream of nitrogen. The mixture is cooled to room temperature and diluted with $CH_2Cl_2$ and methanol (10/1) and chromatographed on a Biotage column eluting with 20–80% ethyl acetate in heptane (300 mL each 20%) to provide 0.31 g (71%) of the title compound as a white solid. Physical characteristics: HRMS (FAB) m/z 345.0159 ($C_{13}H_{13}ClN_2O_3S_2$+H). Anal. Found: C, 45.49; H, 3.91; N, 7.99.

Preparation 55
N-(4-Chlorobenzyl)-1H-thieno[2,3-e][1,3,4]thiadiazine-3-carboxamide 4,4-Dioxide [BC.3, X=Cl].

A solution containing sodium nitrite (0.06 g) and water (1 mL) is cooled to 0° C. before adding a solution of 2-((2-amino-3-thienyl)sulfonyl)-N-(4-chlorobenzyl)-acetamide (Preparation 54, 0.255 g) in hot acetic acid (10 mL) dropwise. The solution is warmed to room temperature and stirred for 30 minutes. The reaction mixture is poured into a beaker containing ice. The crude product is collected by filtration and dried under high vacuum to provide 0.18 g (66%) of the title compound as a brown solid. Physical characteristics: MS (ESI+) m/z 356 (M+H)+.

Preparation 56
N-(4-Chlorobenzyl)-1-methyl-1H-thieno[2,3-e][1,3,4]thiadiazine-3-carboxamide 4,4-Dioxide, [BD.1, X=Chloro].

DMF (2 mL, anhydrous) is added to a flask containing N-(4-chlorobenzyl)-1H-thieno[2,3-e][1,3,4]thiadiazine-3-carboxamide 4,4-dioxide (Preparation 55, 0.17 g) and potassium carbonate (0.20 g). To this mixture is added iodomethane (36 μL) and the resulting brown solution is stirred at room temperature for 30 minutes under an atmosphere of nitrogen. After diluting with dichloromethane (50 mL), this solution is poured into water (100 mL) and the layers are separated. The organic layer is washed with brine, dried over $Na_2SO_4$, filtered, and concentrated to provide 0.15 g (85%) of the title compound as a brown residue. Physical characteristics: MS (ESI+) m/z 370 (M+H)+.

Preparation 57
6-Bromo-N-(4-chlorobenzyl)-1-methyl-1H-thieno[2,3-e][1,3,4]thiadiazine-3-carboxamide 4,4-Dioxide [BD.2, X=Chloro].

A solution containing N-(4-chlorobenzyl)-1-methyl-1H-thieno[2,3-e][1,3,4]-thiadiazine-3-carboxamide 4,4-dioxide (Preparation 56, 0.14 g) and anhydrous DMF (2 mL) is stirred under nitrogen while adding N-bromosuccinimide (0.074 g) in one portion. This solution is stirred overnight at room temperature before diluting with $CH_2Cl_2$ (50 mL) and washing with water (60 mL). The organic portion is separated and washed with brine, dried over $Na_2SO_4$, filtered, and concentrated to give a brown oil. Physical characteristics: MS (ESI+) m/z 448 (M+H)+, 450.

EXAMPLE 16
N-(4-Chlorobenzyl)-6-(3-hydroxy-1-propynyl)-1-methyl-1H-thieno[2,3-e][1,3,4]-thiadiazine-3-carboxamide 4,4-Dioxide [BD.3, X=Chloro, Z=CH$_2$OH].

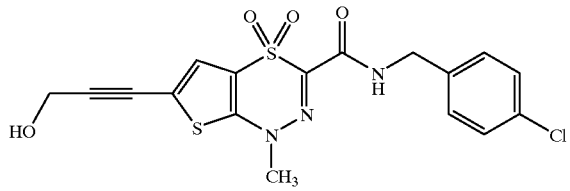

A solution containing the 6-bromo-N-(4-chlorobenzyl)-1-methyl-1H-thieno[2,3-e]-[1,3,4]thiadiazine-3-carboxamide 4,4-dioxide (Preparation 57, 0.19 g), DMF (6 mL), and triethylamine (0.8 mL) is degassed by evacuation under house vacuum and filling with nitrogen 3 times. To this solution is added propargyl alcohol (24 μL), palladium(II) chloride bistriphenylphosphine (8 mg), and copper(I)iodide (14 mg). The mixture is warmed to 65° C. After cooling, the reaction mixture is concentrated under a stream of nitrogen and the resulting residue is partitioned between $CH_2Cl_2$ and water. The organic layer is washed with brine, dried over $Na_2SO_4$, filtered, and concentrated to give a brown oil. The crude product is chromatographed on a Biotage column eluting with 60% ethyl acetate in heptane (200 mL), 80% ethyl acetate in heptane (200 mL), and ethyl acetate (500 mL) followed by purification by radial chromatography eluting with $CH_2Cl_2$ to give 40 mg (25%) of the title compound as a pale yellow solid. Physical characteristics: M.p. 98° C. (dec); MS (ESI+) m/z 446 (M+Na)+; HRMS (FAB) m/z 424.0191 ($C_{17}H_{14}ClN_3O_4S_2$+H).

Preparation 58
Ethyl 6-Chloro-4-hydroxy[1,5]naphthyridine-3-carboxylate [I.3, Y=chloro].

A solution of diethyl 2-(((6-chloro-3-pyridinyl)amino)methylene)malonate (Heindl, J. *Eur. J. Med. Chem. Chim. Ther.* 1977, 12, 549–555) (1.00 g) in diphenyl ether (110 mL) is degassed by three cycles of evacuation and nitrogen purging at room temperature. The solution is heated rapidly to reflux and stirred for 15 minutes. After cooling, the mixture is diluted with diethyl ether (150 mL), stirred vigorously for 5 minutes, and then filtered. The collected solid is washed repeatedly with ether and then dried under vacuum, affording 0.711 g (84%) of the title compound as a beige powder. Physical Characteristics. $^1$H NMR (DMSO-$d_6$) δ 8.61, 8.12, 7.79, 4.23, 1.29; HRMS (FAB) m/z 253.0387 ($C_{11}H_9ClN_2O_3$+H). Anal. Found: C, 52.25; H, 3.53; N, 11.23.

Preparation 59
Ethyl 6-Chloro-1-methyl-4-oxo-1,4-dihydro[1,5]naphthyridine-3-carboxylate [I.4, Y=chloro].

A mixture of ethyl 6-chloro-4-hydroxy[1,5]naphthyridine-3-carboxylate (Preparation 58, 694 mg), potassium carbonate (588 mg), and iodomethane (264 μL) in DMF (15 mL) is stirred at room temperature for 5 hours. The mixture is poured into water (50 mL), and the solution is extracted with $CH_2Cl_2$ (3×50 mL). The organic layers are dried (MgSO$_4$) and concentrated. Trituration with ether (50 mL) affords 473 mg (65%) of the title compound as an off-white solid. Physical Characteristics. $^1$H NMR (DMSO-$d_6$) δ 8.70, 8.31, 7.90, 4.24, 3.92, 1.29; HRMS (FAB) m/z 267.0535 ($C_{12}H_{11}ClN_2O_3$+H). Anal. Found: C, 54.14; H, 4.24; N, 10.58.

Preparation 60
Ethyl 6-(3-Hydroxy-1-propynyl)-1-methyl-4-oxo-1,4-dihydro[1,5]naphthyridine-3-carboxylate [K.1, Z=CH$_2$OH].

Triethylamine (10 mL) is added to dry cuprous iodide (52 mg) under nitrogen. The mixture is stirred for 5 minutes and propargyl alcohol (50 μL) is added. After stirring another 5 minutes, dichlorobis(triphenylphosphine)palladium(II) (48 mg) is added. The mixture is again stirred for 5 minutes before the addition of ethyl 6-chloro-1-methyl-4-oxo-1,4-dihydro[1,5]naphthyridine-3-carboxylate (Preparation 59, 367 mg) and DMF (10 mL). After stirring another 5 minutes, the remaining propargyl alcohol (660 μL) is added, and the reaction is tightly capped and stirred at 70° C. for 11 hours. After cooling, the dark mixture is diluted with ether (75 mL), sonicated to break up the solids, and filtered. The collected solid is washed with ether and dried under vacuum. The crude solid is recrystallized from 95% ethanol (100 mL, dissolved at reflux with the addition of a few drops of water, then cooled to 0° C. overnight), affording 219 mg (55%) of the title compound as a beige solid. Physical characteristics. $^1$H NMR (DMSO-$d_6$) δ 8.68, 8.21, 7.85, 5.5, 4.38, 4.23, 3.90, 1.29; HRMS (FAB) ($C_{15}H14N_2O_4$+H) m/z 287.1035. Anal. Found ($C_{15}H_{14}N_2O_4$.0.12 $H_2O$): C, 62.48; H, 5.00; N, 9.62.

EXAMPLE 17
N-(4-Chlorobenzyl)-6-(3-hydroxy-1-propynyl)-1-methyl-4-oxo-1,4-dihydro[1,5]-naphthyridine-3-carboxamide [K.2, Z=CH$_2$OH].

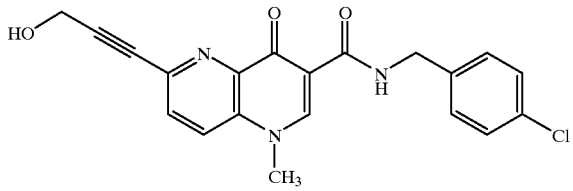

Trimethylaluminum (2M in toluene, 42 µL) is added dropwise to a room temperature solution of 4-chlorobenzylamine (17 µL) in CH$_2$Cl$_2$ (1 mL) under nitrogen. The solution is stirred for 5 minutes before the addition in one portion of ethyl 6-(3-hydroxy-1-propynyl)-1-methyl4-oxo-1,4-dihydro[1,5]naphthyridine-3-carboxylate (Preparation 60, 20 mg). The resulting suspension is stirred at room temperature for 3.5 h. The reaction mixture is partitioned with dil. aq. HCl (2 mL) and extracted with CH$_2$Cl$_2$ (2×2 mL). After drying over MgSO$_4$, the extracts are concentrated under vacuum. The crude residue is purified by flash chromatography (9 g silica, 10% methanol/CH$_2$Cl$_2$) to give 14 mg (52%) of the title compound as a lt. yellow solid. Physical Characteristics: R$_f$ (15% methanol/CH$_2$Cl$_2$)=0.53; $^1$H NMR (DMSO-d$_6$) δ 10.32, 8.90, 8.31, 7.90, 7.40, 7.36, 5.5, 4.58, 4.39, 4.01; HRMS (FAB) m/z 382.0963 (C$_{20}$H$_{16}$ClN$_3$O$_3$+H). Anal. Found (C$_{20}$H$_{16}$ClN$_3$O$_3$.0.24 H$_2$O): C, 62.21; H, 4.21; N, 10.75.

Preparation 61
4-Bromo-5-chloro-2-thiophenecarbaldehyde [BQ.2]

n-BuLi (2.5 M in hexanes, 105 mL) is slowly added to a solution of diisopropylamine (36.8 mL) in THF (600 mL) at 0° C. After 15 min, the mixture is cooled to −70° C. A solution of 3-bromo-2-chlorothiophene (49.4 g) in THF (20 mL) is added maintaining the internal temperature <−65° C. After 15 min, DMF (25.2 mL) is added. The mixture is stirred at −70° C. for 15 min and then allowed to warm to room temperature. The reaction mixture is quenched with saturated aq. NH$_4$Cl solution (200 mL) and concentrated in vacuo to one-half volume. The residue is diluted with EtOAc (500 mL) and the aqueous layer is separated. The aqueous layer is extracted with EtOAc (2×100 mL). The combined organic layers are washed with brine (100 mL), dried (MgSO$_4$), and concentrated to afford an oil. The oil is purified by column chromatography (heptane; heptane/EtOAc, 20/1; 10/1) and the resulting solid is suspended in heptane (75 mL) and filtered to afford 30.3 g (54%) of the title compound as a light yellow solid. Physical characteristics: M.p. 61–62° C.; $^1$H NMR (300 MHz, DMSO-d$_6$) δ 9.82, 8.14; $^{13}$C NMR (100 MHz, CDCl$_3$) δ 181.6, 140.9, 138.5, 138.1, 112.8.

Preparation 62
4-((4-Bromo-5-chloro-2-thienyl)methyl)morpholine [BQ.3]

Morpholine (15.2 mL), acetic acid (9.1 mL), and then sodium triacetoxyborohydride (50.3 g) is added to a solution of 4-bromo-5-chloro-2-thiophenecarbaldehyde (Preparation 61, 35.7 g) in 1,2-dichloroethane (600 mL) at 0° C. The mixture is allowed to warm to room temperature, and after 18 h, it is quenched with a 2N NaOH solution (200 mL) with ice bath cooling. The organic layer is separated and washed with 1 N NaOH solution (2×200 mL). The aqueous layers are extracted with CH$_2$Cl$_2$ (2×100 mL). The combined organic layers are extracted with 0.25 M HCl solution (2 L) and the resulting aqueous layer is made basic with 2N NaOH solution. The mixture is then extracted with CH$_2$Cl$_2$ (2 L) and the organic layer is dried (Na$_2$SO$_4$) and concentrated to afford 39.24 g (84%) of the title compound as a light yellow oil. Physical characteristics: $^1$H NMR (400 MHz, DMSO-d$_6$) δ 7.03, 3.63, 3.57, 2.42; $^{13}$C NMR (100 MHz, CDCl$_3$) δ 140.9, 127.3, 125.9, 109.2, 66.9, 57.6, 53.3; MS (ESI+) m/z 296 (72, (M+H)$^+$), 298 (100).

Preparation 63
1-(2-Chloro-5-(4-morpholinylmethyl)-3-thienyl)ethanone [BQ.4]

4-((4-Bromo-5-chloro-2-thienyl)methyl)morpholine (Preparation 62, 7.65 g) is dissolved in diethyl ether (75 mL) and is cooled to −75° C. A solution of n-butyllithium (2.5 M in hexane, 11.0 mL) is added via addition funnel, maintaining the temperature below 68° C. The reaction is stirred for 15 minutes at −70° C. and allowed to warm to 0° C. A solution of N-methoxy-N-methylacetamide (3.09 g) in ether (5 mL) is added via addition funnel, maintaining the temperature below 5° C. The reaction is stirred at 0° C. for 1 h and allowed to warm to rt. The reaction is quenched with saturated aq. NH$_4$Cl solution (50 mL) and made basic with sat. aq. NaHCO$_3$. The mixture is extracted with ethyl acetate (3×125 mL). The combined organic layers are washed with sat. NaHCO$_3$ (2×100 mL) and brine (50 mL). The combined aqueous washes are back-extracted with ethyl acetate (100 mL). The organic layers are combined, dried (Na$_2$SO$_4$), and concentrated in vacuo to a yellow oil. The crude product is chromatographed, eluting with 25% ethyl acetate/heptane to afford 2.42 g (37%) of the title compound. Physical characteristics: $^1$H NMR (400 MHz, DMSO-d$_6$) δ 7.33, 3.64, 3.58, 2.51; IR (liq.) 2854, 2809, 1673, 1456, 1372, 1351, 1328, 1243, 1212, 1165, 1118, 1034, 1008, 867, 618 cm$^{-1}$; HRMS (FAB) m/z 260.0506 (C$_{11}$H$_{14}$ClNO$_2$S+H). Anal. Found: C, 50.77; H, 5.51; N, 5.35; Cl, 13.24; S, 12.00.

Preparation 64
Methyl 3-(2-Chloro-5-(4-morpholinylmethyl)-3-thienyl)-3-oxopropanoate [BN.1]

To a solution of 1-(2-chloro-5-(4-morpholinylmethyl)-3-thienyl)ethanone (Preparation 63, 9.53g) in dimethylcarbonate (200 mL) is added NaH (1.53 g; 60% dispersion in mineral oil) portionwise at ambient temperature. The reaction mixture is heated to 95° C. for 3 h. The reaction vessel is cooled to ambient temperature and the mixture is poured into ice cold water (500 mL) containing acetic acid (15 mL). The aqueous layer is extracted with Et$_2$O (3×100 mL). The organic layer is separated, dried over MgSO$_4$, filtered, and concentrated in vacuo. The crude brown liquid is purified by silica gel column chromatography (4/1, hexanes/EtOAc) to afford 4.77g (41%) of the title compound as a tan solid. Physical characteristics: m.p. 67–68° C.; $^1$H NMR (300 MHz, CDCl$_3$) δ 7.21, 3.99, 3.78, 3.71, 3.60, 2.50; IR (diffuse reflectance) 2822, 1738, 1663, 1461, 1399, 1350, 1336, 1316, 1286, 1265, 1156, 1113, 1009, 1004, 864 cm$^{-1}$; MS (ESI+) m/z 318; Anal. Found: C, 48.89; H, 5.13; N, 4.45.

Preparation 65
Methyl (2Z)-3-(2-Chloro-5-(4-morpholinylmethyl)-3-thienyl)-3-oxo-2-(phenyl-hydrazono)propanoate [BO.1, aryl=phenyl, Y=morpholinylmethyl]

To a solution of aniline (2.52 mL) in 6M HCl (15 mL) is added dropwise a solution of NaNO$_2$ (2.44 g) in water (8 mL) at -10° C. The solution stirs at 0° C. for 1 h and is poured into a solution of methyl 3-(2-chloro-5-(4- morpholinylmethyl)-3-thienyl)-3-oxopropanoate (Preparation 64, 3.50 g) in pyridine (15 mL) and water (8 mL) with vigorous stirring at −10° C. The solution stirs at 0° C. for 60 min and is diluted with cold water (150 mL). The aqueous layer is extracted with EtOAc (3×150 mL). The organic layers are combined, dried over MgSO$_4$, filtered, and concentrated in vacuo. The crude red liquid (2.93 g) is utilized without any further purification. Physical characteristics: IR (liq.) 1737, 1675, 1529, 1455, 1437, 1330, 1306, 1263, 1239, 1218, 1201, 1168, 1144, 1117, 755 cm$^{-1}$; MS (FAB) m/z 422 (MH$^+$); HRMS (FAB) m/z 422.0935 (C$_{19}$H$_{20}$ClN$_3$O$_4$S+H).

Preparation 66
Methyl 6-(4-Morpholinylmethyl)-4-oxo-1-phenyl-1,4-dihydrothieno[2,3-c]-pyridazine-3-carboxylate [BO.2, aryl=phenyl, Y=morpholinylmethyl]

To a solution of methyl (2Z)-3-(2-chloro-5-(4-morpholinylmethyl)-3-thienyl)-3-oxo-2-(phenylhydrazono) propanoate (Preparation 65, 2.67 g) in dry THF (150 mL) is added NaH (0.43 g; 60% dispersion in mineral oil) portionwise at ambient temperature. The reaction is continued overnight and the solvent is removed in vacuo. Water (50 mL) is added to residue and the aqueous layer is extracted with EtOAc (3×50 mL). The organic layer is separated, dried over MgSO$_4$, filtered, and concentrated in vacuo. The resulting precipitate is filtered to afford 0.38 g (16%) of the title compound as a brown solid. Physical characteristics: m.p. 167–169° C.; $^1$H NMR (400 MHz, CDCl$_3$) δ 7.67, 7.57, 7.43, 3.98, 3.68, 2.50; IR (diffuse reflectance) 2816, 1731, 1615, 1515, 1353, 1279, 1200, 1172, 1133, 1121, 1106, 1026, 867, 809, 749 cm$^{-1}$; MS (ESI+) 386; HRMS (FAB) m/z 386.1180 (C$_{19}$H$_{19}$N$_3$O$_4$S+H). Anal. Found: C, 59.14; H, 5.02; N, 10.48.

EXAMPLE 18
N-(4-Chlorobenzyl)-6-(4-morpholinylmethyl)-4-oxo-1-phenyl-1,4-dihydrothieno[2,3-c]pyridazine-3-carboxamide [BO.3, aryl=phenyl, Y=morpholinylmethyl]

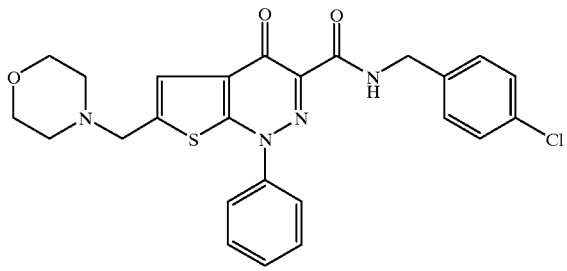

A solution of methyl 6-(4-morpholinylmethyl)-4-oxo-1-phenyl-1,4-dihydrothieno[2,3-c]pyridazine-3-carboxylate (0.29 g) in 4-chlorobenzylamine (2 mL) is heated to 190 ° C. for 30 min. The reaction mixture is cooled to ambient temperature, the solvent is removed in vacuo and Et$_2$O (15 mL) is added to the residue. The resulting precipitate is filtered and rinsed with Et$_2$O to afford 0.24 g (65%) of the title compound as a tan solid. Physical characteristics: m.p. 182–184° C.; $^1$H NMR (400 MHz, CDCl$_3$) δ 10.56, 7.71, 7.58, 7.42, 7.32, 4.69, 3.71, 3.65, 2.51; IR (diffuse reflectance) 1677, 1587, 1549, 1532, 1508, 1493, 1347, 1297, 1278, 1261, 1115, 1112, 799, 777, 701 cm$^{-1}$; MS (EI) m/z 494 (M$^+$); HRMS (FAB) m/z 495.1265 (C$_{25}$H$_{23}$ClN$_4$O$_3$S+H). Anal. Found: C, 60.18; H, 4.79; N, 11.04.

EXAMPLE 19
N-(4-Chlorobenzyl)-6-(4-morpholinylmethyl)-4-oxo4H-chromene-3-carboxamide [AO.2, X=chloro, Z=H]

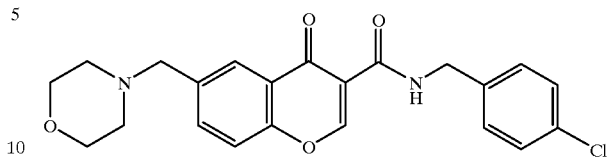

A mixture of 6-methyl-3-formylchoromone (150 mg) and NBS (285 mg) in carbon tetrachloride (25 mL) is irradiated with a 650 W halogen lamp for 20 min. After the mixture is cooled to room temperature, the resulting precipitate is filtered. The filtrate is cooled to 0° C. and treated with 4-chlorobenzylamine (200 mg) for 30 min. The mixture is partitioned between CH$_2$Cl$_2$ (20 mL) and 0.5 N aqueous HCl solution (30 mL). The organic layer is separated, dried (MgSO$_4$), and concentrated. The residue is dissolved in DMF (5 mL) and treated with morpholine (0.5 mL) at room temperature for 20 min. The mixture is diluted with CH$_2$Cl$_2$ (100 mL) and washed with water. The organic layer is separated, dried (MgSO$_4$), and concentrated. The residue is purified on a silica plate (CH$_2$Cl$_2$/MeOH, 30/1) to give 35 mg of the title compound as a white solid. Physical chracteristics: $^1$H NMR (DMSO) δ 9.60, 9.06, 8.08, 7.85, 7.75, 7.41, 7.37, 4.55, 3.62, 3.58, 2.38; MS (ESI+) m/z 413 (M+H)$^+$; Anal. Found: C, 63.79; H, 5.16; N, 6.73.

EXAMPLE 20
N-(4-Chlorobenzyl)-6,8-bis(4-morpholinylmethyl)-4-oxo-4H-chromene-3-carboxamide [AO.2, X=chloro, Z=morpholinylmethyl]

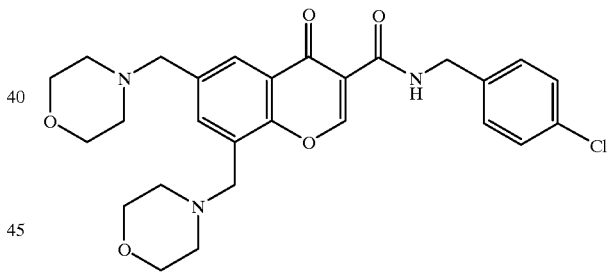

A mixture of 6,8-dimethyl-3-formylchoromone (202 mg) and NBS (600 mg, 3.37 mmol) in carbon tetrachloride (40 mL) is irradiated with 650 W halogen lamp for 20 min. After the mixture is cooled to room temperature, the resulting precipitate is filtered. The filtrate is cooled to 0° C. and treated with 4-chlorobenzylamine (256 mg) for 30 min. The mixture is partitioned between CH$_2$Cl$_2$ (30 mL) and 0.5 N aqueous HCl solution (40 mL). The organic layer is separated, dried (MgSO$_4$), and concentrated. The residue is dissolved in DMF (5 mL) and treated with morpholine (0.5 mL) at room temperature for 20 min. The mixture is diluted with methylene chloride (100 mL) and washed with water. The organic layer is separated, dried (MgSO$_4$), and concentrated. The residue is purified on a silica plate (acetone/hexanes, 2/1) to give 25 mg of the title compound as a pale yellow solid. Physical chracteristics: $^1$H NMR (DMSO) δ 9.59, 9.06, 8.00, 7.85, 7.41, 7.37, 4.55, 3.80, 3.62, 3.58, 2.44, 2.38; MS (ESI+) m/z 512 (M+H)$^+$; Anal. Found: C, 63.15; H, 5.91; N, 8.14.

EXAMPLE 21
N-(4-Chlorobenzyl)-6-(((3R)-3-hydroxypyrrolidinyl) methyl)-4-oxo-4H-chromene-3-carboxamide [AO.2]

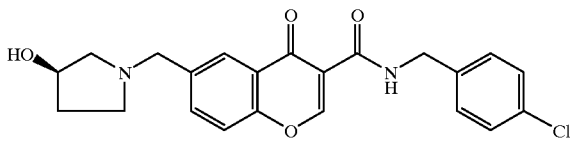

A mixture of 6-methyl-3-formylchoromone (150 mg) and NBS (285 mg) in carbon tetrachloride (25 mL) is irradiated with a 650 W halogen lamp for 20 min. After the mixture is cooled to room temperature, the resulting precipitate is filtered. The filtrate is cooled to 0° C. and treated with 4-chlorobenzylamine (200 mg) for 30 min. The mixture is partitioned between $CH_2Cl_2$ (20 mL) and 0.5 N aqueous HCl solution (30 mL). The organic layer is separated, dried ($MgSO_4$), and concentrated. The residue is dissolved in DMF (5 mL) and treated with (R)-3-hydroxypyrrolidine (140 mg) at room temperature for 16 h. The mixture is diluted with methylene chloride (100 mL) and washed with water. The organic layer is separated, dried ($MgSO_4$), and concentrated. The residue is purified on a silica plate (acetone/hexanes, 1/1) to give 15 mg of the title compound as a pale yellow solid which is further recrystallized from diethyl ether/hexanes to give an analytical sample. Physical chracteristics: $^1$H NMR (DMSO) δ 9.60, 9.06, 8.07, 7.84, 7.74, 7.41, 7.38, 4.72, 4.55, 4.20, 3.73, 2.3–2.8, 2.09, 1.56; MS (ESI+) m/z 413 (M+H)$^+$; Anal. Found ($C_{22}H_{21}ClN_2O_4 \cdot 0.25\ H_2O$): C, 63.17; H, 5.28; N, 6.63;

Testing of Inventive Compounds

The antiviral activity of a compound of the invention can be determined using pharmacological models which are well known to the art, or using the test described below.

While many of the compounds of the present invention can demonstrate activity against the CMV polymerase, these compounds may be active against the cytomegalovirus by this or other mechanisms of action. Thus, the description below of these compounds' activity against the CMV polymerase is not meant to limit the present invention to a specific mechanism of action.

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 µl volume with 5.4 mM HEPES (pH 7.5), 11.7 mM KCl, 4.5 mM $MgCl_2$, 0.36 mg/ml BSA, and 90 nM $^3$H-dTTP. Assays are run with and without CHAPS, (3-[(3-Cholamidopropyl)-dimethylammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 µg/ml BSA, and 0.01% sodium azide. The HCMV polymerase, which is expressed in recombinant baculovirus-infected SF-9 cells and purified according to literature procedures, is added at 10% (or 10 µl) of the final reaction volume, i.e., 100 µl. Compounds are diluted in 50% DMSO and 10 µl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25° C. or 37° C. water bath and terminated via the addition of 40 µl/reaction of 0.5 M EDTA (pH 8) per well. Reactions are terminated within the timeframe during which substrate incorporation is linear and varied depending upon the enzyme and conditions used, i.e., 30 min. for HCMV polymerase. Ten µl of streptavidin-SPA beads (20 mg/ml in PBS/10% glycerol) are added following termination of the reaction. Plates are incubated 10 min. at 37° C., then equilibrated to room temperature, and counted on a Packard Topcount. Linear regressions are performed and $IC_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction.

Having described the invention in detail and by reference to the preferred embodiments thereof, it will be apparent that modifications and variations are possible without departing from the scope of the appended claims.

What is claimed is:
1. A compound of formula I,

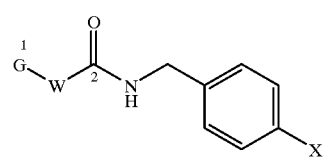

wherein,
X is Cl, Br, F, CN, or $NO_2$;
G is
 (a) $C_{0-4}$alkyl which is fully saturated or partially unsaturated and is substituted by hydroxy, or
 (b) $C_{1-4}$alkyl substituted by $NR^1R^2$ or 4-tetrahydropyran;
$R^1$ is $C_{2-7}$alkyl substituted by hydroxy, $C_{1-4}$alkoxy, heteroaryl, or aryl;
$R^2$ is hydrogen or $C_{1-7}$alkyl; or $R^1$ and $R^2$ together with the nitrogen to which they are attached form morpholine which may be optionally substituted by aryl or $C_{1-7}$alkyl; or pyrrolidine substituted by hydroxy;
W is a heterocycle of formula W3.1

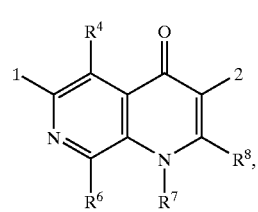

$R^4$ is H, halo, or $C_{1-4}$alkyl optionally substituted by one to three halogens;
$R^6$ is
 (a) H,
 (b) halo,
 (c) aryl, (d) het,
(e) $OR^{12}$,
(f) $SR^{12}$,
(g) $C_{1-7}$alkyl which may be partially unsaturated and optionally substituted by one or more substituents selected from $OR^{12}$, $SR^1$, $NR^{10}R^{11}$, aryl, halo, $C_{3-8}$cycloalkyl optionally substituted by $OR^{12}$, or het attached through a carbon atom,
(h) $NR^{10}OR^{11}$,
(i) $C_{3-8}$cycloalkyl which may be partially unsaturated and is optionally substituted by one or more substituents selected from halogen, $OR^{12}$, $SR^1$, $NR^{10}R^{11}$,
(j) $(C=O)R^9$,
(k) $S(O)_mR^9$,
(l) $(C=O)OR^2$,
(m) $NHSO_2R^9$,
(n) nitro, or
(o) cyano;

$R^7$ is
(a) $C_{1-7}$alkyl which may be partially unsaturated and optionally substituted by one or more substituents selected from $OR^{12}$, $SR^1$, $NR^{10}R^{11}$, or halo,
(b) $C_{3-8}$cycloalkyl which may be partially unsaturated and is optionally substituted by one or more substituents selected from halogen, $OR^{12}$, $SR^1$, $NR^{10}R^{11}$,
(c) aryl, or
(d) het;

$R^8$ is
(a) H,
(b) $C_{1-7}$alkyl which may be partially unsaturated and optionally substituted by one or more substituents selected from $OR^{12}$, $SR^1$, $NR^{10}R^{11}$, or halo,
(c) $OR^{12}$, or
(d) $SR^{12}$;

$R^9$ is
(a) $C_{1-7}$alkyl,
(b) $NR^{10}R^{11}$,
(c) aryl, or
(d) het, wherein said het is bound through a carbon atom;

$R^{10}$ and $R^{11}$ are independently
(a) H,
(b) aryl,
(c) $C_{1-7}$alkyl which may be partially unsaturated and is optionally substituted by one or more substituents selected from $CONR^2R^2$, $CO_2R_2$, het, aryl, cyano, or halo,
(d) $C_{2-7}$alkyl which may be partially unsaturated and is substituted by one or more substituents selected from $NR^2R^2$, $OR^2$, or $SR^2$,
(e) $C_{3-8}$cycloalkyl which may be partially unsaturated and is optionally substituted by one or more substituents selected from halogen, $OR^2$, $SR^2$, or $NR^2R^2$, or
(f) $R^{10}$ and $R^{11}$ together with the nitrogen to which they are attached form a het;

$R^{12}$ is
(a) H,
(b) aryl,
(c) het
(d) $C_{1-7}$alkyl optionally substituted by aryl, or halogen,
(e) $C_{2-7}$alkyl substituted by $OR^2$, $SR^2$, or $NR^2R^2$, or
(f) $C_{3-8}$cycloalkyl which may be partially unsaturated and is optionally substituted by one or more substituents selected from halogen, $OR^2$, $SR^2$, or $NR^2R^2$;

each m is independently 1 or 2;

aryl is a phenyl radical or an ortho-fused bicyclic carbocyclic radical wherein at least one ring is aromatic, and aryl maybe optionally substituted with one or more substituents selected from halo, OH, cyano, $NR^2R$, $CO_2R^2$, $CF_3$, $C_{1-6}$alkoxy, and $C_{1-6}$alkyl which maybe further substituted by one to three $SR^2$, $NR^2R^2$, $OR^2$, or $CO_2R^2$ groups;

het is a four- (4), five- (5), six- (6), or seven- (7) membered saturated or unsaturated heterocyclic ring having 1, 2, or 3 heteroatoms selected from oxygen, sulfur, or nitrogen, which is optionally fused to a benzene ring, or any bicyclic heterocycle group, and het may be optionally substituted with one or more substituents selected from halo, OH, cyano, phenyl, $CO_2R^2$, $CF_3$, $C_{1-6}$alkoxy, oxo, oxime, and $C_{1-6}$alkyl which may be further substituted by one to three $SR^2$, $NR^2R^2$, $OR^2$, or $CO_2R^2$ groups;

halo or halogen is F, Cl, Br, I;

1 represents the point of attachment between W and G;

2 represents the point of attachment between W and the carbonyl group of Formula (I);

and a pharmaceutically acceptable salt thereof.

2. A compound of claim 1 wherein G is $C_{1-4}$alkyl substituted by $NR^1R^2$.

3. A compound of claim 2 wherein G is morpholinylmethyl.

4. A compound of claim 1 wherein $R^6$ is H, halo, or morpholinylmethyl.

5. A compound of claim 4 wherein halo is Cl.

6. A compound of claim 1 wherein $R^7$ is $C_{1-4}$alkyl.

7. A compound of claim 6 wherein $R^7$ is $CH^3$.

8. A compound of claim 1 wherein G is $C_{1-4}$alkyl substituted by $NR^1R^2$, H, halo, or morpholinylmethyl, and $R^7$ is $C_{1-4}$alkyl.

9. A compound as in any one of claims 1–8 wherein X is Cl.

10. compound according to claim 1 which is:
(1) N-(4-chlorobenzyl)-6-(3-hydroxy-1-propyl)-1-methyl-4-oxo-1,4-dihydro[1,7]-naphthyridine-3-carboxamide;
(2) N-(4-chlorobenzyl)-6-(3-hydroxypropyl)-1-methyl-4-oxo-1,4-dihydro[1,7]-naphthyridine-3-carboxamide;
(3) N-(4-chlorobenzyl)-1-methyl-6,8-bis(morpholin-4-ylmethyl)-4-oxo-1,4-dihydro-1,7-naphthyridine-3-carboxamide;
(4) N-(4-chlorobenzyl)-8-ethoxy-6-(3-hydroxy-1-propynyl)-1-methyl-4-oxo-1,4-dihydro[1,7]naphthyridine-3-carboxamide;
(5) N-(4-chlorobenzyl)-8-ethoxy-6-(3-hydroxypropyl)-1-methyl-4-oxo-1,4-dihydro[1,7]naphthyridine-3-carboxamide;
(6) N-(4-chlorobenzyl)-1-methyl-6-(4-morpholinylmethyl)-4-oxo-1,4-dihydro[1,7]-naphthyridine-3-carboxamide;
(7) 8-chloro-N-(4-chlorobenzyl)-1-methyl-6-(4-morpholinylmethyl)-4-oxo-1,4-dihydro 1,7]naphthyridine-3-carboxamide;
(8) N-(4-chlorobenzyl)-8-ethoxy-1-methyl-6-(4-morpholinylmethyl)-4-oxo-1,4-dihydro[1,7]naphthyridine-3-carboxamide; or a pharmaceutically acceptable salt thereof.

11. A compound according to claim 1 which is;
(1) 8-chloro-N-(4-chlorobenzyl)-1-methyl-6-(4-morpholinylmethyl)-4-oxo-1,4-dihydro 1,7]naphthyridine-3-carboxamide;

(2) N-(4-chlorobenzyl)-1-methyl-6-(4-morpholinylmethyl)-4-oxo-1,4-dihydro[1,7]-naphthyridine-3-carboxamide;

(3) N-(4-chlorobenzyl)-1-methyl-6,8-bis(morpholin-4-ylmethyl)-4-oxo-1,4-dihydro-1,7-naphthyridine-3-carboxamide; or a pharmaceutically acceptable salt thereof.

12. A compound according to claim 1 which is;

(1) 8-chloro-N-(4-chlorobenzyl)-1-methyl-6-(4-morpholinylmethyl)-4-oxo-1,4-dihydro 1,7] naphthyridine-3-carboxamide;

(2) N-(4-chlorobenzyl)-1-methyl-6,8-bis(morpholin-4-ylmethyl)-4-oxo-1,4-dihydro-1,7-naphthyridine-3-carboxamide; or a pharmaceutically acceptable salt thereof.

13. A pharmaceutical composition comprising a compound of claim 1 and a pharmaceutically acceptable carrier.

14. A method of treating a viral infection in a mammal comprising utilizing a compound of claim 1.

15. A method according to claim 14 wherein said viral infection is a herpes virus infection.

16. A method according to claim 14 wherein said mammal is a human.

17. A method according to claim 14 wherein said mammal is a livestock or companion animal.

18. A method according to claim 15 wherein the infection is herpes simplex virus type 1, 2, 6, 7, or 8, varicella zoster virus, human cytomegalovirus, or Epstein-Barr virus.

19. A method according to claim 15 wherein the infection is herpes simplex virus type 1 or 2, human herpes virus type 8, varicella zoster virus, human cytomegalovirus, or Epstein-Barr virus.

20. A method according to claim 14 wherein the amount administered is from about 0.1 to about 300 mg/kg of body weight.

21. A method according to claim 20 wherein the amount administered is from about 1 to about 30 mg/kg of body weight.

22. A method according to claim 14, wherein the compound is administered parenterally, topically, intravaginally, orally, or rectally.

23. A method for inhibiting a viral DNA polymerase, comprising contacting the polymerase with an effective inhibitory amount of a compound of claim 1.

24. A method of claim 23 wherein the polymerase and the compound are contacted in vitro.

25. A method of claim 23 wherein the polymerase and the compound are contacted in vivo.

* * * * *